US009695399B2

(12) United States Patent
Woodruff et al.

(10) Patent No.: US 9,695,399 B2
(45) Date of Patent: Jul. 4, 2017

(54) 3D MICROPHYSIOLOGIC SYSTEM

(71) Applicants: Northwestern University, Evanston, IL (US); The Board of Trustees of the University of Illinois, Urbana, IL (US)

(72) Inventors: Teresa K. Woodruff, Chicago, IL (US); Ji-Yong Julie Kim, Elmhurst, IL (US); Joanna E. Burdette, Chicago, IL (US); Spiro Getsios, Chicago, IL (US); Sevim Yildiz Arslan, Chicago, IL (US); Shuo Xiao, Chicago, IL (US); Jie Zhu, Chicago, IL (US)

(73) Assignees: Northwestern University, Evanston, IL (US); Board of Trustees of the University of Illinois, Urbana, IL (US)

( * ) Notice: Subject to any disclaimer, the term of this patent is extended or adjusted under 35 U.S.C. 154(b) by 162 days.

(21) Appl. No.: 14/607,862

(22) Filed: Jan. 28, 2015

(65) Prior Publication Data

US 2015/0252328 A1    Sep. 10, 2015

Related U.S. Application Data

(60) Provisional application No. 61/932,592, filed on Jan. 28, 2014.

(51) Int. Cl.
| | |
|---|---|
| *C12N 5/07* | (2010.01) |
| *C12N 5/071* | (2010.01) |
| *C12M 3/00* | (2006.01) |
| *C12M 3/06* | (2006.01) |

(52) U.S. Cl.
CPC ........... *C12N 5/0682* (2013.01); *C12M 21/08* (2013.01); *C12M 23/16* (2013.01); *C12N 2501/11* (2013.01); *C12N 2501/31* (2013.01); *C12N 2502/243* (2013.01); *C12N 2513/00* (2013.01); *C12N 2533/74* (2013.01)

(58) Field of Classification Search
CPC ............ C12N 5/0682; C12N 2502/243; C12N 2513/00; C12M 21/08; C12M 23/16
See application file for complete search history.

(56) References Cited

PUBLICATIONS

Huh et al., From three-dimensional cell culture to organs-on-chips. Trends in Cell Biology, vol. 21, No. 12 (Dec. 2011) pp. 745-754.*
Laronda et al., Recreating the female reproductive tract in vitro using iPSC technology in a linked microfluidics environment. Stem Cell Research & Therapy, vol. 4, Supp. 1 (2013) pp. S13-S17.*
Thuenauer et al., Microfluidic approaches for epithelial cell layer culture and characterisation. Royal Society of Chemistry, vol. 139 (online Feb. 26, 2014) pp. 3206-3218.*

(Continued)

*Primary Examiner* — Kara Johnson
(74) *Attorney, Agent, or Firm* — Casimir Jones SC; David W. Staple

(57) ABSTRACT

The present invention relates generally to a three-dimensional cell and tissue culture system for the female reproductive tract. In particular provided herein the system includes individual female reproductive cultures in a dynamic microfluidic setting or integrated using a microfluidic microphysiologic system. In some embodiments, the present invention provides ex-vivo female reproductive tract integration in a three dimensional (3D) microphysiologic system.

21 Claims, 53 Drawing Sheets

(56) References Cited

PUBLICATIONS

Xu et al., Tissue-engineered follicles produce live, fertile offspring. Tissue engineering, vol. 12, No. 10 (Oct. 2006) pp. 2739-2746.*

Yamanouchi et al., Reconstruction of oviduct and demonstration of epithelial fat determination in mice. Biology of Reproduction, vol. 82, No. 3 (2010) pp. 528-533.*

Abe et al., Ultrastructural features of goat oviductal secretory cells at follicular and luteal phases of the oestrous cycle. Journal of anatomy 195 (Pt 4),515 (Nov. 1999).

Abir et al., Pilot study of isolated early human follicles cultured in collagen gels for 24 hours. Human reproduction 14, 1299 (May 1999).

Ahn et al., Nano-encapsulation of arsenic trioxide enhances efficacy against murine lymphoma model while minimizing its impact on ovarian reserve in vitro and in vivo. PloS one, 2013, 8:e58491.

Albertini et al., Cellular basis for paracrine regulation of ovarian follicle development. Reproduction, 2001, 121:647-653.

Allan et al., Impact of the deepwater horizon oil spill on bioavailable polycyclic aromatic hydrocarbons in gulf of mexico coastal waters. Environmental science & technology, 2012, 46:2033-2039.

Baursachs et al., Monitoring gene expression changes in bovine oviduct epithelial cells during the oestrous cycle. Journal ofmolecular endocrinology 32, ~49 (Apr. 2004).

Biggers et al., The pattern of energy metabolism in the mouse oocyte and zygote. Proceedings of the National Academy of Sciences of the United States of America, 1967, 58:560-567.

Borovskaya et al., Morphological and functional state of rat ovaries in early and late periods after administration of platinum cytostatics. Bulletin of experimental biology and medicine, 2004, 137:331-335.

Burkart et al., Repression of the inhibin alpha-subunit gene by the transcription factor CCAAT/enhancer-binding protein-beta. Endocrinology 146, 1909 (Apr. 2005).

Bylander et al., Rapid effects of progesterone on ciliary beat frequency in the mouse fallopian tube. Reproductive biology and endocrinology: RB&E 8,48 (2010).

Cole et al., The nematode caenorhabditis elegans as a model of organophosphate-induced mammalian neurotoxicity. Toxicology and applied pharmacology, 2004, 194:248-256.

Colonna et al., Mechanisms of amino acid uptake in cumulus-enclosed mouse oocytes. Biology of reproduction, 1983, 28:797-803.

Combelles et al., Hormonal control of somatic cell oocyte interactions during ovarian follicle development. Molecular reproduction and development, 2004, 69:347-355.

Cortvrindt et al., Follicle culture in reproductive toxicology: A tool for in-vitro testing of ovarian function? Human reproduction update, 2002, 8:243-254.

Craig et al., Di-n-butyl phthalate disrupts the expression of genes involved in cell cycle and apoptotic pathways in mouse ovarian antral follicles. Biology of reproduction, 2013, 88:23.

Croxatto, Physiology of gamete and embryo transport through the fallopian tube. Reproductive biomedicine online 4, 160 (Mar.-Apr. 2002).

Ducibella et al., Competence to undergo normal, fertilization-induced cortical activation develops after metaphase i of meiosis in mouse oocytes. Developmental biology, 1994, 165:95-104.

Durlinger et al., Regulation of ovarian function: the role of anti-Mullerian hormone. Reproduction, 2002, 124:601.

Eddie et al., Three-dimensional modeling of the human fallopian tube fimbriae Gynecol Oncol. Feb. 2015;136(2):348-54.

Eppig et al., Mouse oocytes regulate metabolic cooperativity between granulosa cells and oocytes: Amino acid transport. Biology of reproduction, 2005, 73:351-357.

Erickson-Lawrence et al., Oliphant Effect of steroid hormones on sulfated oviductal glycoprotein secretion by oviductal explants in vitro. Biol Reprod. Jun. 1989;40(6):1311-9.

Fortune et al., Follicular development: the role of the follicular microenvironment in selection of the dominant follicle. Anim Reprod Sci. Jul. 2004;82-83:109-26.

Ge et al., Activin-like peptides in somatotrophs and activin stimulation of growth hormone release in goldfish. Gen Comp Endocrinol. Aug. 1994;95(2):213-21.

Gennari et al., Aromatase activity and bone loss. Adv Clin Chem. 2011;54:129-64.

Goodbody-Gringley et al., Toxicity of deepwater horizon source oil and the chemical dispersant, corexit(r) 9500, to coral larvae. PLoS One. 2013;8(1):e45574.

Hay et al., Distribution of delta-5-3beta-hydroxysteroid dehydrogenase activity in the Graafian follicle of the sheep. J Reprod Fertil. May 1975;43(2):313-22.

Hedin et al., Changes in content of cytochrome P450(17)alpha, cytochrome P450scc, and 3-hydroxy-3-methylglutaryl CoA reductase in developing rat ovarian follicles and corpora lutea: correlation with theca cell steroidogenesis. Biology of reproduction, Biol Reprod. Aug. 1987;37(1):211-23.

Hemmer et al., Comparative toxicity of eight oil dispersants, louisiana sweet crude oil (lsc), and chemically dispersed lsc to two aquatic test species. Environ Toxicol Chem. Oct. 2011;30(10):2244-52.

Holland et al., Testosterone levels and cognition in elderly men: A review. Maturitas. Aug. 2011;69(4):322-37.

Hook et al., Comparison of toxicity and transcriptomic profiles in a diatom exposed to oil, dispersants, dispersed oil. Aquat Toxicol. Nov. 15, 2012;124-125:139-51.

Hunter, The Fallopian tubes in domestic mammals: how vital is theirphysiological activity? Reprod Nutr Dev. May-Jun. 2005;45(3):281-90.

Kenney et al., High risk of infertility and long term gonadal damage in males treated with high dose cyclophosphamide for sarcoma during childhood. Cancer. Feb. 1, 2001;91(3):613-21.

Klein et al., Age-related analysis of inhibin A, inhibin B, and activin a relative to the intercycle monotropic follicle-stimulating hormone rise in normal ovulatory women. J Clin Endocrinol Metab. Jun. 2004;89(6):2977-81.

Kociba et al., Acute toxicologic and pathologic effects of cis-diamminedichloroplatinum (nsc-119875) in the male rat. Cancer Chemother Rep. Feb. 1971;55(1):1-8.

Lenie et al., Continuous exposure to bisphenol a during in vitro follicular development induces meiotic abnormalities. Mutat Res. Mar. 12, 2008;651(1-2):71-81.

Livak et al., Analysis of relative gene expression data using real-time quantitative PCR and the 2(-Delta Delta C(T)) Method. Methods. Dec. 2001;25(4):402-8.

MacNaughton et al., Age related changes in follicle stimulating hormone, luteinizing hormone, oestradiol and immunoreactive inhibin in women of reproductive age. Clin Endocrinol (Oxf). Apr. 1992;36(4):339-45.

Mahmood et al., The effect of ovarian steroids on epithelial ciliary beat frequency in the human Fallopian tube. Hum Reprod. Nov. 1998;13(11):2991-4.

McGee et al., Initial and cyclic recruitment of ovarian follicles. Endocr Rev. Apr. 2000;21(2):200-14.

Meirow et al., Subclinical depletion of primordial follicular reserve in mice treated with cyclophosphamide: Clinical importance and proposed accurate investigative tool. Hum Reprod. Jul. 1999;14(7):1903-7.

Meirow et al., The effects of radiotherapy and chemotherapy on female reproduction. Hum Reprod Update. Nov.-Dec. 2001;7(6):535-43.

Nakahari et al., The regulation of ciliary beat frequency by ovarian steroids in the guinea pig Fallopian tube: interactions between oestradiol and progesterone. Biomed Res. Oct. 2011;32(5):321-8.

NIOSH (National Insittute for Occupational Safety and Health), Health hazard evaluation of deepwater horizon response workers., Aug. 2011, http://www.cdc.gov/niosh/hhe/reports/pdfs/2010-0115-0129-3138.pdf, retrieved Apr. 18, 2016, 24 pages.

Pappa et al., Endogenous sex steroids and cardio- and cerebro-vascular disease in the postmenopausal period. Eur J Endocrinol. Aug. 2012;167(2):145-56.

(56) References Cited

OTHER PUBLICATIONS

Parker et al., Plasma concentrations of inhibin a and follicle-stimulating hormone differ between cows with two or three waves of ovarian follicular development in a single estrous cycle. Biol Reprod. Mar. 2003;68(3):822-8.
Pedersen et al., Proposal for a classification of oocytes and follicles in the mouse ovary. J Reprod Fertil. Dec. 1968;17(3):555-7.
Picton et al., The in vitro growth and maturation of follicles. Reproduction. Dec. 2008;136(6):703-15.
Plancha et al., Cell polarity during folliculogenesis and oogenesis. Reprod Biomed Online. Apr. 2005;10(4):478-84.
Roh et al., Ecotoxicological investigation of ceo(2) and tio(2) nanoparticles on the soil nematode caenorhabditis elegans using gene expression, growth, fertility, and survival as endpoints. Environ Toxicol Pharmacol. Mar. 2010;29(2):167-72.
Ronen-Fuhrmann et al., Spatio-temporal expression patterns of steroidogenic acute regulatory protein (StAR) during follicular development in the rat ovary. Endocrinology. Jan. 1998;139(1):303-15.
Sato et al., Expression of Idl receptor and uptake of Idl in mouse preimplantation embryos. Mol Cell Endocrinol. Apr. 28, 2003;202(1-2):191-4.
Shikanov et al., Interpenetrating fibrin-alginate matrices for in vitro ovarian follicle development. Biomaterials. Oct. 2009;30(29):5476-85.
Sklar, Maintenance of ovarian function and risk of premature menopause related to cancer treatment. J Natl Cancer Inst Monogr. 2005;(34):25-7.
Sochova et al., Effects of seven organic pollutants on soil nematode caenorhabditis elegans. Environ Int. Aug. 2007;33(6):798-804.
Spielmann, Reproduction and development. Environ Health Perspect. Apr. 1998;106 Suppl 2:571-6.
Su et al., Mouse oocytes enable Ih-induced maturation of the cumulus-oocyte complex via promoting egf receptor-dependent signaling. Mol Endocrinol. Jun. 2010;24(6):1230-9.
Su et al., Oocyte regulation of metabolic cooperativity between mouse cumulus cells and oocytes: Bmp15 and gdf9 control cholesterol biosynthesis in cumulus cells. Development. Jan. 2008;135(1):111-21.
Sugiura et al., Oocyte-derived bmp15 and fgfs cooperate to promote glycolysis in cumulus cells. Biol Reprod. Nov. 2009;81(5):833-41.
Sugiura et al., Fibroblast growth factors and epidermal growth factor cooperate with oocyte-derived members of the tgfbeta superfamily to regulate spry2 mrna levels in mouse cumulus cells. Biology of reproduction 81:833-841.
Sugiura et al., Estrogen promotes the development of mouse cumulus cells in coordination with oocyte-derived gdf9 and bmp15. Mol Endocrinol. Dec. 2010;24(12):2303-14.
Sun et al., Preantral follicle culture as a novel in vitro assay in reproductive toxicology testing in mammalian oocytes. Mutagenesis. Jan. 2004;19(1):13-25.
Talbot et al, Cell adhesion and fertilization: steps in oocyte transport, sperm-zona pellucida interactions, and sperm-egg fusion. Biol Reprod. Jan. 2003;68(1):1-9.
The National Academy of Sciences. 2007. Toxicity testing in the 21st century: A vision and a strategy. Available: http://dels.nas.edu/best [accessed Mar. 12, 2013].
Tingen et al., A macrophage and theca cell-enriched stromal cell population influences growth and survival of immature murine follicles in vitro. Reproduction. Jun. 2011;141(6):809-20.
Trigatti et al., Influence of the high density lipoprotein receptor sr-bi on reproductive and cardiovascular pathophysiology. Proc Natl Acad Sci U S A. Aug. 3, 1999;96(16):9322-7.
U.S. Environmental Protection Agency, Guidelines for reproductive toxicity risk assessment, Oct. 31, 1996, https://www.epa.gov/sites/production/files/2014-11/documents/guidelines_repro_toxicity.pdf, retrieved Apr. 19, 2016, Federal Register 61(212):56274-56322, 143 pages.
Van Wemmel et al., Ovarian follicle bioassay reveals adverse effects of diazepam exposure upon follicle development and oocyte quality. Reprod Toxicol. Jul.-Aug. 2005;20(2):183-93.
Velasquez et al., PAF receptor and PAF acetylhydrolase expression in the endosalpinx of the human Fallopian tube: possible role of embryo-derived PAF in the control of embryo transport to the uterus. Hum Reprod. Aug. 2001;16(8):1583-7.
Wallace et al., Gonadal dysfunction due to cis-platinum. Med Pediatr Oncol. 1989;17(5):409-13.
Wang et al., Assessment of locomotion behavioral defects induced by acute toxicity from heavy metal exposure in nematode caenorhabditis elegans. J Environ Sci (China). 2008;20(9):1132-7.
Wang et al., Mono-(2-ethylhexyl) phthalate induces oxidative stress and inhibits growth of mouse ovarian antral follicles. Biol Reprod. Dec. 27, 2012;87(6):152.
Weenen et al., Anti-Mullerian hormone expression pattern in the human ovary: potential implications for initial and cyclic follicle recruitment. Mol Hum Reprod. Feb. 2004;10(2):77-83.
Welt et al., Control of follicle-stimulating hormone by estradiol and the inhibins: critical role of estradiol at the hypothalamus during the luteal-follicular transition. J Clin Endocrinol Metab. Apr. 2003;88(4):1766-71.
West-Farrell et al., The mouse follicle microenvironment regulates antrum formation and steroid production: Alterations in gene expression profiles. Biol Reprod. Mar. 2009;80(3):432-9.
Xu et al., Encapsulated three-dimensional culture supports development of nonhuman primate secondary follicles. Biol Reprod. Sep. 2009;81(3):587-94.
Xu et al., In vitro grown human ovarian follicles from cancer patients support oocyte growth. Hum Reprod. Oct. 2009;24(10):2531-40.
Xu et al., Secondary follicle growth and oocyte maturation by culture in alginate hydrogel following cryopreservation of the ovary or individual follicles. Biotechnol Bioeng. Jun. 1, 2009;103(2):378-86.
Xu et al., In vitro oocyte maturation and preantral follicle culture from the luteal-phase baboon ovary produce mature oocytes. Biol Reprod. Apr. 2011;84(4):689-97.
Yanulevich, Outpatient anesthesia with nalbuphine hydrochloride. AANA J. Aug. 1983;51(4):395-7.
Yeh et al., Mullerian inhibiting substance as a novel biomarker of cisplatin-induced ovarian damage. Biochem Biophys Res Commun. Sep. 22, 2006;348(2):337-44.
Yucebilgin et al., Effect of chemotherapy on primordial follicular reserve of rat: An animal model of premature ovarian failure and infertility. Aust N Z J Obstet Gynaecol. Feb. 2004;44(1):6-9.
Zeleznik, The physiology of follicle selection. Reprod Biol Endocrinol. Jun. 16, 2004;2:31.
Zhang et al., Chemical dispersant potentiates crude oil impacts on growth, reproduction, and gene expression in caenorhabditis elegans. Arch Toxicol. Feb. 2013;87(2):371-82.

* cited by examiner

A

B

C

A

B

Endometrium in 3D

Myometrium in 3D

Vimentin        PR        DAPI

Myometrium
H & E Staining

Myometrium
DAPI Staining

20x

Follicles Retrieved After
Microfluidic Culture

3D MICROPHYSIOLOGIC SYSTEM

CROSS REFERENCE TO RELATED APPLICATIONS

The present application claims the benefit of U.S. Provisional Patent Application Ser. No. 61/932,592, filed Jan. 28, 2014, which is incorporated by reference in its entirety.

STATEMENT REGARDING FEDERAL FUNDING

This invention was made with government support under ES022920 awarded by the National Institutes of Health. The government has certain rights in the invention.

FIELD

The present invention relates generally to a three-dimensional cell and tissue culture systems for the female reproductive tract. In particular provided herein are the system includes individual female reproductive cultures integrated using a microfluidic microphysiologic system.

BACKGROUND

The main organs of reproductive tract include the ovary, fallopian tubes, uterus, cervix, and vagina. These organs function in relation to one another to provide hormonal support or the anatomical structure through which gametes travel for the developing embryo to implant and develop. A robust three dimensional reproductive tract that is a physiologic mimic of the in vivo biology is what is needed.

SUMMARY

The present invention relates generally to a three-dimensional cell and tissue culture systems for the female reproductive tract. In particular, provided herein are systems comprising individual female reproductive cultures integrated using a microfluidic microphysiologic system. In some embodiments, the present invention provides ex-vivo female reproductive tract integration in a three dimensional (3D) microphysiologic system.

In some embodiments, provided herein are microphysiologic systems (e.g., systems that simulate one or more aspects of the human reproductive tract) comprising: (a) a first 3D cell culture subsystem comprising at least a first cell type in 3D culture and a culture media for said first cell type; and (b)

a second 3D cell culture subsystem comprising at least a second cell type in 3D culture and a culture media for said second cell type; wherein the first 3D cell culture subsystem and the second 3D cell culture subsystem are in unidirectional fluid communication such that factors secreted from said first cell type flow downstream to the second 3D cell culture subsystem. In some embodiments, microphysiologic systems further comprise one or more additional 3D cell culture subsystems, each comprising at least one additional and distinct cell type in 3D culture and a culture media for said additional cell type. In some embodiments, microphysiologic systems further comprise a third 3D cell culture subsystem comprising at least a third cell type in 3D culture and a culture media for said third cell type; wherein the second 3D cell culture subsystem and the third 3D cell culture subsystem are in unidirectional fluid communication such that factors secreted from said second cell type and/or said first cell type flow downstream to the third 3D cell culture subsystem. microphysiologic systems further comprise a fourth 3D cell culture subsystem comprising at least a fourth cell type in 3D culture and a culture media for said fourth cell type; wherein the third 3D cell culture subsystem and the fourth 3D cell culture subsystem are in unidirectional fluid communication such that factors secreted from said third cell type, said second cell type, and/or said first cell type flow downstream to the fourth 3D cell culture subsystem. In some embodiments, microphysiologic systems further comprise a fifth 3D cell culture subsystem comprising at least a fifth cell type in 3D culture and a culture media for said fifth cell type; wherein the fourth 3D cell culture subsystem and the fifth 3D cell culture subsystem are in unidirectional fluid communication such that factors secreted from said fourth cell type, said third cell type, said second cell type, and/or said first cell type flow downstream to the fourth 3D cell culture subsystem. In some embodiments, the first 3D cell culture subsystem comprises an ovarian follicle 3D cell culture subsystem, wherein the second 3D cell culture subsystem comprises a fallopian tube 3D cell culture subsystem, wherein the third 3D cell culture subsystem comprises a uterine 3D cell culture subsystem, wherein the fourth 3D cell culture subsystem comprises an endocervical 3D cell culture subsystem, and wherein the fifth 3D cell culture subsystem comprises an ectocervical 3D cell culture subsystem. In some embodiments, the ovarian follicle 3D cell culture subsystem comprises one or more of granulosa cells, theca cells, and oocytes. In some embodiments, the fallopian tube 3D cell culture subsystem comprises one or more of secretory epithelial cells, ciliated epithelial cells, and fallopian stromal cells. In some embodiments, the uterine 3D cell culture subsystem comprises one or more of endometrial epithelial cells, endometrial stromal cells, myometrial smooth muscle cells, and myometrial stromal cells. In some embodiments, the endocervical 3D cell culture subsystem comprises one or both of endocervical epithelial cells and endocervical stromal cells. In some embodiments, the ectocervical 3D cell culture subsystem comprises one or both of ectocervical epithelial cells, J2-3T3 fibroblasts, and ectocervical stromal cells. In some embodiments, the microphysiologic system comprises human or murine cells. In some embodiments, the ovarian follicle 3D cell culture subsystem comprises one or more ovarian follicles in 3D culture. In some embodiments, the ovarian follicles are polymer-encapsulated or hydrogel-encapsulated. In some embodiments, the polymer or hydrogel comprises alginate. In some embodiments, the ovarian follicles (or other cultured cells or tissues) are encapsulated or supported by a matrix or support material. Suitable matrices and/or support materials may include, but are not limited to alginate, polyethylene glycol, poly(octanediol citrate), decellularized matrix (e.g., general or specific), fibroblast-derived native matrix, collagen, matrigel, hyaluronan, laminin, entactin, tenascin, fibronectin, poly-1-lysine, fibrin, polystyrene scaffold (e.g., ALVETEX), etc. In some embodiments, the ovarian follicles remain viable for at least one simulated menstrual cycle. In some embodiments, the ovarian follicles respond to FSH and hCG stimulation by producing estrogen and progesterone in a pattern that mimics the human menstrual cycle. In some embodiments, estrogen and progesterone pass by unidirectional fluid communication to the fallopian tube 3D cell culture subsystem (e.g., from the ovarian follicle 3D cell culture subsystem). In some embodiments, the cells of the fallopian tube 3D tissue culture subsystem respond to said estrogen and/or progesterone with one or more of cilliary beating, OVGP1 expression, and/or IGF1 secretion. In some embodiments, the fallopian tube 3D tissue culture subsystem comprises fallopian epithelium tissue pieces grown on TRANSWELL inserts. In some embodiments, the fallopian tube system remains viable and maintains both secretory and ciliated epithelium cell phenotypes for at least one simulated menstrual cycle. In some embodiments, systems (and/or subsystems) comprise a microfluidic system that provides said unidirectional fluid communication.

In other embodiments, one or more pairs of subsystems are in bidirectional fluid communication. In some embodiments, additional fluids (e.g., media, comprising test compounds, etc.) are mixed with the fluid within the system at one or more positions in the system.

In some embodiments, the female-reproductive-tract-simulating-systems further comprise or are integrated with (e.g., in fluid communication with) cultures (e.g., 3D cultures) of related or non-reproductive cells or tissues. Suitable cells or tissues may include, but are not limited to those from liver, lung, breast, skin, eye, adipose, bone, blood vessel, myometrium, endometrium, placenta, etc. In some embodiments, cultures comprising such cells/tissues are in fluid communication (e.g., bidirectional, unidirectional, continuous, with mixing, without mixing, etc.) with one or more of the other subsystems described herein. In some embodiments, methods of assessing the impact of these cells/tissues on reproductive cells/tissues and/or the menstrual cycle are provided. In some embodiments, methods are provided of assessing the impact of reproductive cells/tissues and/or the menstrual cycle on these cells/tissues.

In some embodiments, systems described herein further comprise cultures (e.g., 3D culture) comprising one or more types of diseased cells or tissues. Diseased cells or tissues may be included in one of the subsystems described herein (e.g., ovarian, fallopian, uterine, endocervical, ectocervical, etc.) or may be provided as an addition subsystem integrated with (e.g., in fluid communication with) one of the subsystems described herein. Exemplary disease cells/tissues include those derived from uterine fibroid tissue, cancer tissue (e.g., ovarian, uterine, cervical, breast, liver, etc.), endometiotic tissue, pelvic inflammatory disease tissue, polycystic ovarian tissue, virally infected tissue (e.g., ectocervix barrier function-disease transmission), various microbiomes, etc.

In some embodiments, cultured cells/tissues are derived from induced pluripotent stem cells (iPSCs). In some embodiments, two or more of the subsystems comprise tissue/cells derived from the iPSCs from a subject. In some embodiments, such a system is used to assess the effects of various agents (e.g., drugs, chemotherapeutics, allergens, environmental toxins, etc.) on that subject. In some embodiments, personalized medicine methods are provided by screening therapies via the systems and methods described herein before administering to a subject.

In some embodiments, the systems and methods described herein are used to simulate the female reproductive tract during particular states, for example: pregnancy (e.g., comprising cultures of myometrium, endometrium, placenta, etc.; under appropriate hormone exposure; etc.), cancer or other diseases, during exposure to various agents (e.g., hormones, chemotherapeutics or other drugs, environmental toxins), normal menstrual cycle, irregular cycles, etc.

In some embodiments, effects of various stimuli on the human-female-simulating systems described herein are compared to one or more of: a human subject (e.g., a human female, a human male), another simulation of human biology, a simulation of the male reproductive system.

The present invention relates generally to a human female reproductive tract using individual three-dimensional tissue culture systems designed for integration using a microfluidic microphysiologic system (FemKube). In certain embodiments, the system includes individual three dimensional cultures of ovarian follicles (OvaryKube), fallopian tube (TubeKube), uterus (UteroKube), and cervix (CerviKube). In other embodiments, three dimensional cultures for the ectocervix and endocervix are provided rather than a single cervix culture. In some embodiments, the culters are in fluid communication, such that hormones and other molecular components of the system can pass (e.g., bidirectionally, unidirectionally, continually, with mixing, without mixing, etc.) between cultures. Importantly, each tissue remains viable for at least 28 days and responds to hormonal fluctuations that mimic the human menstrual cycle. Prior 3D culture systems for female reproductive tract either did not exist, used non-human cells, or were not relevant to long-term (e.g., full menstrual cycle) physiologic processes. In particular embodiments, systems described herein use hormones secreted by the 3D cultured ovarian follicles to stimulate the other reproductive tissues rather than adding, for example, exogenous hormones to the cell culture media.

The present invention describes a system comprised of multiple (e.g. 2, 3, 4, 5, 6, 7, 8, or more) individual female reproductive three-dimensional cultures integrating the tissues using a microfluidic microphysiologic system (or other integrative system that allows fluid and/or analyte exchange between cultures). In certain embodiments, the individual cultures are ovarian follicles, fallopian tube, uterus, and cervix. In other embodiments, the individual cultures are ovarian follicles, fallopian tube, uterus, endocervix, and ectocervix.

In some embodiments, the ovarian culture system uses, for example, human or murine follicles (e.g., encapsulated in alginate or other polymer). The follicles may be encapsulated in a substrate, matrix, polymer, etc. or may be unencapsulated. The (encapsulated) follicles remain viable long term (e.g., one menstrual cycle (e.g., 28 days), more than one menstrual cycle (e.g., 30-50 days), two menstrual cycles (e.g., 56 days), more than two menstrual cycles (e.g., >56 days), etc.). The follicles of the ovarian culture system respond to signals found in in vivo ovarian systems (e.g., follicle stimulating hormone (FSH) and human chorionic growth hormone (hCG, etc.). In some embodiments, the follicles undergo in-vitro maturation. In some embodiments, the follicles produce estrogen and progesterone in a pattern that mimics the human menstrual cycle. In certain embodiments, the fallopian tube system uses human fallopian epithelium tissue pieces grown on TRANSWELL inserts. Tissue remains viable for 28 days and maintains both secretory and ciliated epithelium cell phenotypes. Furthermore, the fallopian epithelium functionally responds to estrogen and progesterone using secreted factors and cilia beating as markers. The uterine system is comprised of human endometrial epithelial, endometrial stromal, and myometrial cells. In certain embodiments, the endometrial epithelial and stromal cells are isolated separately and combined for culture on TRANSWELL inserts, while myomertial smooth muscle cells are cultured on a separate TRANSWELL insert. In some embodiments, the endometrial and myometrial inserts are cultured in the same tissue culture well in a common media. In some embodiments, uterine cultures are viable for at least 28 days. In some embodiments, cervical cultures are comprised of primary human endocervical epithelial and stromal cells (e.g., grown on the same TRANSWELL insert). In some embodiments, endocervix remains viable for at least 28 days and responds to estrogen and progesterone mimicking the human menstrual cycle.

In some embodiments of the invention, the organ culture system is used to screen therapeutic compositions, to assess efficacy of a pharmaceutical composition, to assess pharmaceutical toxicity, to assess toxicity of non-pharmaceutical compositions, to assess toxicity of environmental contaminants, to assess contraceptive compositions and methods, for reproductive biology studies, to study normal female reproductive tract biology, to study diseased female reproductive tract biology, to study the female menstrual cycle, etc.

In some embodiments, provided herein is the use of systems and subsystems described herein for testing the efficacy and/or toxicity of the pharmaceutical composition.

In some embodiments, provided herein is the use of systems and subsystems described herein for testing the effects of various agents on one or more tissues (e.g., the entire reproductive tract). Suitable agents may comprise environmental toxins, pharmaceuticals (e.g., chemotherapeutics, birth control, etc.), hormones, etc. Exemplary agents include, but are not limited to: estradiol, ulipristal acetate, RU486, insulin, diethylstibestrol (DES), corexit 9500, medroxyprogesterone acetate (MPA), follicle-stimulating hormone (FSH), human chorionic gonadotropin (hCG), progesterone, bisphenol A (BPA), testosterone, cisplatin, nalbuphine, raclopride, arsenic trioxide, nonoxynol-9, vitamin A, vitamin D, nicotine, glucose (e.g., to mimic a diabetic state), caffeine, cortisol (stress), soy (e.g., including genistein), ethanol, etc.

Although some embodiments are described herein as related to systems simulating the biological functions of the "human" female reproductive tract, the present invention is not so limited. In some embodiments, provided herein are microphysiologic systems that simulate one or more aspects of the reproductive tract of a non-human animal (e.g., rodent, non-human primate, feline, canine, bovine, equine, porcine, etc.).

In some embodiments, systems are provided comprising a single 3D culture (e.g., described elsewhere herein as a subsystem (e.g., ovarian follicles, fallopian tubes, uterus, endocervix, ectocervix, etc.) and microfluidics to provide a flow of media, hormones, factors, test agents, etc. In some embodiments, the microfluidics provides a flow media that simulates the upstream tissues. In some embodiments, flow from the culture is analyzed.

DEFINITIONS

As used herein the terms "3D culture," "3D cell culture," and 3D tissue culture" refer to artificial environments in which biological cells are permitted to grow and/or interact surroundings in all three dimensions. This is in contrast to traditional 2D culture in which cells are grown in a monolayer on a flat, two-dimensional surface, such as a petri dish. Environments for 3D culture include extracellular matrices, 3D scaffolds, polymer (e.g., alginate) encapsulation, bioreactors (e.g., rotating bioreactors), microcarriers, magnetic levitation systems, hanging drop, magnetic 3D bioprinting, etc.

DETAILED DESCRIPTION

The present invention relates generally to a three-dimensional cell and tissue culture system for the female reproductive tract. In particular provided herein the system includes individual female reproductive cultures integrated using a microfluidic microphysiologic system. In some embodiments, the present invention provides ex-vivo female reproductive tract integration in a three dimensional (3D) microphysiologic system. In particular embodiments, provided herein are ex vivo female reproductive tracts constructed using individual 3D tissue culture subsystems integrated into a microfluidic microphysiologic system (e.g., FemKube). In some embodiments, the system includes individual 3D cultures of one or more of ovarian follicles (e.g., OvaryKube), fallopian tube (e.g., TubeKube), uterus (e.g., UteroKube), and cervix (e.g., CerviKube). In some embodiments, the cervix is divided into separate endocervix and ectocervix cultures. In some embodiments, each tissue remains viable for at least one menstrual cycle (e.g., 28 days for humans) and responds to hormonal fluctuations that mimic the menstrual cycle (e.g., human menstrual cycle).

3D culture systems for the female reproductive tract do not exist using human cells that are relevant and/or useful of the time scale relevant to long term physiologic processes (e.g., menstrual cycle). In some embodiments, the systems provided herein utilize hormones secreted by 3D cultured ovarian follicles to stimulate other downstream reproductive tissues rather than adding exogenous hormones to the cell culture media. In some embodiments, a series of 3D culture subsystems are in fluid communication such that each subsequent subsystem reacts to the hormones and other factors released by the upstream subsystems (e.g., the subsystem immediately upstream, all subsystems upstream, etc.). In some embodiments, flow between subsystems is regulated (e.g., by microfluidics) in such a manner as to allow the appropriate level of secreted hormones and other factors to pass one or more subsequent subsystems. In some embodiments, the relative volume of subsystems is selected to allow the appropriate level of secreted hormones and other factors to pass one or more subsequent subsystems.

Figure 21:
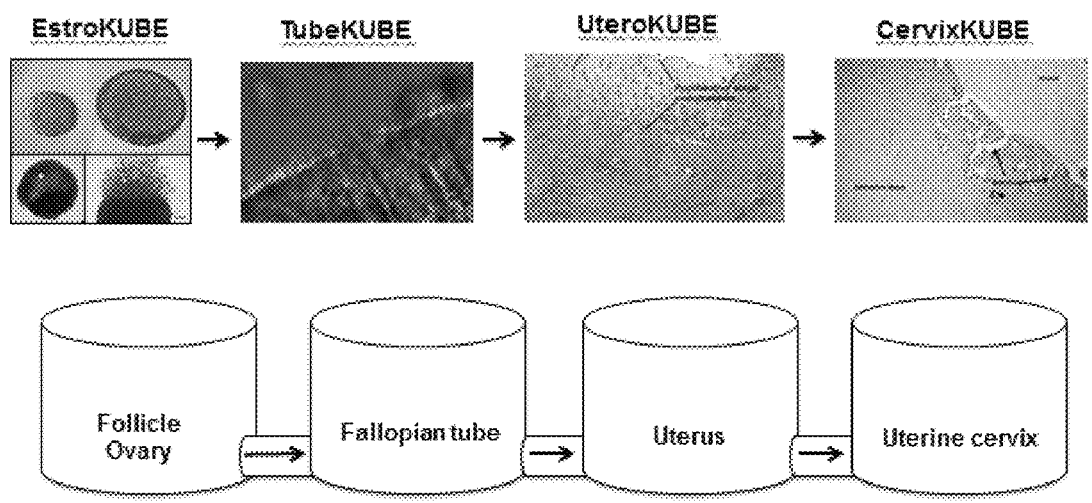
FIG. 21. Images of various cells in the culture subsystems described herein (top), and a schematic depicting an exemplary flow of secreted factors from upstream tissues to downstream tissues.

In some embodiments, a system comprises multiple culture subsystems in fluid communication (e.g., bidirectional, unidirectional, continuous, with mixing, without mixing, etc.). For example, unidirectional fluid communication allows downstream tissues to respond to factors secreted by upstream tissues in real time to establish a system that mimics the dynamic female reproductive tract ex vivo (See, e.g., FIG. 21). In some embodiments, subsystems are connected in series (e.g., as depicted in FIG. 21). In other embodiments, two or more subsystems are connected in parallel (e.g., downstream and upstream from the same subsystems). In some embodiments, two or more subsystems are connected in semi-parallel (e.g., downstream or upstream from the same subsystems, but in series with one or more other subsystems).

Figure 23:
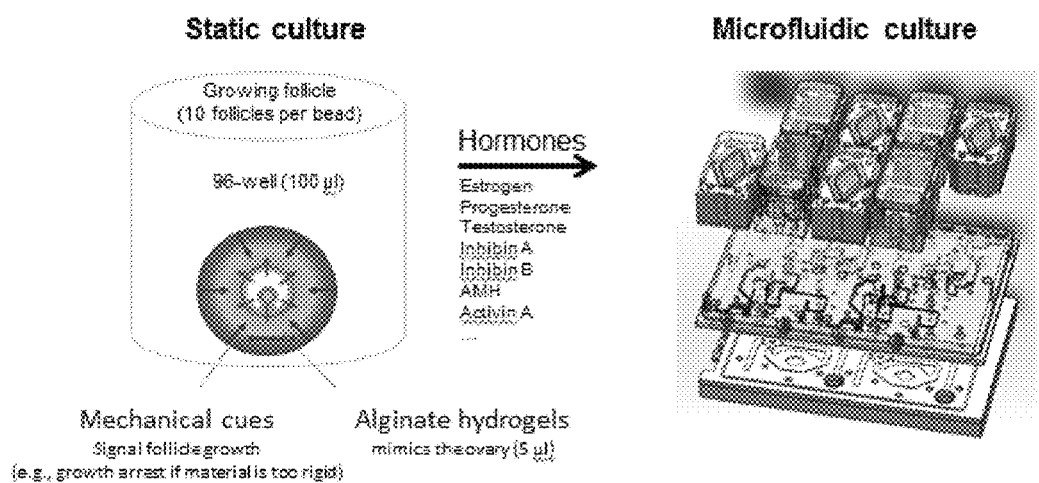

In some embodiments, dynamic culture allows for the transfer of factors from one culture subsystem to another, thereby recapitulating the transfer of factors within complex body systems. Multiple static cultures in which the necessary factors are added by a user or automated system are translated into dynamic systems in which the cells/tissues are able to communicate as they do in vivo, with real-time transfer (e.g., downstream delivery) of hormones and other factors between tissues (FIG. 23).

A microphysiologic system, containing living cell tissue constructs interconnected by microfluidic channels is described, for example, in U.S. Pat. No. 7,288,405; herein incorporated by reference in its entirety. In some embodiments, the systems described herein permit cells to be maintained in vitro, under conditions similar to those found in vivo. Parameters accurately simulated by the system include, for example, interactions between cells, liquid residence time, liquid to cell ratios, relative size, metabolism by cells, shear stress, and the like. In some embodiments, systems mimic the natural state of cells, the predictive value of assays performed therewith. In some embodiments, a microfluidic network of channels connect segregated, discrete chambers. In some embodiments, chamber geometry and connectivity is designed to provide cellular interactions, liquid flow, and liquid residence parameters that correlate with those found for the corresponding cells, tissues, or organs in vivo.

In some embodiments, microphysiologic systems find use in, for example, pharmaceutical and toxicology testing for effects on the reproductive tract (e.g., without using animals), contraception and/or hormone testing, reproductive biology studies of normal and/or diseased tissues. Systems described herein have numerous advantages, including but not limited to, the use of primary human tissues rather than animal tissues or cell lines, they maintain viability and/or hormonal response over the length of the normal (human) menstrual cycle, they provide the ability to use 3D cultured ovarian follicles as hormone source for other 3D cultured tissues to mimic human menstrual cycle.

In some embodiments, a system comprises multiple individual female reproductive 3D cultures (e.g., two, three, four, five, six, or more). In some embodiments, the separate 3D cultures (e.g., subsystems) are integrated using a microfluidic microphysiologic system. The individual cultures are, for example, ovarian follicles, fallopian tube, uterus, and cervix (e.g., endocervix and ectocervix. In some embodiments, the ovarian culture subsystem uses either human or murine follicles encapsulated in polymer (e.g., collagen, alginate, poly (octanediol citrate), etc.). In some embodiments, the encapsulated follicles remain viable long term (e.g., 28+ days). In some embodiments, the encapsulated follicles respond to follicle stimulating hormone (FSH) and human chorionic gonadotropin (hCG) in-vitro follicle maturation by producing estrogen and progesterone in a pattern that mimics the human menstrual cycle. In some embodiments, the fallopian tube subsystem uses human fallopian epithelium tissue pieces grown, for example, on TRANSWELL inserts. Tissue remains viable for 28 or more days and maintains both secretory and ciliated epithelium cell phenotypes. In some embodiments, the fallopian epithelium functionally responds to estrogen and progesterone using secreted factors and cilia beating as markers. The uterine subsystem is comprised of human endometrial epithelial, endometrial stromal, and myometrial cells. In some embodiments, the endometrial epithelial and stromal cells are isolated separately and combined for culture on TRANSWELL inserts, while myometrial smooth muscle cells are cultured on a separate TRANSWELL insert. In some embodiments, the endometrial and myometrial inserts are cultured in the same tissue culture well in a common media. Uterine cultures are viable for at least 28 days. In some embodiments, cervical cultures are comprised of primary human endocervical epithelial and stromal cells grown on the same TRANSWELL insert. Endocervix remains viable for at least 28 days and responds to estrogen and progesterone mimicking the human menstrual cycle.

Provided herein is a multi-component culture system comprised of multiple culture subsystems, wherein each of the culture subsystems is in fluid communication (e.g., bidirectional, unidirectional, continuous, with mixing, without mixing, etc.) with at least one of the other subsystems. In some embodiments, appropriate culture conditions are provided for each culture subsystem (e.g., media, temperature, etc.).

In some embodiments, culture media is changed regularly (e.g., hourly, four-times daily, twice daily, daily, etc.). In some embodiments, culture media is continuously replenished. In some embodiments, the flow of media, reagents, and other chemicals (e.g., hormones) between the subsystems renders one or more subsystems and/or the entire system self-replenishing. In some embodiments, culture is carried out at between 18° C. and 40° C. (e.g., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C. or ranges therein). In some embodiments, culture is carried out at room temperature (e.g., 18° C., 19° C., 20° C., 21° C., 22° C., 23° C., 24° C., or ranges therein). In some embodiments, culture is carried out at human physiologic temperature (e.g., about 37° C.). In some embodiments, reagents used in culture media are sterilized. In some embodiments, devices (e.g., chambers, vessels, bottles, flasks, tubes, etc.) used in culturing are sterilized.

In some embodiments, appropriate devices are selected for containing cells and media in the various culturing subsystems. In some embodiments, Transwell plates or other permeable supports are provided. Transwell cell culture chambers, or Transwell plates (e.g., available from Costar Corp., Cambridge, Md., USA) are an example of a multi-chamber culture device in which media, nutrients, hormones, reagents, etc. may pass between the chambers, but cells may not. Each chamber of a Transwell plate comprises a flat-bottomed, open-topped, lower compartment with impermeable bottom and sides, and an open-topped, upper compartment with a microporous membrane which forms the bottom of the upper compartment. This assembly is typically covered by a removable lid. In use, cells (e.g., a first type of cells) are placed on the upper surface of the microporous membrane within the upper compartment. The upper compartment is inserted into the lower compartment. Due to the permeability of the membrane, media, nutrients, factors, etc. are able to traverse the membrane. Cells may also be placed in the upper chamber (e.g., a second type of cells). Other multi-chamber culture systems (e.g., two chambers, three chambers, four chambers, or more) may find use in embodiments described herein. Divisions between chambers may be permeable, semipermeable (e.g., with a particular molecular weight cutoff (e.g., permeable to small molecules, but not proteins), or impermeable.

In some embodiments, ovarian follicle culture media comprises one or more (e.g., all) of: alpha-MEM, DMEM F12, BSA, Fetuin, Insulin, Transferrin, Selenium, and FSH. In some embodiments, ovarian follicle culture media comprises one or more (e.g., all) of: alpha-MEM (e.g. 40-60%, 45-55%, about 50%, etc.), DMEM F12 (e.g. 40-60%, 45-55%, about 50%, etc.), BSA (1-5 mg/ml, 2-4 mg/ml, about 3 mg/ml, etc.), Fetuin (0.1-1 mg/ml, 0.3-0.7 mg/ml, about 0.5 mg/ml), Insulin (1-10 mg/ml, 3-7 mg/ml, about 5 mg/ml), Transferrin (1-10 mg/ml, 3-7 mg/ml, about 5 mg/ml), Selenium (1-10 ng/ml, 3-7 ng/ml, about 5 ng/ml), and FSH (e.g., 5-15 IU/ml, 8-12 IU/ml, about 10 IU/ml). In some embodiments, ovarian follicle culture media comprises one or more (e.g., all) of: 50% alpha-MEM, 50% DMEM F12, 3 mg/mL BSA, 0.5 mg/mL Fetuin, Insulin (5 ug/mL), Transferrin (5 ug/mL), Selenium (5 ng/mL), 10 IU/mL FSH. In some embodiments, during hCG treatment to trigger the luteal phase of the in-vitro menstrual cycle, the media is changed. In some embodiments, the luteal phase media comprises one or more (e.g., all) of: alpha-MEM, FBS, EGF, hCG, and FSH. In some embodiments, the luteal phase media comprises one or more of: alpha-MEM (e.g., 90-100%, about 100%, etc.), FBS (1-20%, 5-15%, 8-12%, about 10%, etc.), EGF (1-10 ng/ml, 3-7 ng/ml, about 5 ng/ml, etc.), hCG (0.5-2.5 IU/ml, 1.0-2.0 IU/ml, about 1.5 IU/ml, etc.), and FSH (5-15 IU/ml, 8-12 IU/ml, about 10 IU/ml, etc.). In some embodiments, the luteal phase media comprises one or more (e.g., all) of: 100% alpha-MEM, 10% FBS, EGF (5 ng/mL), hCG (1.5 IU/mL), FSH (10 IU/mL). In some embodiments, following hCG treatment (e.g., for 4-28 hours, 10-22 hours, 14-18 hours, about 16 hours), the second media is replaced with the first media formulation but with reduced FSH (e.g., without FSH).

In some embodiments, fallopian culture media comprises one or more (e.g., all) of: alpha MEM, BSA, Fetuin, Insulin, Transferrin, and Selenium. In some embodiments, fallopian culture media comprises one or more (e.g., all) of: alpha MEM, BSA (e.g., 1-5 mg/ml, 2-4 mg/ml, about 3 mg/ml, etc.), Fetuin (e.g., 0.1-1.0 mg/ml, 0.3-0.7 mg/ml, about 0.5 mg/mL, etc.), Insulin (e.g., 1-10 mg/ml, 3-7 mg/ml, about 5 mg/mL, etc.), Transferrin (e.g., 1-10 mg/ml, 3-7 mg/ml, about 5 mg/mL, etc.), Selenium (e.g., 1-10 ng/ml, 3-7 ng/ml, about 5 ng/mL, etc.), etc. In some embodiments, fallopian culture media comprises one or more (e.g., all) of: alpha MEM, BSA (e.g., 3 mg/ml), Fetuin (e.g., 0.5 mg/mL), Insulin (e.g., 5 mg/mL), Transferrin (e.g., 5 mg/mL), Selenium (e.g., 5 ng/mL), etc.

In some embodiments, uterine culture media comprises one or more (e.g., all) of: DMEM F12, Insulin, Transferrin, Selenium, pen-strep, stripped FBS, etc. In some embodiments, uterine culture media comprises one or more (e.g., all) of: DMEM F12, Insulin (e.g., 1-10 µg-ml, 3-7 µg/ml, about 5 µg/ml, etc.), Transferrin (e.g., 1-10 µg-ml, 3-7 µg/ml, about 5 µg/ml, etc.), Selenium (e.g., 1-10 ng/ml, 3-7 ng/ml, about 5 ng/mL, etc.), pen-strep (0.1-10%, 0.5-5%, about 1%, etc.), stripped FBS (e.g., 1-10%, 3-7%, about 5%, etc.), etc. In some embodiments, uterine culture media comprises one or more (e.g., all) of: DMEM F12, Insulin (5 ug/mL), Transferrin (5 ug/mL), Selenium (5 ng/mL), 1% pen-strep, 5% stripped FBS, etc.

In some embodiments, endocervix culture media comprises one or more (e.g., all) of: KBM (Keratinocyte Basal Medium), Insulin, Transferrin, EGF, Gentamicin-amphotericin-B, Bovine Pituitary Extract (BPE), Ephinephrine, hydrocortisone, etc. In some embodiments, endocervix culture media comprises one or more (e.g., all) of: KBM (Keratinocyte Basal Medium), Insulin (e.g., 1-10 µg/ml, 3-7 µg/ml, about 5 µg/ml, etc.), Transferrin (e.g., 1-20 µg/ml, 5-15 µg/ml, about 10 µg/ml, etc.), EGF (e.g., 0.025-1 µg/ml, 0.05-0.25 ng/ml, about 0.125 ng/ml, etc.), Gentamicin-amphotericin-B (e.g., 0.01-1%, 0.05-0.5%, about 0.1%, etc.), Bovine Pituitary Extract (BPE) (e.g., 0.1-1%, 0.2-0.6%, about 0.4%, etc.), Ephinephrine (e.g., 0.2-0.5 µg/ml, 0.3-0.45 µg/ml, about 0.39 ug/ml, etc.), hydrocortisone (e.g., 0.1-0.5 µg/ml, 0.2-0.4 µg/ml, about 0.33 µg/ml, etc.). In some embodiments, endocervix culture media comprises one or more (e.g., all) of: KBM (Keratinocyte Basal Medium), Insulin (5 ug/mL), Transferrin (10 ug/mL), EGF (0.125 ng/mL), Gentamicin-amphotericin-B (0.1%), Bovine Pituitary Extract (BPE) (0.4%), Ephinephrine (0.39 ug/mL), and hydrocortisone (0.33 ug/mL).

In some embodiments, endocervix culture media comprises one or more (e.g., all) of: adenine, human recombinant, human apo-transferin, triiodothyronine, DMEM HG, DMEM:F-12, gentamicin, amphoterici, 4 mm L-Glut, hydrocortisone, and cholera toxin in amounts plus or minus 50%, 40%, 30%, 20%, or 10% of the concentrations in Example 8.

In some embodiments, two or more subsystems (e.g., all) utilize the same media (e.g., universal media). In some embodiments, universal media comprises one or more of the aforementioned components.

In some embodiments, a microphysiologic system is provided comprising one or more (e.g., two or more, 3, 4, 5, 6, or more) culture subsystems in fluid communication via microfluidics. In some embodiments, the present invention is not limited by the identity, manufacturer (e.g., Draper Laboratory, Quiatech, etc.), or type of microfluidic system.

In some embodiments, the present invention provides compositions and methods for a female reproductive tract organ system capable of mimicking the female menstrual cycle (See, e.g., Example 1).

In some embodiments the present invention provides a female reproductive tract organ system capable of assessing the effects of environmental contaminants on female reproduction (See, e.g., Example 2).

In some embodiments the present invention is capable of assessing the biological function of a single organ in the organ system including its response to the female menstrual cycle (See, e.g., Example 3).

In some embodiments, a microphysiologic system comprises a subsystem that mimics the behavior of the human uterus. Experiments were conducted during development of embodiments of the present invention to produce such a subsystem (See, e.g., Example 4).

In some embodiments, a microphysiologic system comprises a subsystem that mimics the behavior of the human ovaries. Experiments were conducted during development of embodiments of the present invention to produce such a subsystem (See, e.g., Example 5).

In some embodiments, a microphysiologic system comprises a subsystem that mimics the behavior of the human fallopian tubes. Experiments were conducted during development of embodiments of the present invention to produce such a subsystem (See, e.g., Example 6).

In some embodiments, a microphysiologic system comprises a subsystem that mimics the behavior of the human endocervix. Experiments were conducted during development of embodiments of the present invention to produce such a subsystem (See, e.g., Example 7).

In some embodiments, a microphysiologic system comprises a subsystem that mimics the behavior of the human ectocervix. Experiments were conducted during development of embodiments of the present invention to produce such a subsystem (See, e.g., Example 8).

Although some embodiments are described as pertaining to the human female reproductive tract, the present invention is not so limited, and may find use with non-human animals as well (e.g., other mammals, non-human primates, rodents, canines, felines, bovines, equines, porcines, etc.).

EXPERIMENTAL

Example 1

Engineering Rodent and Human Hormonal Menstrual Cycles in an Artificial Ovary

The menstrual cycle in humans and estrous cycle in rodents represent a series of hormone and tissue changes that support female fertility and endocrine health. To easily study hormonal changes over the menstrual cycle, we developed an encapsulated three dimensional (3D) human and murine in vitro follicle growth (eIVFG) system that creates a physical environment that supports both follicle development, including lutenization, and hormone secretion. The hormones from eIVFG-cultured human and mouse follicles were profiled, and the genes involved in the follicular-luteal transition in mouse follicle culture were characterized. Furthermore, mouse follicles were able to secrete steroid hormones in a pattern that mimics the human 28 day cycle. The 3D eIVFG culture system reliably phenocopies in vivo follicle hormone production and gene expression profiles, providing new opportunities to probe molecular mechanisms and the effects of iatrogenic insults on follicle function in the cycling female.

One purpose of the female reproductive axis is to produce, through the complex process of folliculogenesis, a terminally differentiated haploid egg that can be fertilized by sperm to produce a viable embryo (E. A. McGee, A. J. Hsueh, Initial and cyclic recruitment of ovarian follicles. Endocrine reviews 21, 200 (April, 2000); herein incorporated by reference in its entirety). The central organ of the female reproductive axis is the ovary and the basic unit of the ovary is the follicle, which is composed of a germ cell surrounded by somatic cells, (granulosa and theca cells). Large follicles are visible on the surface of the ovary as fluid filled, blister-like structures containing a single oocyte that will be released from the ovary into the oviduct, or fallopian tube, at ovulation. During human development, one million follicle-enclosed oocytes arrest in meiotic prophase, a resting state that can last for years or decades before beginning a program of development that leads to a mature, fertilizable egg. Once the follicle is selected to resume growth, the somatic cells produce and release hormones, like the steroid hormones estrogen and progesterone, with carefully orchestrated timing to control oocyte development, menses, and implantation while also coordinating hormonally responsive signaling pathways throughout the body. Therefore, follicle produced hormonal fluctuations are a ubiquitous part of female physiology and have important effects on the function of non-reproductive organs and therapeutic outcomes.

Avenues for studying in vivo human follicle development and the influence of hormonal fluctuations during the menstrual cycle on human physiology are limited. Therefore, in vitro models that recapitulate the 28-day human menstrual cycle using three dimensional (3D) follicle culture are required to completely understand not only reproductive function, but also whole body health. The recent development of in vitro follicle culture by our group has made it possible, for the first time, to assess hormone production by human and mouse follicles at various stages of growth (M. Xu et al., Encapsulated three-dimensional culture supports development of nonhuman primate secondary follicles. Biology of reproduction 81, 587 (September, 2009); M. Xu, A. Banc, T. K. Woodruff, L. D. Shea, Secondary follicle growth and oocyte maturation by culture in alginate hydrogel following cryopreservation of the ovary or individual follicles. Biotechnology and bioengineering 103, 378 (Jun. 1, 2009); herein incorporated by reference in their entireties). Experiments were conducted during development of embodiments of the present invention to build a new model that recapitulates a complete in vivo follicle hormone production cycle in vitro in order to advance our understanding of follicle biology and the environment in which the gamete develops. Application of this model includes integration of 3D maturing follicles into a microphysiologic system to study the effects of ovarian hormones on the female reproductive tract and non-reproductive tissues.

Figure 1:
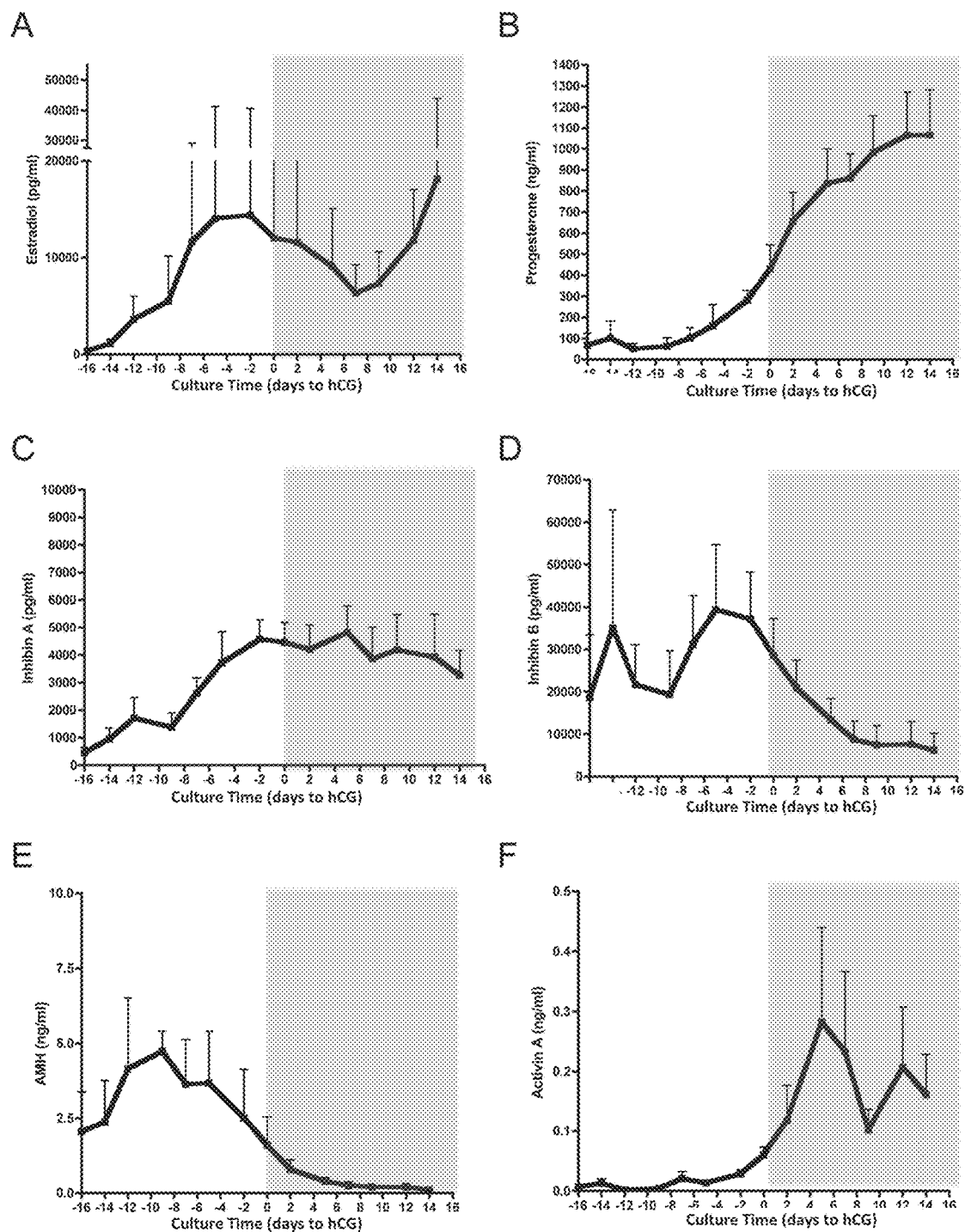
FIG. 1. Steroid and peptide hormone profiles of in vitro follicle growth (IVFG) cultured secondary human follicles. Steroid and peptide hormones were quantified in the medium throughout the culture period. Secondary human follicles were isolated and cultured in alginate from 40 to 65 days. The culture time on X-axis had been aligned to the time of the hCG addition (day 0) and cultured for an additional 14-15 days. The concentration of (A) estradiol, (B) inhibin A, (C) AMH, (D) progesterone, (E) inhibin B, and (F) activin A are reported throughout culture relative to hCG administration. Gray shading represents the in vitro luteal phase, or time post-hCG. Follicles were derived from three donors and individually cultured.

It has been shown that an alginate-based encapsulated in vitro follicle growth (eIVFG) system supports coordinated folliculogenesis and oogenesis in follicles from all mammalian species examined to date (M. Xu et al., In vitro grown human ovarian follicles from cancer patients support oocyte growth. Human reproduction 24, 2531 (October, 2009); M. Xu et al., Encapsulated three-dimensional culture supports development of nonhuman primate secondary follicles. Biology of reproduction 81, 587 (September, 2009); M. Xu, A. Banc, T. K. Woodruff, L. D. Shea, Secondary follicle growth and oocyte maturation by culture in alginate hydrogel following cryopreservation of the ovary or individual follicles. Biotechnology and bioengineering 103, 378 (Jun. 1, 2009); M. Xu et al., In vitro oocyte maturation and preantral follicle culture from the luteal-phase baboon ovary produce mature oocytes. Biology of reproduction 84, 689 (April, 2011). herein incorporated by reference in their entireties). In this study, we performed a comprehensive analysis of the hormones produced by human preantral follicles during a longer eIVFG cycle that included a FSH-driven follicular phase, and ovulation stimulus and an in vitro luteal phase. Secondary stage human follicles (120 μm to 260 μm diameter) were isolated from ovarian tissue donated for research under IRB approval and following informed consent. Follicles were encapsulated in 0.3% alginate, and levels of estradiol, progesterone, inhibin A, inhibin B, AMH, and activin A were measured in the spent culture media throughout culture (FIG. 1). The in vitro follicular phase of development was tracked for each individual follicle by measuring estradiol, and once these levels plateaued at approximately 15 days of culture, luteinization was triggered by human chorionic gonadotropin (hCG) administration for 36 hours. Luteninization represents the terminal differentiation of estrogen-producing granulosa cells into progesterone-producing luteal cells. The in vitro luteal phase was monitored for an additional 15 days post-hCG, resulting in total cultures times that ranged from 40 to 65 days.

Figure 4:
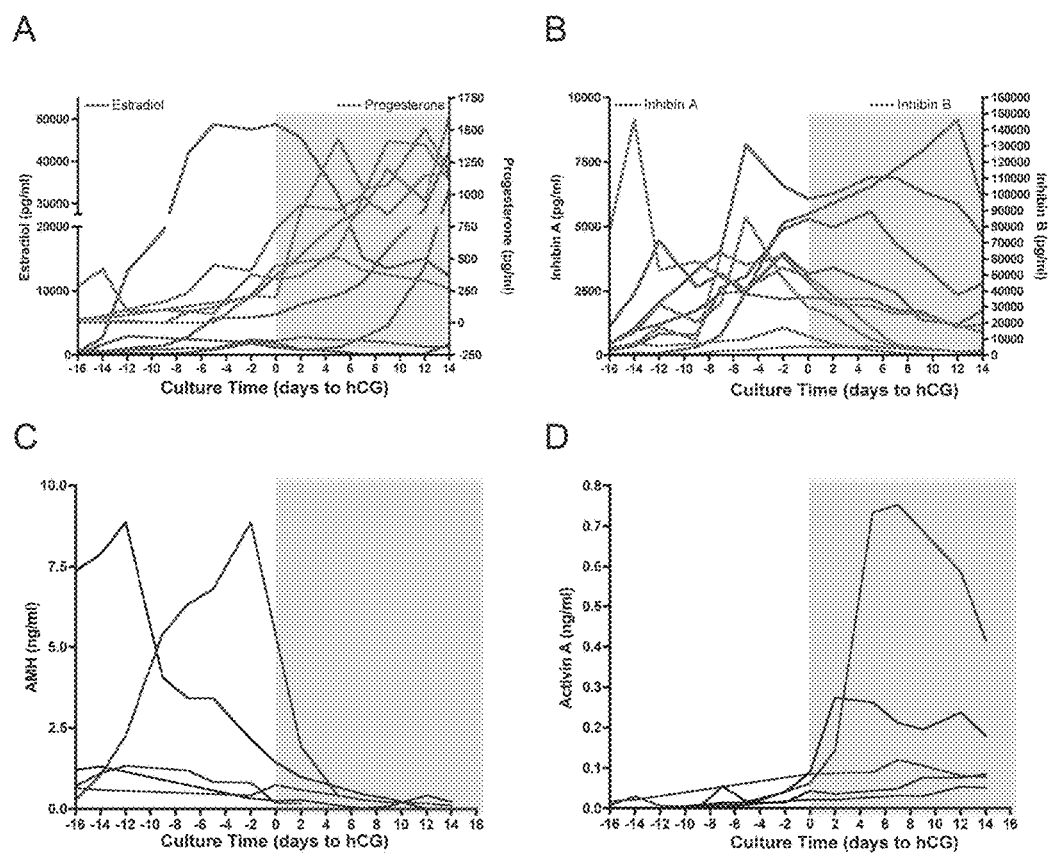
FIG. 4. Individual steroid and peptide hormone profiles in growing secondary human follicles. Steroid and peptide hormones for each human follicle were quantified in the medium throughout the culture period. The culture time on X-axis had been aligned to the time of the hCG addition (day 0) and cultured for an additional 14-15 days. The concentration of (A) estradiol, progesterone, (B) inhibin A, inhibin B, (C) AMH and (D) activin A are reported throughout culture relative to hCG administration. Gray shading represents the in vitro luteal phase, or time post-hCG. Follicles were derived from three donors and individually cultured.

Although the absolute levels of steroid and peptide hormones produced by individual follicles varied (FIG. 4), the overall patterns were similar to each other and to hormone cycle measured in vivo (N. A. Klein et al., Age-related analysis of inhibin A, inhibin B, and activin a relative to the intercycle monotropic follicle-stimulating hormone rise in normal ovulatory women. The Journal of clinical endocrinology and metabolism 89, 2977 (June, 2004); J. MacNaughton, M. Banah, P. McCloud, J. Hee, H. Burger, Age related changes in follicle stimulating hormone, luteinizing hormone, oestradiol and immunoreactive inhibin in women of reproductive age. Clinical endocrinology 36, 339 (April, 1992); C. K. Welt, Y. L. Pagan, P. C. Smith, K. B. Rado, J. E. Hall, Control of follicle-stimulating hormone by estradiol and the inhibins: critical role of estradiol at the hypothalamus during the luteal-follicular transition. The Journal of clinical endocrinology and metabolism 88, 1766 (April, 2003); herein incorporated by reference in their entireties) Inhibin B was the predominant inhibin produced by small antral follicles, rising in the early to mid-follicular phase and declining in the later follicular phase. Inhibin A and estradiol levels increased and reached maximal levels as the follicles reached maturity during the follicular phase. Post-hCG, progesterone levels increased and there was a trend towards higher activin A, as is found in human serum (S. Muttukrishna, P. A. Fowler, L. George, N. P. Groome, P. G. Knight, Changes in peripheral serum levels of total activin A during the human menstrual cycle and pregnancy. The Journal of clinical endocrinology and metabolism 81, 3328 (September, 1996); herein incorporated by reference in its entirety) Inhibin A levels dropped transiently with hCG treatment, but then rose and remained elevated throughout the luteal phase. In contrast, inhibin B levels remained low during the luteal phase. The discordance of inhibin A and inhibin B during the luteal phase is unique to primates and is replicated here (N. A. Klein et al., Age-related analysis of inhibin A, inhibin B, and activin a relative to the intercycle monotropic follicle-stimulating hormone rise in normal ovulatory women. The Journal of clinical endocrinology and metabolism 89, 2977 (June, 2004); C. K. Welt, J. E. Hall, J. M. Adams, A. E. Taylor, Relationship of estradiol and inhibin to the follicle-stimulating hormone variability in hypergonadotropic hypogonadism or premature ovarian failure. The Journal of clinical endocrinology and metabolism 90, 826 (February, 2005); herein incorporated by reference in their entireties). AMH, a hormone used clinically as a surrogate marker of small follicles, reached its peak in the early follicular phase and dropped before mid-follicular phase. Serum AMH levels in women remain constant during the menstrual cycle, reflecting the fact that AMH is made by a fairly constant recruitment of immature follicles into the growing pool C. Weenen et al., Anti-Mullerian hormone expression pattern in the human ovary: potential implications for initial and cyclic follicle recruitment. Molecular human reproduction 10, 77 (February, 2004); A. L. Durlinger, J. A. Visser, A. P. Themmen, Regulation of ovarian function: the role of anti-Mullerian hormone. Reproduction 124, 601 (November, 2002); herein incorporated by reference in their entireties). The culture of individual human follicles shows that on a per follicle basis, AMH is made only through the time of antrum cavity formation, a new discovery that provides opportunity for study of signaling pathways that control this marker of a developing follicle.

Figure 2:
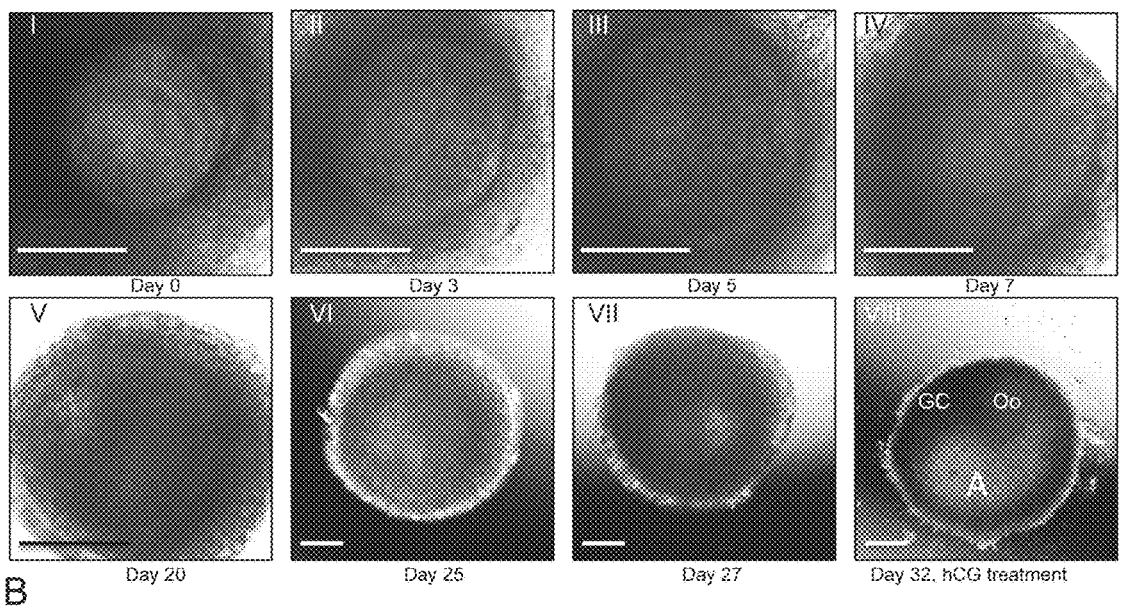
FIG. 2. Alginate culture supports human follicle growth and structural luteinization. (A) Representative image of in vitro human follicle growth. A single secondary human follicle (147 µm) was isolated from the ovarian cortex and grown in 0.3% alginate. On day 32, the follicle measured approximately 600 µm in diameter and hCG was administered. (B) Representative images of H&E stained secondary human follicles (i) pre-hCG and (ii) 15 days post-hCG (Culture days 32 and 43, respectively). Follicles showed morphological signs of luteinization, marked by a significant increase in cytoplasmic to nuclear ratio, shown in (C) and a significant increase in the number of nuclei, in (D) are presented. Scale Bar=100 µm. Abbreviations: Oo (oocyte); GC (granulosa cells); A (antrum).
Figure 2:
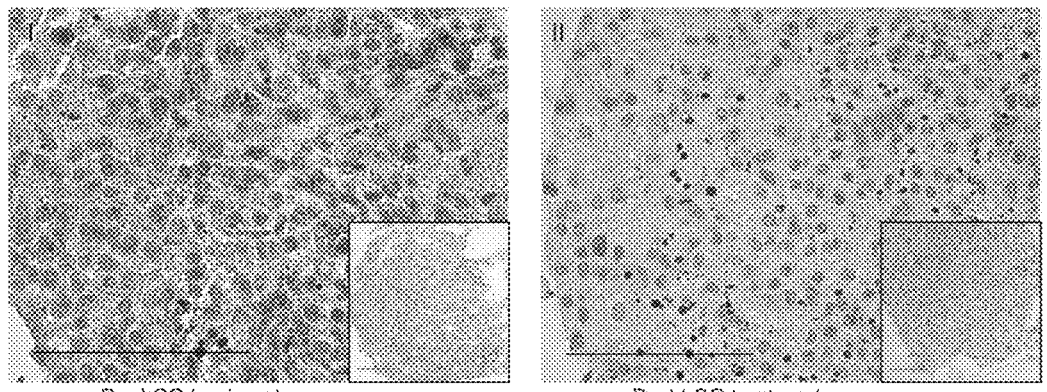
Figure 2:
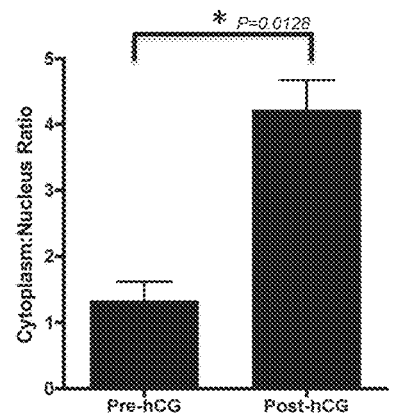
Figure 2:
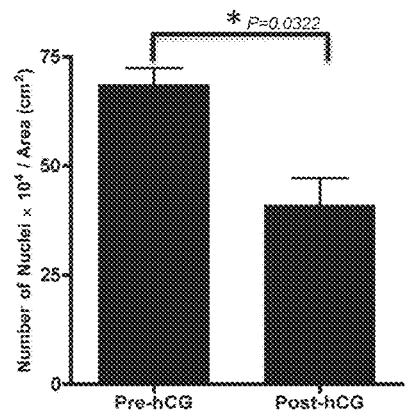

In addition to changes in hormone secretion, ovarian follicles underwent morphological changes representative of in vitro maturation. Specifically, ovarian follicles completed a growth phase (FIG. 2A), followed by luteinization post-hCG. The growth phase coincided with the expected timing of the follicular phase, while post-hCG, histological analysis showed the characteristic granulosa cell hypertrophy associated with luteinization (FIG. 2B-D). These results indicate that the endocrinology of the human follicle is faithfully recapitulated in the eIVFG system.

Figure 3:
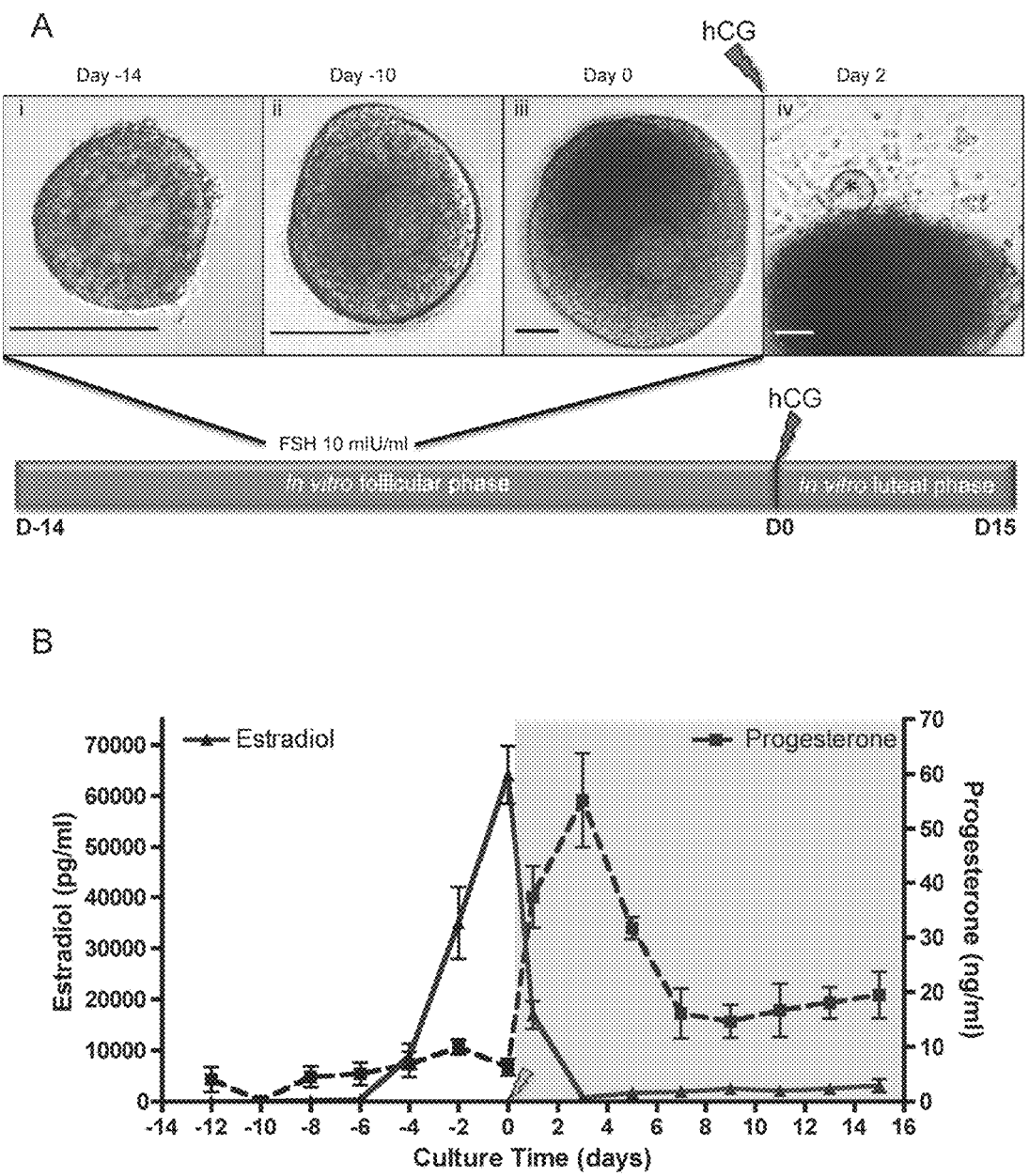
FIG. 3. Using murine multiple follicle culture to phenocopy the human menstrual cycle. (A) Late primary and early secondary stage follicles (90 µm to 120 µm) were isolated from mouse ovaries and encapsulated in 0.5% alginate in cohorts of 10 follicles per alginate bead. Follicles were cultured for 14 days (Day-14 to Day 0, in vitro follicular phase). On Day 0, hCG was administered to induce ovulation and follicles were cultured for an additional 15 days (in vitro luteal phase). (i) is the initial size of follicle (Day-14) (ii) the morphology of follicle on day-10 (iii) is the day follicle was given hCG (Day 0), (iv) follicles cultured in alginate released oocyte (asterisk) in response to hCG. Scale Bar=100 µm. (B) Estradiol and progesterone were measured in spent medium throughout the culture period. Lighting bolt represents hCG treatment.
Figure 5:
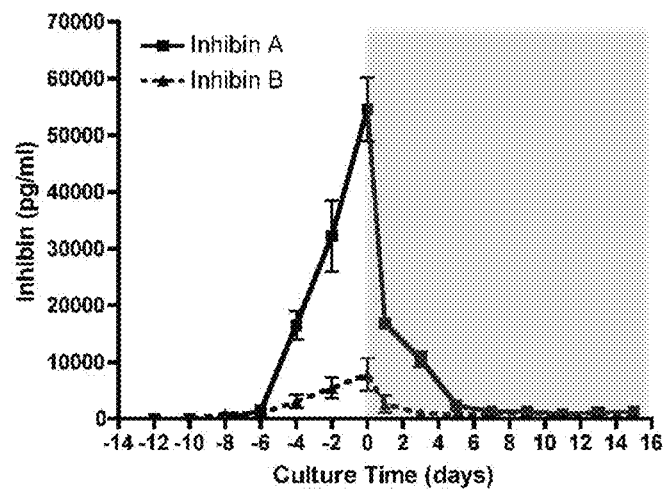
FIG. 5. Peptide hormone profiles of murine multiple follicle culture. (A) Inhibin A, inhibin B, and (B) AMH were measured throughout the culture period. (B) H&E staining of secondary mouse follicles pre-hCG and post-hCG. Follicles showed morphological signs of luteinization, marked by an increased cytoplasmic to nuclear ratio. Scale Bar=100 µm.
Figure 5:
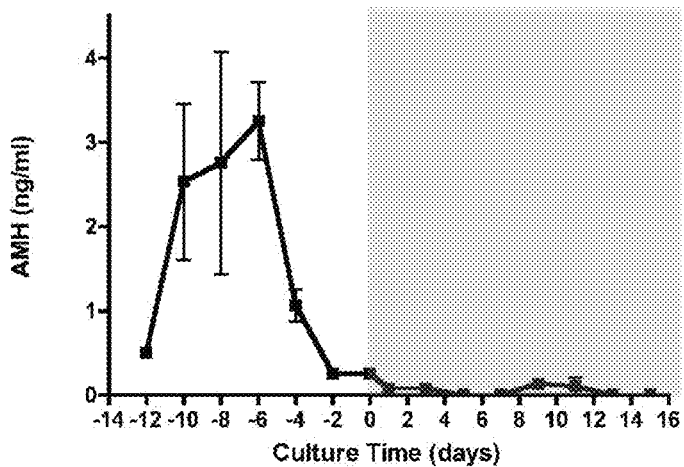
Figure 5:
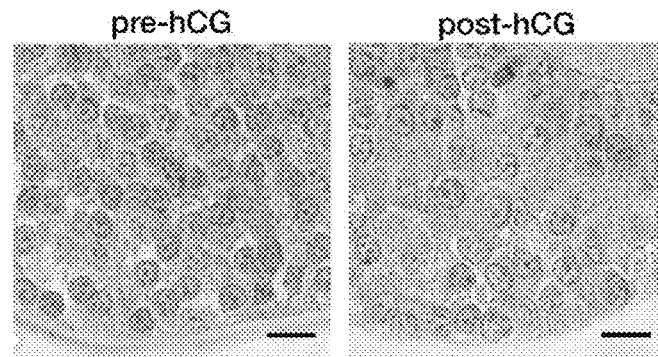

Although this culture technique provides a robust method to study follicular and luteal endocrinology, access to human follicles is limited. Thus, experiments were conducted during development of embodiments of the present invention to phenocopy the hormone production of the human menstrual cycle using eIVFG cultured mouse follicles. Late primary stage follicles were isolated from 12-day old mouse ovaries and encapsulated in 0.5% alginate in cohorts of 10 follicles. Follicles were cultured for 14 days (in vitro follicular phase) upon which hCG was administered to induce ovulation followed by an additional 15 days of culture (in vitro luteal phase) (FIG. 3A). The patterns of estradiol, progesterone, inhibin B and AMH production during this 29-day culture mimicked a complete human menstrual cycle with both follicular and luteal phases (FIG. 3B and FIG. 5). The phenocopied human menstrual cycle was capitalized by co-culturing mouse follicles with 3D human fallopian tube epithelia. Hormones produced by mouse follicles stimulated human fallopian epithelia cilia beating and expression of oviductal proteins.

A difference between human and mouse is the luteal phase secretion pattern of the peptide hormone inhibin A. In the primate, inhibin A is expressed post-LH and augments progesterone production (W. Ge, R. E. Peter, Activin-like peptides in somatotrophs and activin stimulation of growth hormone release in goldfish. General and comparative endocrinology 95, 213 (August, 1994); herein incorporated by reference in its entirety) and suppresses FSH T. K. Woodruff et al., Inhibin A and inhibin B are inversely correlated to follicle-stimulating hormone, yet are discordant during the follicular phase of the rat estrous cycle, and inhibin A is expressed in a sexually dimorphic manner. Endocrinology 137, 5463 (December, 1996);

K. I. Parker, D. M. Robertson, N. P. Groome, K. L. Macmillan, Plasma concentrations of inhibin a and follicle-stimulating hormone differ between cows with two or three waves of ovarian follicular development in a single estrous cycle. Biology of reproduction 68, 822 (March, 2003); T. A. Molskness, T. K. Woodruff, D. L. Hess, K. D. Dahl, R. L. Stouffer, Recombinant human inhibin-A administered early in the menstrual cycle alters concurrent pituitary and follicular, plus subsequent luteal, function in rhesus monkeys. The Journal of clinical endocrinology and metabolism 81, 4002 (November, 1996); B. S. Houmard et al., Age-related analysis of inhibin A and B relative to the intercycle monotropic FSH rise in normal ovulatory women. Annales d'endocrinologie 64, 86 (April, 2003); herein incorporated by reference in their entireties). In the mouse, the inhibin subunits ($\alpha$ and $\beta_A$ and $\beta_B$) are transcriptionally repressed by the NR4A and C/EBP$\beta$ transcription factors (A. D. Burkart, A. Mukherjee, E. Sterneck, P. F. Johnson, K. E. Mayo, Repression of the inhibin alpha-subunit gene by the transcription factor CCAAT/enhancer-binding protein-beta. Endocrinology 146, 1909 (April, 2005); herein incorporated by reference in its entirety). To explore species-specific inhibin A regulation in the 29-day mouse follicle culture system, inhibin A secretion and gene expression was examined. As predicted by the mouse hormone patterns measured in vivo, in vitro inhibin A fell at the time of hCG. This result indicates that the species-specific mechanisms governing mouse and human inhibin subunit expression are retained in the eIVFG setting although the hormone secretion pattern from mouse follicles mimicked a human menstrual cycle. Given the limited amount of human tissue, examination of gene expression profiles of NR4A and C/EBPβ was not possible. However, using the mouse system, we quantified the expression of these transcription factors during the in vitro mouse luteal phase of culture mouse follicles (FIG. S3). Nr4a1-3 and C/EBPβ were upregulated post-hCG, providing evidence that cultured rodent follicles were following the normal murine pattern of gene regulation. In addition, expression was examined of steroidogenic enzymes (Star, Hsd3β1, Cyp11α1 and Akr1c18) known to be upregulated post-hCG in the mouse as well as the follicular enzymes responsible for estrogen synthesis (Cyp17α1 and Cyp19α1). Expression of these enzyme systems phenocopied patterns observed in vivo (Ronen-Fuhrmann et al., Spatio-temporal expression patterns of steroidogenic acute regulatory protein (StAR) during follicular development in the rat ovary. Endocrinology 139, 303 (January, 1998); L. Hedin, R. J. Rodgers, E. R. Simpson, J. S. Richards, Changes in content of cytochrome P450(17) alpha, cytochrome P450scc, and 3-hydroxy-3-methylglutaryl CoA reductase in developing rat ovarian follicles and corpora *lutea*: correlation with theca cell steroidogenesis. Biology of reproduction 37, 211 (August, 1987); M. F. Hay, R. M. Moor, Distribution of delta-5-3beta-hydroxysteroid dehydrogenase activity in the Graafian follicle of the sheep. Journal of reproduction and fertility 43, 313 (May, 1975); N. B. Goldring et al., Cholesterol side-chain cleavage P450 messenger ribonucleic acid: evidence for hormonal regulation in rat ovarian follicles and constitutive expression in corpora *lutea*. Endocrinology 120, 1942 (May, 1987); G. F. Erickson, A. J. Hsueh, Stimulation of aromatase activity by follicle stimulating hormone in rat granulosa cells in vivo and in vitro. Endocrinology 102, 1275 (April, 1978); herein incorporated by reference in their entireties). The measurement of gonadotropin receptor expression provided a final analytical benchmark of the changes associated with luteal transitions in vitro—the FSH receptor was acutely down-regulated by FSH while the LH receptor was unregulated and maintained for 5 days post-hCG (J. S. Richards et al., Ovarian follicular development in the rat: hormone receptor regulation by estradiol, follicle stimulating hormone and luteinizing hormone. Endocrinology 99, 1562 (December, 1976); herein incorporated by reference in its entirety). Given the paucity of human tissue, applying mouse tissue to this engineered environment provides an alternative approach to study the molecular regulation of these important hormone transitions.

Taken together, these results demonstrate that eIVFG is a powerful technique that allows the controlled study of human follicular and luteal endocrinology in ways that have not been possible to date. These studies provide the first opportunity to track in vitro the hormone and transcriptional changes that correlate with healthy follicles, using a model that will provide new insights into mechanisms of fertility and reproductive function at the level of the single follicle. In addition to being able to control the power of the menstrual hormones in a dish, we were able to determine hormone production on a follicle by follicle level—including AMH which does not change during the menstrual cycle because of the aggregate production of this hormone by constantly renewing follicles. The mouse follicle cycle was extended to a 28 days period, during which the hormone secretion pattern mimicked the human menstrual cycle. One hormone that differs between mouse and human is inhibin A, and this hormone and its regulating transcription factors, followed the mouse pattern precisely.

Experiments were conducted during development of embodiments of the present invention that succeeded in culturing human and mouse follicles in a culture system that permits follicular phase growth, ovulation and luteinization. Using this approach iatrogenic effects of chemotherapeutics and endocrine disruptors on follicles and oocyte can be studied, mechanisms governing follicle selection can be explored, and an in vitro setting where oocyte maturation is supported leading to competent fertilizable eggs is created.

Acquisition of Human Ovarian Tissue

Human ovarian tissue was obtained following informed consent under Institutional Review Board-approved protocols at Northwestern University. After surgical removal, ovaries were transported to the laboratory in 48 hours at 4° C. in SAGE OFC holding Media (Cooper Surgical, Trumbull, Conn.). In all cases, the ovaries were processed using a standard technique in ovarian tissue cryopreservation in which the ovarian cortex is separated from the medulla (oncofertility.northwestern.edu/media/dissection-human-ovary-preparation-cryopreservation).

Human Follicle Culture and In Vitro Luteinization

Human follicles were isolated using a modified method as described previously (R. Abir et al., Pilot study of isolated early human follicles cultured in collagen gels for 24 hours. Human reproduction 14, 1299 (May, 1999); herein incorporated by reference in its entirety). Ovarian cortical strips were cut into 1 $mm^3$ pieces in alpha MEM Glutamax (Invitrogen, Carlsbad, Calif.) supplemented with 1% Pen-Strep, 1% Serum Protein Substitute (SPS, Cooper Surgical, Trumbull, Conn.) and 1.5 IU/ml hCG. The tissue was then enzymatically digested by supplementing αMEM Glutamax with 1% Liberase TM (Roche, Indianapolis, Ind.) and 0.1% DNase (Worthington, Lakewood, N.J.) for 30 minutes at 37° C. After rinsing the cortex three times with fresh Sage holding medium, follicles were then mechanically isolated from the cortex using insulin gauge needles, and encapsulated in 0.3% alginate (NovaMatrix, Philadelphia, Pa.). Encapsulated human follicles were transferred to a 96-well plate containing 100 μl of growth media [αMEM Glutamax (Invitrogen, Carlsbad, Calif.) supplemented with 0.5 mg/ml fetuin, 0.3% human serum albumin (Cooper Surgical, Trumbull, Conn.), 5 μg/ml insulin, 5 μg/ml transferrin and 5 ng/ml selenium (Sigma-Aldrich, St. Louis, Mo.), and 5 mIU recombinant FSH (A. F. Parlow, National Hormone and Pituitary Program, National Institute of Diabetes and Digestive and Kidney Diseases, USA)], and placed in an incubator at 37° C. and 5% CO2. Half of the culture medium was exchanged every other day. The follicular phase of development was tracked for each individual follicle by measuring estradiol, and once these levels plateaued, luteal conversion was triggered by hCG administration for 36 hours and cultured for an additional 15 days. After 36 hours incubation in maturation media, half of the media was exchanged for growth medium without FSH.

Animals and Follicle Isolation

Animal experiments were performed using CD-1 female mice (Harlan Laboratories, Indianapolis, Ind.) that were housed in a controlled barrier facility at Northwestern University's Center of Comparative Medicine with constant temperature, humidity and light (12 h light/12 h darkness)

and food and water were provided ad libitum. All animal experiments were approved by the Institutional Animal Care and Use Committee and were in accordance with National Institutes of Health Guidelines as well. Follicles (90 μm-120 μm) were mechanically isolated from ovaries of 12- to 13-day old mice in L15 media (Invitrogen) supplemented with 1% fetal bovine serum (FBS, Invitrogen) and 10% streptomycin (Invitrogen), and encapsulated in cohorts of 10 follicles in 0.5% w/v alginate as previously described (32). Briefly, individual follicles were maintained in minimal essential medium (αMEM Glutamax, Invitrogen) supplemented with 1% FBS and 10% streptomycin (αMEM/FBS/Streptomycin) after isolation for at least 30 minutes before encapsulation. Follicles were then encapsulated in cohorts of ten (×10) in 0.5% (w/v) alginate (NovaMatrix, Philadelphia, Pa.). Follicles were rinsed with alginate and transferred to a 5 μl alginate drop made on a polypropylene mesh (McMaster-Carr, Atlanta, Ga.). The mesh was immediately lifted upside down over the calcium solution (50 mM $CaCl2$ and 140 mM NaCl) for 2 min to allow for cross-linking to occur. The alginate beads were removed from mesh and placed in αMEM/FBS/Streptomycin in the incubator to recover for at least 30 minutes before transferred to culture medium.

Mice Follicle Culture and In Vitro Luteinization

Alginate encapsulated follicles were placed in individual wells of 96-well plate containing 100 μl of growth medium [GM: αMEM Glutamax supplemented with 3 mg/ml BSA (MP Biomedicals, Solon, Ohio), 10 mIU/ml recombinant FSH (A. F. Parlow, National Hormone and Pituitary Program, National Institute of Diabetes and Digestive and Kidney Diseases, USA), 1 mg/ml bovine fetuin, 5 μg/ml insulin, 5 μg/ml transferrin, and 5 ng/ml selenium (Sigma-Aldrich)] in a humidified atmosphere of 5% $CO_2$ in air at 37° C. for up to 14 days (in vitro follicular phase) upon which 1.5 IU hCG was administered to induce ovulation followed by an additional 15 days of culture (in vitro luteal phase). Half of the culture media was exchanged with fresh growth medium (GM) every other day and conditioned medium stored at −20° C. Follicles were imaged at each medium change time point using a Leica DM IRB inverted microscope equipped with 4× and 20× objectives to assess growth and survival. Follicles that contained an oocyte surrounded completely by somatic cells would be defined as live follicles. Dead follicles were defined by unhealthy oocytes, dark granulosa cells, or lost structural integrity.

Immunohistochemistry

Follicles were fixed in Modified Davidson's Fixative (Electron Microscopy Sciences, Hatfield, Pa.) at the end of human follicle culture for overnight at 4° C. And then follicles were dehydrated in increasing concentrations of ethanol (50-70%) and embedded in paraffin. The follicles were sectioned at 5 μm serially and stained with hematoxylin and eosin. The cytoplasm to nucleus ratio and number of nucleus per 1 $cm^2$ were quantified by Image J (National Institute of Health, Bethesda, Md.).

Hormone Assays

β-estradiol, progesterone, inhibin A, inhibin B, activin A and AMH were measured in spent medium by commercially available ELISA kits [estradiol and progesterone (Calbiotech, Spring Valley, Calif.); AMH and inhibin B (Diagnostic Systems Laboratories); inhibin A (Beckman Coulter, Pasadena, Calif.); Activin A (Ansh Labs, Webster, Tex.)]. The limits of sensitivity for estradiol, progesterone, inhibin A, inhibin B, Activin A and AMH were 3.94 pg/ml, 0.22 ng/ml, <5.0 pg/ml, 7 pg/ml, 0.065 ng/ml, 0.006 ng/ml, respectively. For each murine follicle culture, the beads with at least 8 survived follicles on day 8 were selected. The media were then pooled together from different wells to do the hormone assays. However, the cultured media of five human follicles were measured independently.

RNA Isolation and Real-Time PCR

RNA was purified from follicles using the Qiagen RNeasy Micro Kit according to the manufacturer's protocol (Qiagen, Valencia, Calif.). RNA quality and quantity were assessed both by NanoDrop (Thermo Scientific, Wilmington, Del.) and BioAnalyzer 210 Expert (Agilent Technologies, Santa Clara, Calif.). From each condition, 100 ng of RNA was used for synthesis of full-length cDNA using the AccuScript High Fidelity 1st strand cDNA synthesis Kit (Aligent, Santa Clara, Calif.). Real-time PCR was performed on the ABI PRISM® 7900HT Fast Real-Time PCR System (Applied Biosystems, Foster City, Calif.) using both the Taqman® Universal PCR Master Mix (Roche SOURCE, Indianapolis, Ind.) and Taqman® Gene Expression Assays (Applied Biosystems, Foster City, Calif.) according to the manufacturer's specifications. Gene-specific probes were labeled with the FAM reporter dye at the 5' end whereas a non-fluorescent quencher was linked to the 3' end of the probe. Each sample was performed in technical and biological duplicate and all results were normalized to the endogenous control Rpl18. Analysis of relative gene expression was done using the comparative Ct (2-ΔΔCT) method (K. J. Livak, T. D. Schmittgen, Analysis of relative gene expression data using real-time quantitative PCR and the 2(-Delta Delta C(T)) Method. Methods 25, 402 (December, 2001); herein incorporated by reference in its entirety).

Statistics

Plotting of results and statistical analysis was done using GraphPad Prism (La Jolla, Calif.). All experiments were independently performed at least 3 times, unless otherwise noted. For comparisons between groups, a one-way ANOVA followed by Bonferroni post hoc test or unpaired Student t test was performed. A P value of <0.05 was considered statistically significant.

Example 2

A Mammalian In Vitro Follicle Growth (IVFG) Assay Predicts Adverse Female Reproductive Outcomes Following Corexit EC 9500a Exposure Drugs and Chemicals Cisplatin (CDDP) and cyclophosphamide (CTX) were obtained from Sigma-Aldrich (St. Louis, Mo.) and used at final concentrations of: 0.2, 1, and 5 μM. Nalbuphine and Raclopride were obtained from the NIH Clinical Collection (South San Francisco, Calif.) and used at final concentrations of: 0.2, 1, and 5 μM. Corexit EC 9500A was obtained via a Material Transfer Agreement from Nalco (Sugar Land, Texas). CE was used at final concentrations of: 5 ppm, 10 ppm, 25 ppm, 50 ppm, 75 ppm, 100 ppm, 125 ppm, 150 ppm, 200 ppm, 250 ppm, 300 ppm, 350 ppm and 400 ppm, which correspond to 4.75 mg/L, 9.5 mg/L, 23.75 mg/L, 47.5 mg/L, 71.25 mg/L, 95 mg/L, 118.75 mg/L, 142.5 mg/L, 180 mg/L, 237.5 mg/L, 285 mg/L, 332.5 mg/L and 380 mg/L.

Animals and Follicle Isolation

All experiments were performed using CD-1 female mice (Harlan Laboratories, Indianapolis, Ind.) that were housed in a controlled barrier facility at Northwestern University's Center of Comparative Medicine under constant temperature, humidity and light (12 h light/12 h dark). Food and water were provided ad libitum. All animal experiments were approved by the Institutional Animal Care and Use Committee and were in accordance with National Institutes of Health Guidelines. For follicle isolation, ovaries were dissected from 14-15-day-old mice and cut into 4 pieces. The tissue was incubated for 1 hour in L15 media (Invitrogen, Carlsbad, Calif., USA) containing 2% Liberase TM (Roche, Indianapolis, Ind.) and 1% DNase I (Worthington, Lakewood, N.J.). The enzymatic digestion was quenched by rinsing follicles in αMEM Glutamax (Invitrogen) containing 1% Fetal Bovine Serum (FBS, Invitrogen, Carlsbad, Calif.) and 0.5% Pen-Strep (Mediatech, Herndon, Va.). Type 5b multilayer secondary follicles (140-175 µm in diameter) were manually collected and cultured individually in wells of a 96-well plate (Pedersen and Peters, 1968; herein incorporated by reference in its entirety). Follicles were grown in 100 µl of growth media (GM) comprised of αMEM Glutamax supplemented with 10 mIU/ml recombinant follicle-stimulating hormone (rFSH; A. F. Parlow, National Hormone and Pituitary Program, National institute of Diabetes and Digestive and Kidney Diseases), 1% Pen-Strep, 5 µg/ml insulin, 5 µg/ml transferrin, and 5 ng/ml selenium (Sigma-Aldrich, St. Louis, Mo.).

Follicle Culture, Growth and Survival

Follicles were cultured at 37° C. in a humidified atmosphere of 5% $CO_2$ in air for up to 6 days. All chemical exposures were initiated on day 2 of culture. Half of the culture media was replaced with fresh GM every other day and spent media was stored at −20° C. for use in steroid hormone assays. Follicles were imaged at each media change using a Leica DM IRB inverted microscope equipped with 4× and 20× objectives (Leica Microsystems, Heidelberg, Germany) to assess survival, morphology and growth. Live follicles were defined as those that contained an oocyte surrounded completely by somatic cells. Dead follicles where characterized by dark granulosa cells, granulosa cells that failed to proliferate, or an oocyte that had dissociated completely from the follicle structure (Lenie et al. 2008' herein incorporated by reference in its entirety). The percent of surviving follicles was calculated as the number of live follicles out of the total number of follicles plated. Antral cavity formation was assessed morphologically and characterized by the differentiation of outer layers of mural granulosa cells and inner layers of cumulus granulosa cells surrounding the oocyte as well as the presence of a fluid-filled structure.

Hormone Assays

To assay hormones secreted by cultured follicles, spent culture media from viable follicles were pooled both on day 4 and day 6. β-estradiol (E2) was measured using a commercially available Estradiol (E2) ELISA Kit (Calbiotech, Inc. Spring Valley, Calif.) according to manufacturer's protocol. All assays were run in duplicate. The assay sensitivity is 3.94 pg/ml, and medium collected from wells without follicles was used as a negative control.

In Vitro Oocyte Maturation

In vitro maturation (IVM) was performed after 6 days of culture. Briefly, half of the medium was replaced with IVM medium (αMEM Glutamax containing 5 ng/ml epidermal growth factor, 1.5 IU/ml human chorionic gonadotropin (HCG) and 5% FBS) and follicles were incubated at 37° C. in a humidified atmosphere of 5% $CO_2$ in air for 14-16 h. Oocytes were then removed from the cumulus cells by treatment with 0.3% hyaluronidase. The meiotic stage of each oocyte was scored morphologically using the Leica DM IL microscope. Oocytes that remained arrested in prophase of meiosis I as evidenced by an intact germinal vesicle (GV) were classified as GV-intact oocytes. Oocytes that resumed meiosis and reached metaphase of meiosis II (MII) as evidenced by polar body extrusion were classified as MII-arrested eggs. Those oocytes that resumed meiosis but did not reach MII, as evidenced by lack of a both a GV and a polar body, were referred to as oocytes that had undergone GV breakdown (GVBD). Degenerate oocytes were also documented. The meiotic progression distribution is reported as the number of oocytes in each stage over the total number of follicles that were in vitro matured.

Egg Cytoskeleton Analysis

To examine the microtubule and actin cytoskeleton, cells were processed as described previously (Hornick and Duncan, 2012; herein incorporated by reference in its entirety). Briefly, oocytes were fixed in 3.8% paraformaldehyde (Electron Microscopy Sciences, Hatfield, Pa., USA) containing 0.1% Triton X-100 (Sigma-Aldrich) in 1× phosphate-buffered saline (PBS) for 1 hr at room temperature (RT). After fixation, oocytes were washed with blocking buffer (BB) containing 0.3% BSA, 0.02% $NaN_3$, and 0.01% Tween-20 in 1×PBS and then incubated in permeabilization solution containing 0.3% BSA, 0.1% Triton X-100 and 0.02% $NaN_3$ for 15 minutes. After rinsing with BB, oocytes were incubated in a 1:100 dilution of Alexa Fluor 488-conjugated α-tubulin Rabbit mAb for 1 h at RT to detect the microtubule cytoskeleton (Cell Signaling, Boston, Mass.). F-actin was detected by simultaneous incubation in a 1:50 dilution of rhodamine phalloidin (Invitrogen). All antibodies were diluted in BB. Oocytes were washed in BB after antibody incubations and mounted in Vectashield containing DAPI to detect DNA (Vector Laboratories, Burlingame, Calif., USA). Images were acquired with a Leica SP5 inverted laser-scanning confocal microscope equipped with a 40× objective and Confocal LAS AF software (Leica Microsystems, Heidelberg, Germany). Additional image processing was done using Image J software (National Institutes of Health, Bethesda, Md.). Spindle morphology was scored and normal spindles were defined as those that were bipolar and had chromosomes tightly aligned on the metaphase plate.

Ovarian Stromal Cell Isolation and Survival

Ovarian stromal cell isolation was carried out as described previously with minor modifications as detailed (Tingen et al. 2011; herein incorporated by reference in its entirety). Ovaries harvested from day 21-22 mice were placed in L15 media containing 0.5% Pen-Strep and 1% FBS. Granulosa cells were released by mechanical disruption of the ovaries using two insulin gauge needles. The remaining tissue was dissociated in 1× Trypsin/EDTA-Hanks (Invitrogen) containing 1% Liberase TM (source) and 1% DNase I (source) with gently rocking for 1 hr at 37° C. in a humidified atmosphere of 5% $CO_2$ in air. The enzymatic reaction was stopped by addition of 10% FBS and the solution was passed sequentially through 70 µm and 20 µm filters (Gorlitz, Germany). The flow through was then pelleted by centrifugation for 5 min at 1500 rpm and rinsed with the following growth media: DMEM/F12 supplemented with 1M HEPES, 20 mg/ml androstenedione, 4 mg/ml hydrocortisone, 6.5 µg/ml insulin, 6.5 µg/ml transferrin, and 6.5 ng/ml selenium (Sigma-Aldrich, St. Louis, Mo.). The cells were pelleted again and rinsed with growth media containing 10% heat-inactivated FBS. Cells were then resuspended in 1-2 ml of growth media with FBS and plated in 96-well polystyrene plates at an approximate density of 50,000 cells per well. Cells were incubated overnight at 37° C. in a humidified atmosphere of 5% $CO_2$ in air. The following day the media was replaced with growth media containing different concentrations of CE. Growth media was changed every other day, and the MTS CellTiter 96 Aqueous Non-Radioactive One Solution Assay (Promega Corp., Madison, Wis.) was used to evaluate cell viability on day 4 of culture according to the manufacturer's instructions.

HeLa Cell Culture and Survival

Human cervical cancer cells (HeLa cell line; ATCC, Manassas, Va.) were thawed and plated in 96-well plates at an approximate density of 50,000 cells per well. CE exposure and the cell viability assay were performed exactly as described for stromal cells. The only modification was that the cell viability assay was performed on Day 2 for HeLa cells since they proliferate more rapidly than primary cell lines.

Statistical Analysis

Plotting of results and statistical analysis was done using Graph Prism (La Jolla, Calif., USA). Antral cavity formation, estradiol production, and survival following CDDP and CTX exposure were analyzed using a two-way analysis of variance (ANOVA) followed by a Bonferroini posttest for single time point comparisons. HeLa cell, stromal cell, and follicle survival were determined by sigmoidal dose-response (variable slope) curve followed by an F-test. Meiotic progression and spindle morphology were analyzed using a one-way analysis of variance (ANOVA). In all cases, a p-value of less than 0.05 was considered statistically significant.

Figure 8:
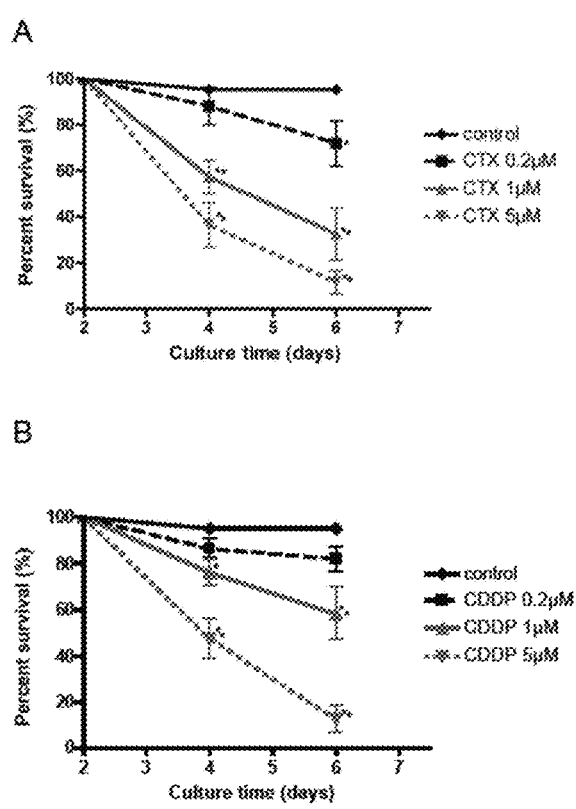
FIG. 8. Validation of the IVFG system using two chemotherapeutics known to have adverse reproductive effects. The effects of increasing concentrations of CTX and CDDP on follicle (A,B) survival and (C,D) morphology during IVFG are shown. Follicles were treated with CTX and CDDP on day 2 of culture, and follicle survival and morphology were assessed on days 4 and 6. The arrowheads highlight the antral cavity, and the arrow indicates an oocyte that has been released from the follicle. Scale bar=100 μm.
Figure 8:
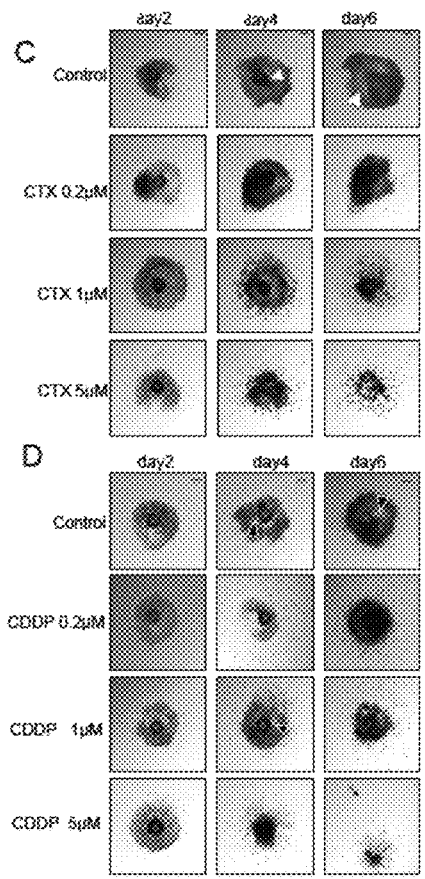

IVFG can be Used to Identify Chemicals that have Potential Adverse Reproductive Outcomes To confirm the utility of the IVFG system, we validated the assay by determining the effects of two common chemotherapeutics, cyclophosphamide (CTX) and cisplatin (CDDP), that are known to be toxic to the ovary and to follicles specifically (Kerr et al. 2012, Hartmann and Lipp 2003; herein incorporated by reference in their entireties). Isolated stage 5b mouse follicles were grown in the presence of 0.2, 1, 5 μM CTX and CDP, and survival rate was quantified based on follicle morphology (FIG. 8). Follicle survival decreased in a dose-dependent manner during culture in CTX and CDDP. Exposure to 1 μM and 5 μM CTX resulted in a significant decrease in survival, from 95.40% to 57.23% and 36.41%, respectively, compared to control follicles by day 4 (FIG. 8A; P<0.001). By day 6, this decrease in survival was even more pronounced with only 32.43% and 11.49% follicles surviving in the 1 μM and 5 μM CTX treatment groups, respectively. At this time, the difference in survival between follicles cultured in 0.2 μM CTX compared to control was also statistically significant (FIG. 8A; 71.8% and 95.40%, respectively, P<0.05). A similar trend in decreased follicle survival after 4 and 6 days of culture was observed following CDDP treatment compared to control follicles (FIG. 8B). This survival reduction due to CDDP exposure, however, was only significant at the 1 μM and 5 μM doses (FIG. 8B; 76.31 and 47.83% on day 4 and 58.38% and 12.56% on day 6, respectively, P<0.05 compared to control). The data imply that increasing concentrations of both CTX and CDDP adversely impacted follicle survival.

In addition to survival, CTX and CDP exposure also affected follicle morphology. In control follicles grown without CDDP or CTX, granulosa cells proliferated and differentiated into mural and cumulus cells concomitant with antral cavity formation (FIGS. 2C, D). In contrast, increasing concentrations of CTX and CDDP resulted in disorganized follicles with dark granulosa cells and little evidence of antral cavity formation (FIGS. 2C, D). The most severe phenotype, observed first at 1 μM CTX and 5 μM CDDP, was the complete release of the oocyte from the follicle (data not shown and FIG. 8D).

Figure 9:
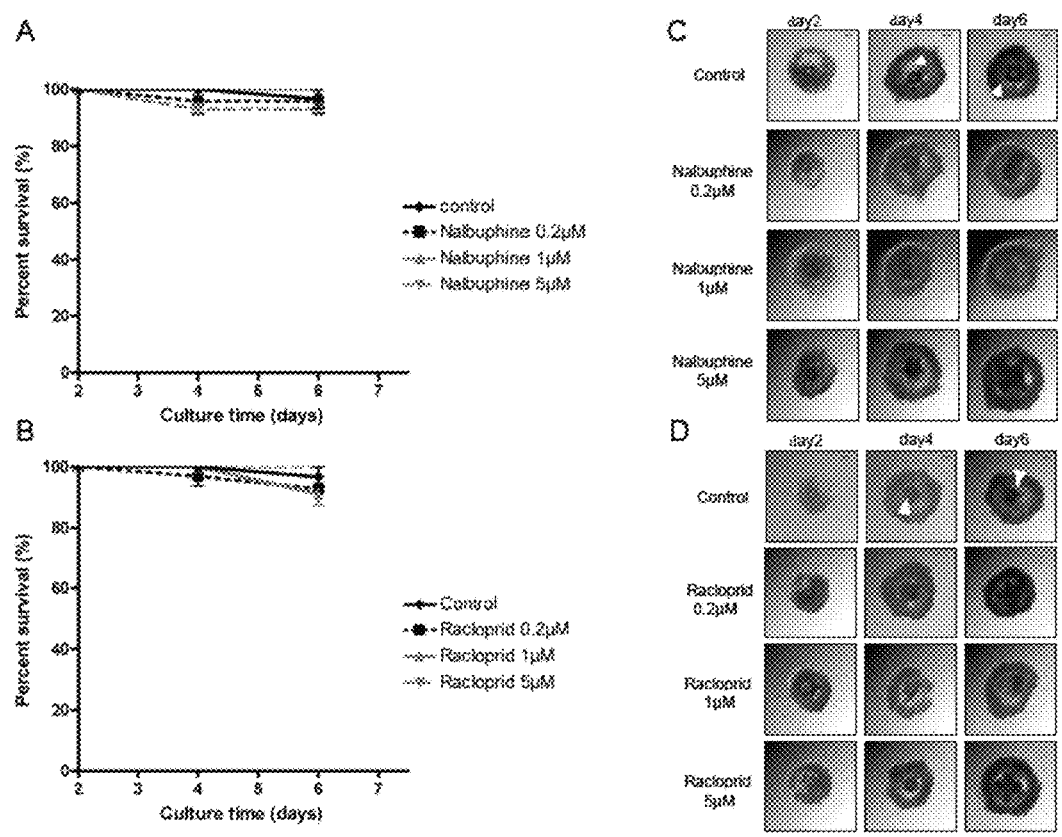
FIG. 9. Validation of the IVFG system using two FDA-approved pharmaceuticals that are not known to have off-target reproductive effects. The effects of increasing concentrations of Nalbuphine and Raclopride on follicle (A, B) survival and (C, D) morphology during IVFG are shown. Follicles were treated with Nalbuphine and Raclopride on day 2 of culture, and follicle survival and morphology were assessed on days 4 and 6. The arrowheads highlight the antral cavity. Scale bar=100 μm.

To confirm that the follicle morphology and survival results obtained following CTX and CDDP exposure were specific and not simply due to a general toxicity response, follicles behavior was examined, when exposed to two FDA-approved pharmaceuticals, Nalbuphine and Raclopride that, unlike CTX and CDDP, have no known documented reproductive toxicity (Borovskaya et al. 2004; Kenney et al. 2001; Kociba and Sleight 1971; Meirow et al. 1999; Meirow and Nugent 2001; Miller 1980; Sklar 2005; Wallace et al. 1989; Yanulevich 1983; Yeh et al. 2006; Yucebilgin et al. 2004; herein incorporated by reference in their entireties). Stage 5b mouse follicles cultured in the presence of 0.2, 1, 5 μM Nabulphine and Raclopride, in contrast to those grown in the presence of CTX and CDDP, were similar to controls in terms of survival and morphology (FIG. 9; P>0.05). Thus, this IVFG system can distinguish differences in how specific chemical exposures influence follicle health and survival.

Dose-Dependent Corexit Exposure Impacts IVFG Reproductive Endpoints

Figure 10:
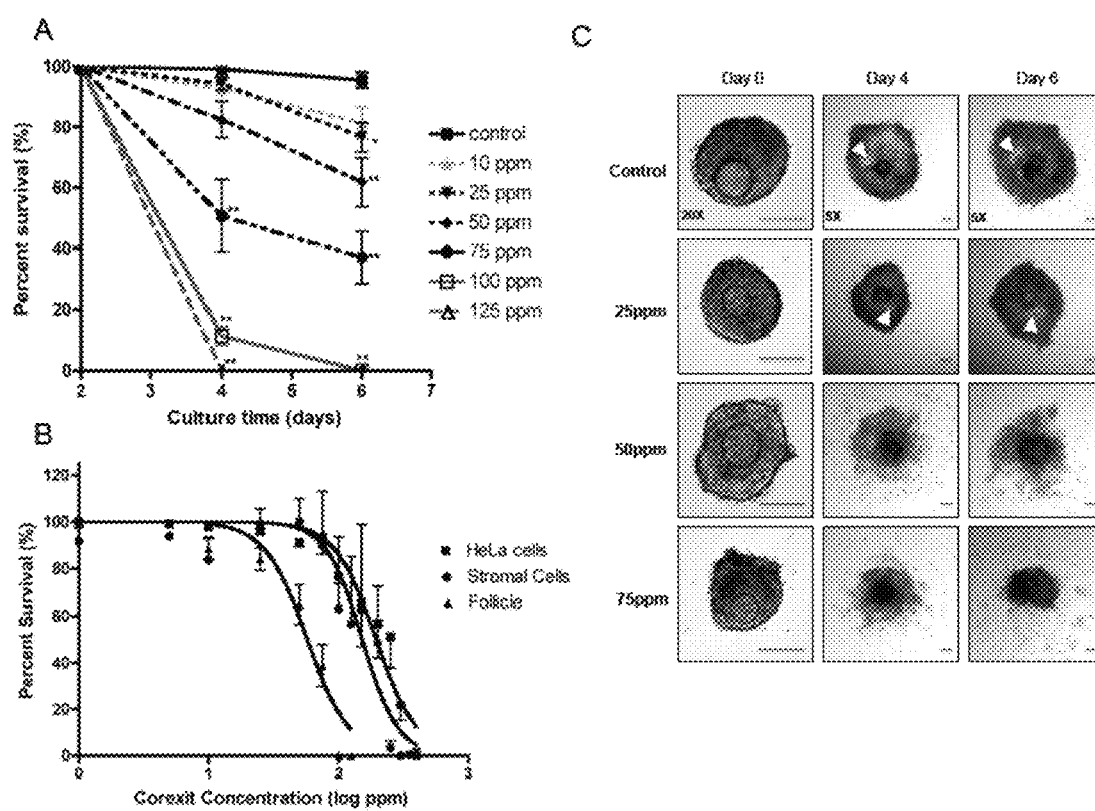
FIG. 10. CE exposure affects ovarian follicle growth and morphology. The effect of increasing concentrations of CE on (A) follicle survival is shown. (B) The survival of follicles, primary ovarian stromal cells, and transformed HeLa cells following culture in increasing concentrations of CE was used to calculate the respective LC50 for each cell type. (C) The effect of CE exposure on follicle morphology is shown. For these experiments, follicles were treated with CE on day 2 of culture, and survival and morphology were assessed on days 4 and 6. The arrowheads highlight the antral cavity. Scale bar=100 μm.

To determine the effect of CE on follicle growth and function, follicles were exposed to increasing concentrations of CE, ranging from 0 ppm to 400 ppm. Overall follicle survival decreased significantly in a dose-dependent manner (FIG. 10A). By day 4 of culture, for example, survival decreased from 99.08% in control follicles to 50.76%, 11.30% and 0% in follicles cultured in 75 ppm, 100 ppm and 125 ppm CE, respectively (FIG. 10A; P<0.001). By day 6, this decrease in survival was even more pronounced with 37.10% and 0% follicles surviving in the 75 ppm and 100 ppm CE treatment groups, respectively. At this time, the difference in survival between follicles cultured in 25 and 50 ppm compared to control were also statistically significant (FIG. 10A; 76.64%, P<0.05 and 61.83%, P<0.001, respectively). Based on these data it was determined that the concentration at which half of the follicles survived at day 6, or the median lethal dose ($LD_{50}$) with 95% confidential interval, was 57.37±8.94 ppm (FIG. 10B, triangles). Given this $LD_{50}$, subsequent experiments were done with CE concentrations of ≤75 ppm.

In addition to affecting follicle survival, exposure to increasing concentrations of CE altered follicle morphology and cellular differentiation (FIG. 10C). Follicles grown in 10 ppm CE appeared morphologically normal and indistinguishable from controls, demonstrating appreciable granulosa cell proliferation and antral cavity formation (data not shown). Follicles exposed to 25 ppm CE also appeared healthy, but their antral cavities appeared smaller compared to those in control follicles (FIG. 10C). In contrast, exposure to 50 ppm and 75 ppm CE resulted in severe follicle disorganization (FIG. 10C).

Figure 11:
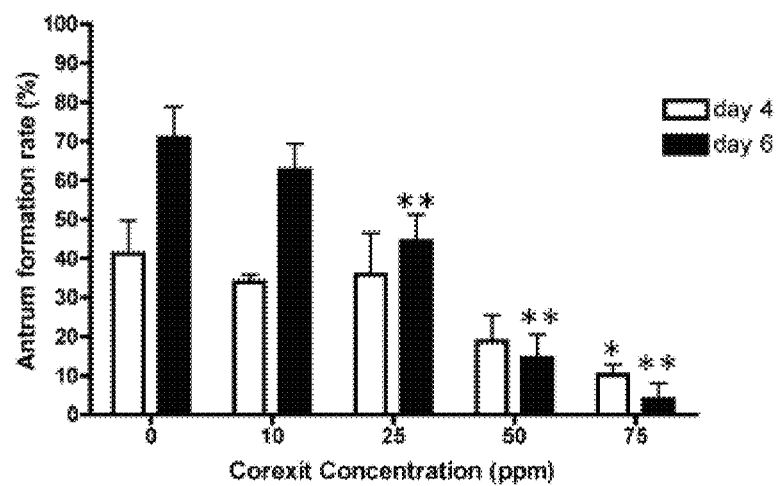
FIG. 11. CE exposure affects follicle differentiation and function. The effects of increasing concentrations of CE on (A) antral cavity formation and (B) estradiol production are shown. These experiments were repeated at least five times with a total of between 51 and 135 follicle examined per CE dose. Follicles were treated with CE on day 2 of culture, and antral cavity formation and hormone production were assessed on days 4 and 6.
Figure 11:
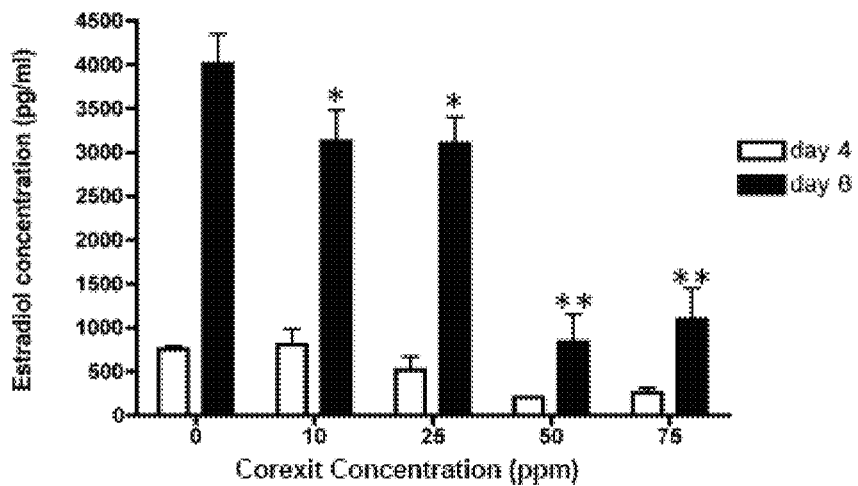

To better understand how CE affected follicle growth and morphology, the percent of follicles that formed antral cavities when exposed to the dispersant was quantified (FIG. 11A). Antral cavity formation was assessed between day 4 and 6 of culture, as this is when many follicles form this characteristic structure (FIGS. 2B, 2D, 4C). On day 4 of culture, only follicles grown in 75 ppm CE showed a significant reduction in antral cavity formation compared to control (FIG. 11A, 10.15% vs. 41.18%, respectively; P<0.05). By day 6, however, significant reductions in antral cavity formation were also observed at lower concentrations of CE. For example, even at 25 ppm CE, the percentage of follicles that formed an antral cavity was 44.4% compared to control follicles in which it was 77.6% (FIG. 11A, P<0.001). In control follicles, a significant increase in the percent of follicles that form antral cavities occurs between day 4 and day 6 of culture (FIG. 11A, 41.18% to 70.84%, respectively; P<0.05). However, when antral cavity formation was compared between day 4 and day 6 for each CE concentration, it was found that this increase did not occur when follicles were exposed to CE concentrations greater than 25 ppm (FIG. 11A). Taken together these data, therefore, indicate that CE exposure has a dose-dependent effect on follicle morphology, with a specific consequence on cellular differentiation and antral cavity formation.

Corexit Exposure Affects Follicle Hormone Production

A major hallmark of follicle function is the ability of the granulosa cells to synthesize steroid hormones (Zeleznik 2004; herein incorporated by reference in its entirety). Therefore to determine how CE exposure affected follicle function, we measured estradiol production in the spent culture media as estrogen is secreted by growing follicles and its concentration increases with follicle development and differentiation (Cortvrindt and Smitz 2002; herein incorporated by reference in its entirety). Estradiol levels were low on day 4 but increased dramatically by day 6, coincident with the large increase in follicle growth and differentiation that is also observed during this time (FIGS. 4C, 5). CE exposure on day 4 did not have a significant effect on baseline estradiol levels. However, at day 6 of culture, CE exposures of 10 ppm and 25 ppm resulted in a slight but significant reduction in estradiol production compared to control (3127 pg/ml and 3097 pg/ml compared to 4007 pg/ml, respectively, p<0.05; FIG. 11B). This negative impact on estradiol production was even more dramatic at CE concentrations of 50 ppm and greater where estradiol production was only between 842.9 pg/ml and 1094 pg/ml, p<0.001; FIG. 11B). In fact the large relative average increase in estradiol production, which typically occurs between day 4 and day 6, was abrogated significantly in follicles cultured in ≥50 ppm CE (p<0.05; FIG. 11B). These results indicate that similar to follicular morphology and development, CE exposure influences hormonal homeostasis.

Corexit Exposure Causes Meiotic Defects in the Oocyte

Figure 12:
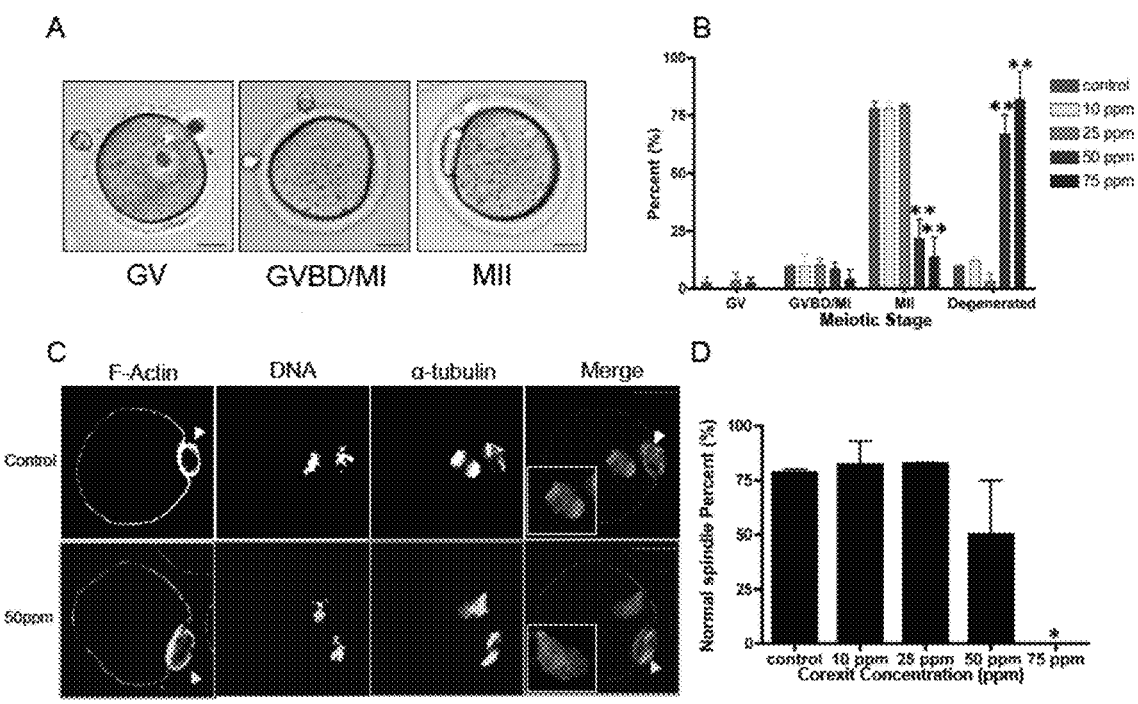
FIG. 12. CE exposure affects oocyte meiotic competence and spindle morphology. The ability of oocytes derived from follicles exposed to CE to progress through the stages of meiotic maturation was (A) scored by light microscopy and (B) quantified. Cells were classified as germinal vesicle intact (GV), germinal vesicle breakdown/metaphase of meiosis I (GVBD/MI). metaphase of meiosis II (MII), and representative images for each stage are shown (A). This experiment was repeated at least twice and a minimum of 25 cells were analyzed in each experimental group. (C) The actin- and microtubule-based cytoskeleton in the resulting MII eggs from control and CE-exposed follicles was examined by immunocytochemistry and confocal microscopy. An optical section encompassing the meiotic spindle is shown. Normal meiotic spindles were characterized by a bipolar structure with chromosomes tightly aligned on the metaphase plate (upper panel, control). Abnormal spindles were characterized by disrupted tubulin and scattered chromosomes (lower panel, 50 ppm CE). (D) The percent of normal spindles observed in the MII eggs derived from follicles exposed to increasing concentrations of CE was quantifiedArrowheads indicate the polar body. Scale bar=25 μm.

In addition to producing hormones that support follicle development and endocrine feedback, a prime function of the ovarian follicle is to produce a healthy female gamete. One hallmark of a fully-grown oocyte is its ability to resume meiosis and reach MII in response to gonadotropin stimulation. It was examined how CE exposure during IVFG impacted this process, also referred to as meiotic maturation. To do this, meiotic resumption was stimulated in follicles that had been exposed to different doses of CE on day 6 and then scored meiotic progression. The categories that were scored GV, GVBD/MI, and MII which correspond to the following meiotic stages: prophase I-arrested, prometaphase I or metaphase I, and metaphase II, respectively (FIG. 12A). The number of cells that were degenerated was also scored. Only those cells that have completed the first meiotic division with emission of the first polar body and reached MII have the ability to be fertilized (Ducibella and Buetow 1994; herein incorporated by reference in its entirety). In control follicles that were not exposed to CE, 78%±4.243% of the gametes reached MII (FIG. 12B). This percentage was unchanged in follicles that were exposed to 10 ppm and 25 ppm of CE. However, at 50 ppm and 75 ppm only 21.80% and 13.90% of the oocytes reached MII, respectively (p<0.001; FIG. 12B). This decrease in mature gametes was instead accompanied by a significant increase in the percent of degenerated cells (FIG. 12B). CE exposure did not affect the percentage of cells that were in the GV or GVBD/MI stage (FIG. 12B). These data imply that at higher concentrations, CE negatively impacts the ability of the follicle to produce a viable and mature egg.

Figure 6:
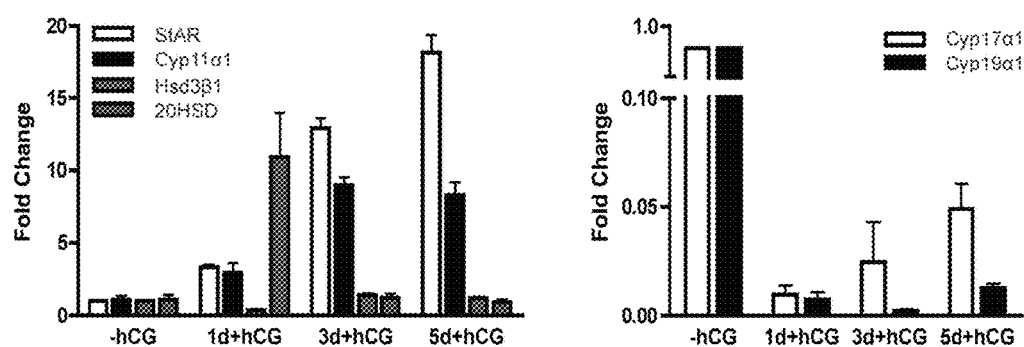
FIG. 6. Murine hCG transcriptional control of steroid and peptide hormones. qRT-PCR was performed on RNA isolated from follicles before (-hCG) and after hCG treatment (1 d, 3 d, and 5 days post-hCG), n=2-3 cultures per time point. (A) As reported in vivo, transcripts for the steroidogenic enzymes Star, Hsd3b1, and Cyp11a1 were significantly induced post-hCG. 20αHsd, the enzyme predominately responsible for progesterone catabolism in the rodent, was upregulated. The enzymes responsible for androgen and estrogen synthesis, Cyp17a1 and Cyp19a1, respectively, were significantly downregulated post-hCG. (B) Expression of the gonadotropin receptors genes (Fshr and Lhcgr) also mimicked in vivo patterns, with an overall downregulation 3 days post-hCG; (C) Transcription factors known to downregulate inhibin α-subunit expression in the mouse were induced post-hCG.
Figure 6:
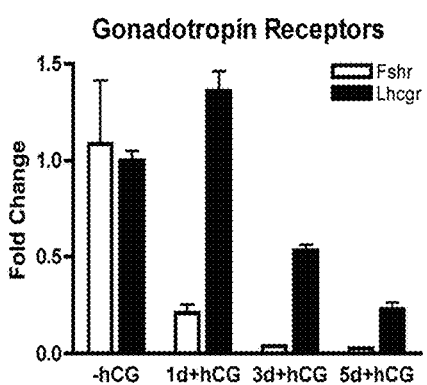
Figure 6:
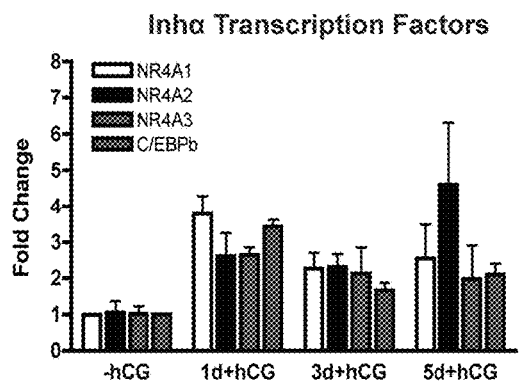
Figure 7:
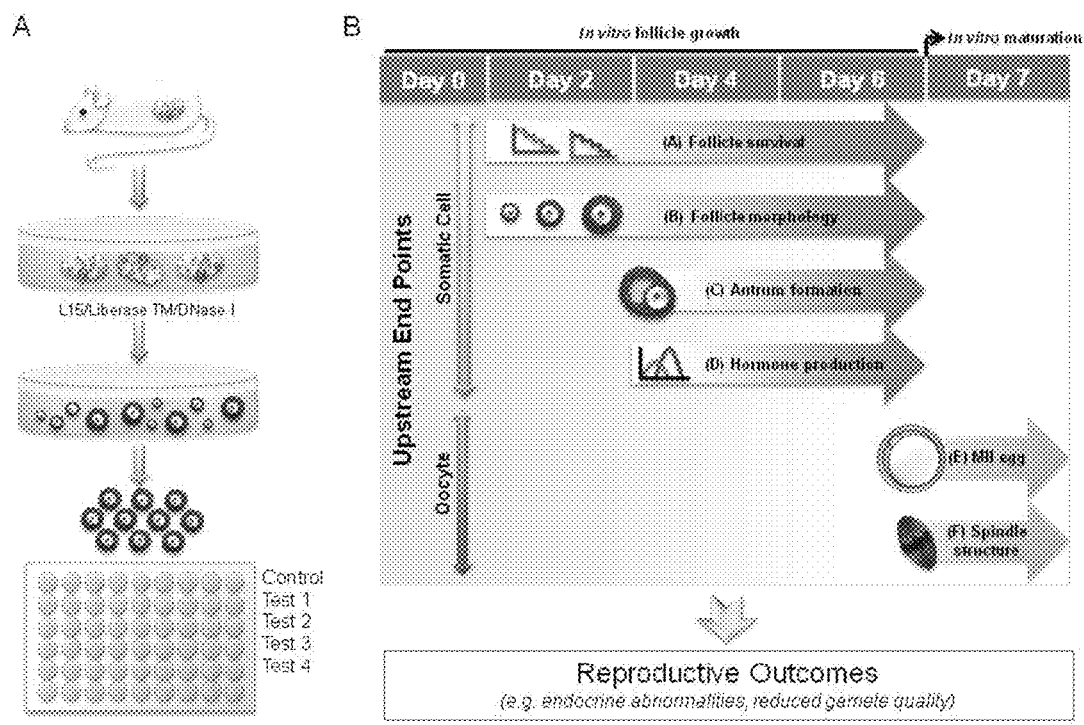
FIG. 7. In Vitro Follicle Growth (IVFG) provides a simple and rapid method of predicting adverse reproductive outcomes in mammals in response to environmental exposures. In IVFG, (A) large numbers of ovarian follicles are collected from pre-pubertal mouse ovaries and placed individually in wells of a 96-well plate containing chemicals of interest. Follicles are cultured and monitored for up to 6 days. (B) Upstream endpoints of IVFG include: (i) follicle survival, (ii) follicle morphology, (ii) antrum formation, (iv) hormone production, (v) oocyte meiotic competence, and (F) spindle structure. These hallmarks are robust biomarkers of both endocrine and gamete quality.

Although CE doses of 50 ppm and 75 ppm significantly compromised meiotic maturation, there were still some MII eggs produced. To better understand the quality of the resulting eggs, a more detailed analysis of their cytoskeleton morphology was performed (FIGS. 6C, D). Specifically the structure of the meiotic spindle and cortical actin following exposure to increasing CE concentrations was examined (FIG. 12C). A healthy egg has a symmetric and bipolar spindle with chromosomes tightly aligned on the metaphase plate (Lenie et al. 2008; herein incorporated by reference in its entirety). Such a structure is essential for mediating proper chromosome segregation upon fertilization to produce a haploid female gamete. In addition, the actin cytoskeleton is cortical and polarized in the region overlying the meiotic spindle and chromosomes. No differences in spindle structures in MII eggs from follicles exposed to 10 ppm and 25 ppm CE were observed compared to controls. However, abnormal spindles were observed following exposure to higher concentrations of CE (FIGS. 6C, D). In follicles grown in 75 ppm CE, no normal spindle morphology was observed in the resulting eggs. Instead spindles in these eggs lacked an organized bipolar structure and had significant chromosome misalignment (FIG. 12C). In contrast to the meiotic spindle which appeared to be highly sensitive to CE, cortical F-actin was not (FIG. 12C).

The Ovarian Follicle is More Sensitive to Corexit than Cell Lines

In toxicity studies, cell lines are often used for in vitro drug screening and toxicity studies (Allen, et al 2005; herein incorporated by reference in its entirety). Primary ovarian stromal cells and HeLa cells were grown in CE concentrations ranging from 5 ppm to 400 ppm and quantified their survival using a cell viability assay. For both primary ovarian stromal cells and HeLa cells, the data was fit to a variable sigmoidal dose-response curve and an F-test was performed to determine significance (p<0.0001; FIG. 12B). It was calculated that the $LD_{50}$ with 95% confidential interval for primary ovarian stromal cells was 151.9±32.25 ppm and that for HeLa cells was 194.1±22.8 ppm. This observed difference in survival between HeLa cells and primary ovarian stromal cells was statistically significant (p<0.05). Moreover, the $LD_{50}$ of follicles was significantly lower than either of the somatic cell counterparts examined (p<0.0001; FIG. 12B). These data highlight distinct differences in how cells behave in response to CE and suggest that transformed cells are more resistant than primary cells. Moreover, the ovarian follicle—which contains both somatic and germ cell components—is particularly sensitive to CE.

Example 3

Human Fallopian Epithelium Response In Vitro to Mimetic of the Human Menstrual Cycle The human fallopian tube (named oviduct in non-primate species) is a critical organ in the female reproductive tract that facilitates the transport of the cumulus-oocyte complex (COC), sperm, and embryos (Hunter, 2005; herein incorporated by reference in its entirety). The oviduct consists of distinct segments that contribute to the process of gamete transport and fertilization including the fimbriated ends that lie adjacent to the ovary, the ampulla, the ampulla-isthmus junction, and the isthmus portion (Croxatto, 2002; herein incorporated by reference in its entirety). The fimbriae wrap around the ovary and transport the COC into the ampulla portion (Croxatto, 2002; herein incorporated by reference in its entirety). The isthmus primarily participates in the binding and release of spermatozoa through a series of specific carbohydrate residues that generate a sperm reservoir (Talbott et al., 2003; herein incorporated by reference in its entirety). The embryo also transiently attaches to the oviductal epithelium and is transported to the uterus for implantation (Velasquez et al. 2001; herein incorporated by reference in its entirety). Therefore, understanding oviductal biology using proper in-vitro models is crucial to improving reproductive health.

The entire epithelium is regulated by hormones as well as by the gametes and the embryos that interact with the epithelium (Abe et al, 1999; Bauersachs, 2004). Estrogen and progesterone bind to their receptors, ER and PR, in the epithelium to induce alterations in gene function such as, oviductal glycoprotein 1 (OVGP1), IGF1, and ciliary beating (Bylander, 2010; Mahmood, 2008; Nakahari, 2011; herein incorporated by reference in their entireties). OVGP1, which is secreted in response to estrogen, positively influences the capacitation of sperm and its motility during fertilization (Erickson-Lawrence, et al.; 1989; Verhage et al., 1997; Verhage et al., 1990; herein incorporated by reference in their entireties). Experiments were conducted during development of embodiments of the present invention to demonstrate functional biological stimulation of primary human fallopian tube cultures to the menstrual cycle. The culture system for the first time integrates the biology of the maturing ovarian follicle with the downstream biological function of the fallopian tube in terms of cilia action, gene expression, and secreted factors.

Figure 13:
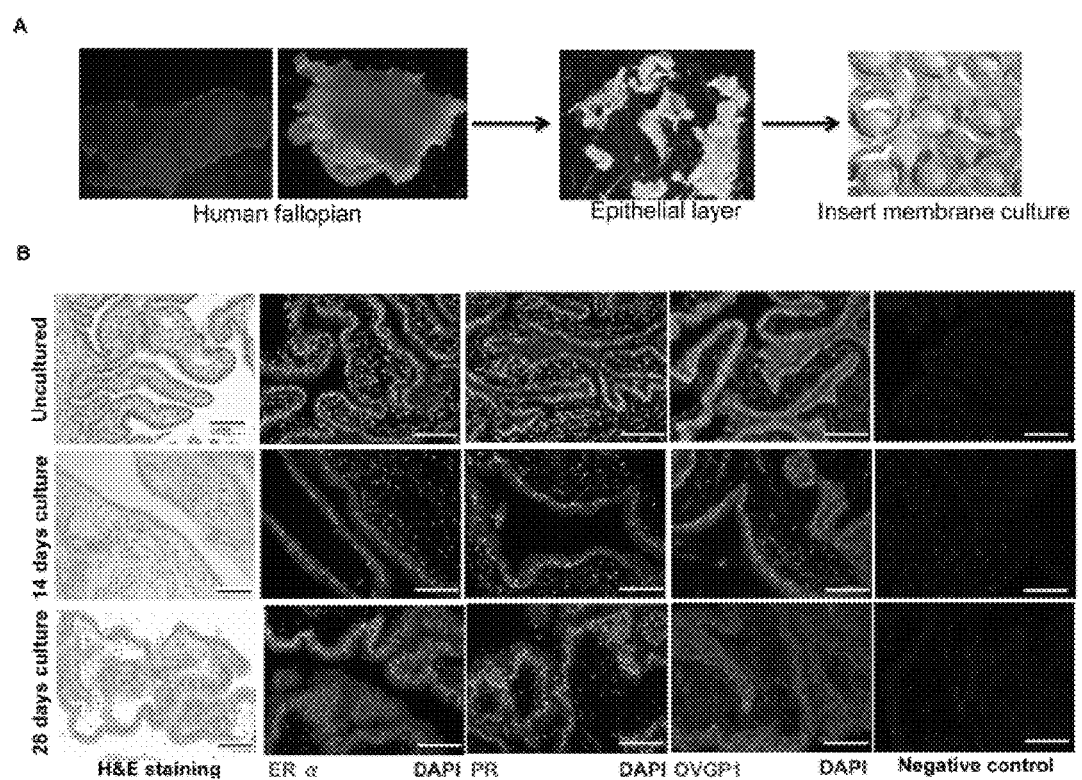
FIG. 13. 3D human fallopian tube in-vitro culture on TRANSWELL membrane inserts maintains tissue architecture and viability. (A). The human fallopian tube was cut open and the epithelia layer was mechanically isolated. The epithelia layer was cut into 2×2 mm pieces and cultured on the insert membrane. (B) The epithelia layer was treated with low dose of E2 0.1 nM for 14 days and 28 days. H&E staining was used to evaluate the morphology of human fallopian tube epithelial cells after 14 and 28 days in culture compared with uncultured tissue. ERα, PR and OVGP1 immunofluorescent staining were performed to characterize the human fallopian epithelia culture system. Scale bar indicates 100 um size.
Figure 14:
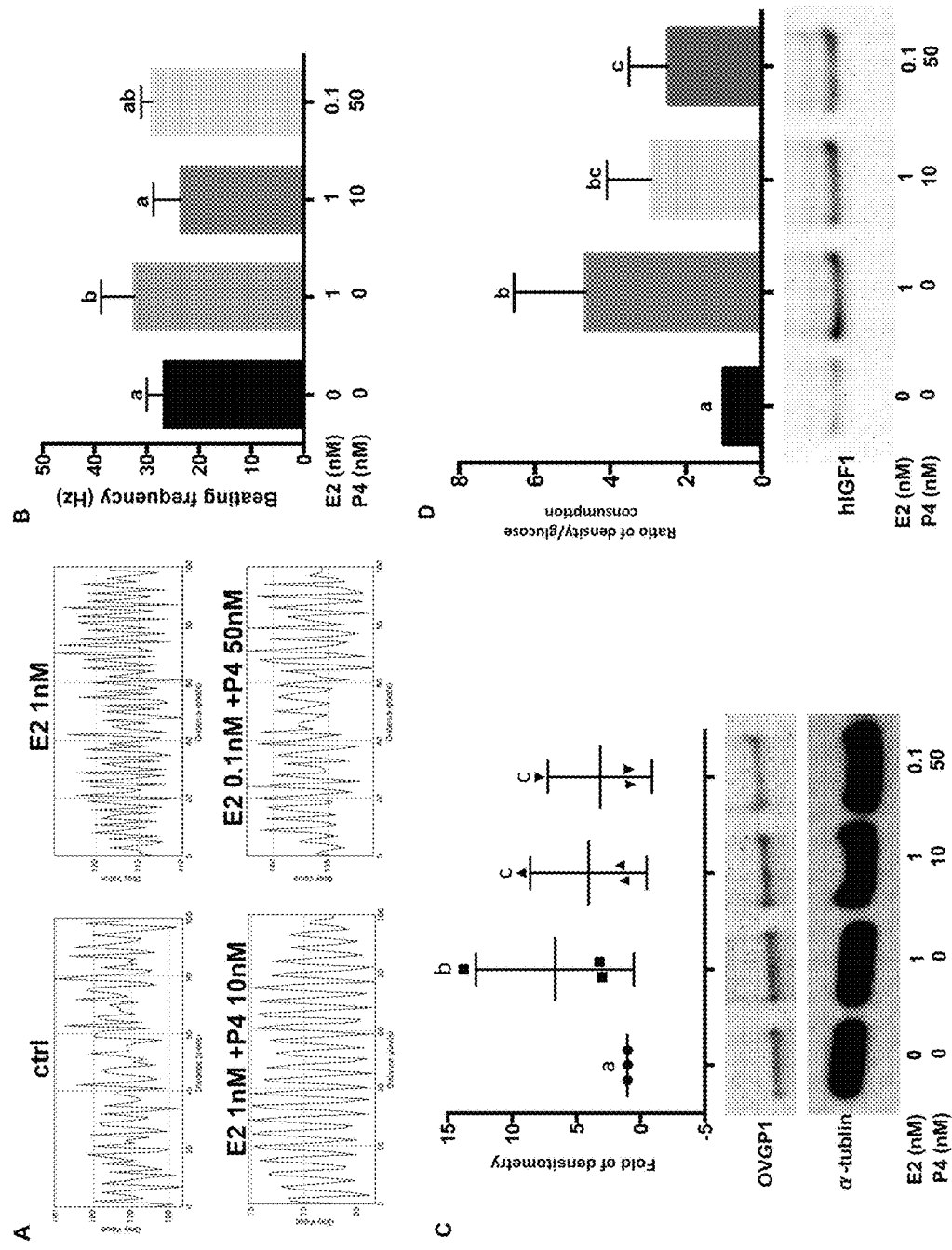
FIG. 14. Functional response of human fallopian tube epithelium to culture in the presence of E2 and P4. (A), (B) After 7 days of culture in the indicated treatments, cilia beating frequency was measured using an Andor spin disk microscope with a 100× objective and a 5 ms exposure time and 5 ms readout time. (A) Graphs depict a representative measurement of cilia beating frequency in cultured fallopian epithelium from 1 patient. (B) Quantification of cilia beating frequency for n=3 fallopian endometrium cultures from 3 individual women. (C) Immunoblot of OVGP1 expression in cultured fallopian epithelium after treatment for 7 days. Bar graph represents relative band density using α-tubulin as the loading control for n=4 cultured fallopian endometrium lysates from 4 women. (D) Conditioned medium from fallopian epithelium cultures was used to quantify hIGF1 levels by immunoblot analysis. Bar graph represents relative band density using glucose consumption as a loading control for n=3 conditioned medium samples from fallopian tissue cultures from 3 women. "*" corresponded to statistically significant differences between groups. A one-way ANOVA followed by Tukey's multiple comparisons test was used for statistical analysis, and $P<0.05$ was considered statistically significant.

Human fallopian epithelia layers, which included epithelia cells and stromal cells, were cultured for 28 days on TRANSWELL membrane inserts (FIG. 13A). The epithelium structure was clearly identifiable and maintained strong ERα, PR, and OVGP1 expression after culture for 28 days (FIG. 13B). In order to study functional changes in the human fallopian epithelia tissue in response to human sex steroids, the menstrual cycle was divided into four seven day blocks as follows: low E2 (0.1 nM) and high E2 (1 nM) to mimic the follicular phase; E2 1 nM+P4 10 nM and E2 0.1 nM+P4 50 nM to mimic the luteal phase (Baerwald, 2012; herein incorporated by reference in its entirety). Using the human fallopian epithelial culture system cilia beating frequency, OVGP1 expression and IGF1 secretion were stimulated by E2 and suppressed by P4 (FIG. 14) (Mahmood et al., 1998; Verhage et al., 1990; Shao et al., 2007; herein incorporated by reference in their entireties). Cilia beating was maintained after 7 days in culture. Cilia beating frequency (CBF) significantly increased with E2 treatment, and decreased upon the addition of P4 (FIG. 14A, B). OVGP1 expression in the fallopian lysate also demonstrated induction from E2 treatment, and was suppressed by the addition of P4 (FIG. 14C). Similar to OVGP1 expression and CBF, IGF1 secretion was induced by 1 nM E2 and attenuated by the addition of P4 (FIG. 14D). These data indicate that human fallopian epithelium cultured on microporous membrane inserts can be used to model biological responses to hormonal stimulation.

Figure 15:
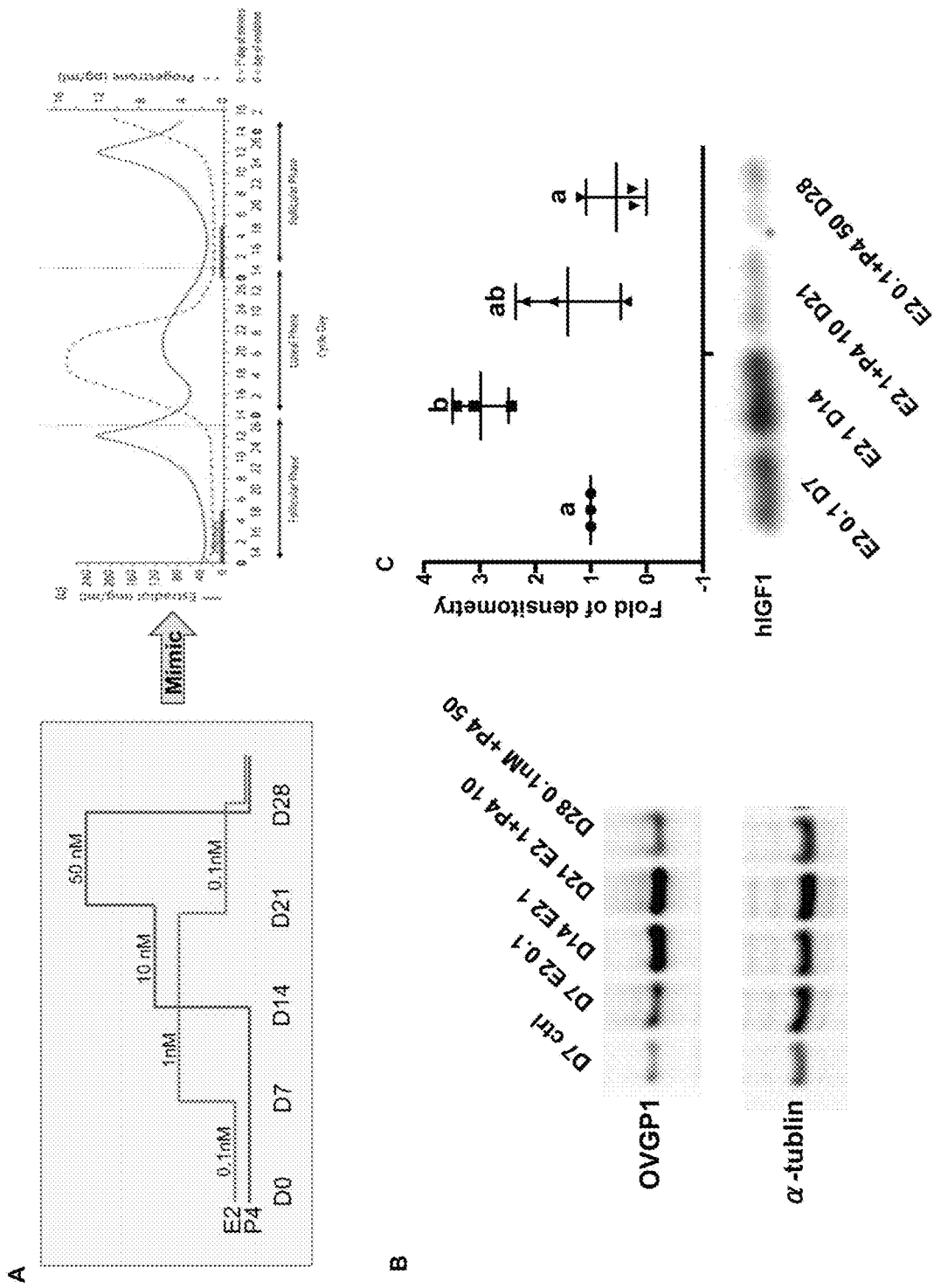
FIG. 15. Stepwise exogenous steroid hormone treatment for 28 days regulates OVGP1 and hIGF1 in human fallopian tube epithelium. (A) Stepwise exogenous E2 and P4 treatments used to mimic the human menstrual cycle. (B) Cultured fallopian epithelium was collected on the indicated day and lysate was analyzed for OVGP1 protein expression by immunoblot. α-tubulin was used as loading control. (C) Conditioned medium from fallopian endometrial cultures was analyzed by immunoblot for hIGF1 expression every 7 days. n=3 experiments with conditioned media from fallopian tissue cultures from 3 women. Relative density of each band was based on E2 0.1 nM treatment group. "*" corresponded to statistically significant differences between groups. A one-way ANOVA followed by Tukey's multiple comparisons test was used for statistical analysis, and $P<0.05$ was considered statistically significant.

The previous section demonstrated that human fallopian tube grown on microporous membrane inserts functionally responded to combinations of estrogen and progesterone over 7 days. Next, a stepwise increase in steroid hormones was designed to mimic the human menstrual cycle over 28 days (FIG. 15A). Similar to individual 7 days cultures, the prolonged culture, exposed to the menstrual cycle in these four stages, demonstrated that OVGP1 (FIG. 15B) and IGF1 (FIG. 15C) were both stimulated by E2 and suppressed by the addition of P4 in the presence of E2.

Figure 16:
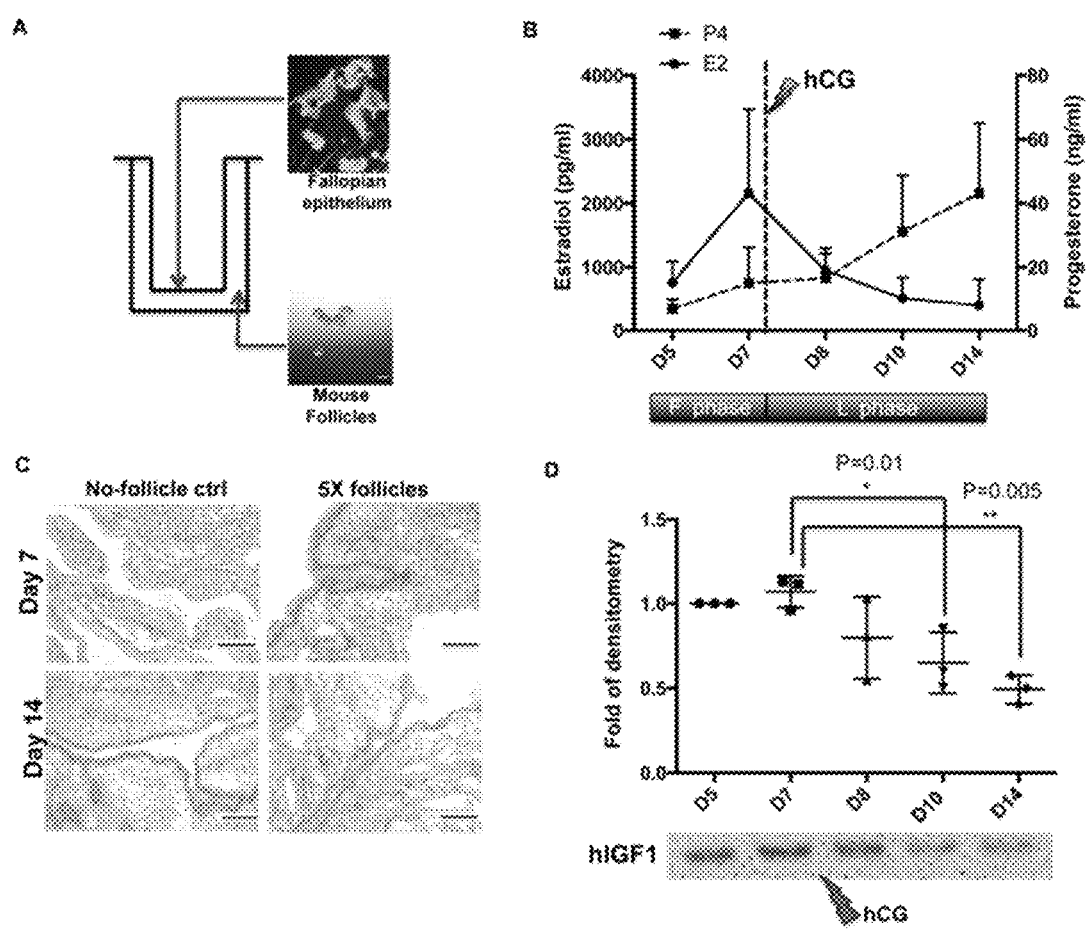
FIG. 16. Human fallopian epithelium and murine follicle co-culture induces morphological changes and protein secretion. (A) Schematic of follicle and fallopian epithelium co-culture model. Five Secondary follicles (150 μm-180 μm) were encapsulated into a single 0.5% alginate bead, which was placed in the bottom of each well. Fallopian epithelium was cultured on a 0.4 μm insert membrane, which was placed into the 12-well plate containing encapsulated follicles. (B) E2 and P4 concentrations from the co-culture medium. The co-cultures were maintained in growth medium supplemented with 10 mIU/ml recombinant human follicle-stimulating hormone (rhFSH) for 7 days. After 7 days, the follicles were treated with 1.5 IU/ml hCG for 16 hours to induce in vitro maturation. The luteinized follicles were then cultured for another 7 days without rhFSH. "F phase" represents follicular phase, "L phase" represents luteal phase. (C) Morphology of the fallopian epithelial tissue cultured alone or co-cultured with follicles for 7 days and 14 days. Scale bar=100 μm. (D) hIGF1 levels were measured in the conditioned medium by immunoblot analysis. Bar graph represents relative band density compared to culture day 5. Three individual experiments were performed using fallopian tissues from 3 women. "*" Corresponded to statistically significant differences between groups. One-way ANOVA followed by Tukey's multiple comparisons test was used for statistical analysis, P<0.05 was considered statistically significant.

Maturing ovarian follicles secrete hormones that dictate the fluctuations of the menstrual cycle. In vitro maturation of follicles in alginate hydrogels can support the growth and steroidogenic function of the in vivo follicle (Xu, et al., 2006A; Xu, et al., 2006B; Xu, et al., 2007; herein incorporated by reference in their entireties). Due to the finite and limited access to human ovarian follicles for research, an engineered system of mouse in vitro follicle culture was utilized that demonstrated the ability to mimic the human follicular and luteal phase in terms of steroid hormone and peptide hormone. To test the response of fallopian epithelium tissue insert cultures to physiologic hormone stimulation from ovarian follicles, a co-culture was established (FIG. 16A). Although the cycle was shortened to 14 days, the E2 and P4 pattern in the follicle culture system matched the human menstrual cycle pattern (FIG. 16B). E2 levels rose during the first seven days mimicking the follicular cycle. In-vitro maturation (IVM) was stimulated using hCG on the evening of day 7 promoting an increase in progesterone production during the luteal phase for another seven days. The morphology of fallopian epithelial layers in the co-culture system demonstrated cell viability after 7 days and 14 days of culture (FIG. 16C). Human IGF1 (hIGF1) secretion was used as a functional biomarker of hormone responsiveness for the fallopian tube cultures. hIGF1 expression continually increased before IVM when estrogen levels were high and then declined after IVM indicating progesterone mediated repression (FIG. 16D). Therefore, the human fallopian tube can be co-cultured with the mouse ovarian follicle to better mimic hormone fluctuations that normally occur as part of the human menstrual cycle. In additional embodiments, one could interrogate the follicle and fallopian 3D co-culture system with additional female reproductive tissues in a microfluidic culture system.

The fallopian tube is an important reproductive target for pharmaceutical intervention and access to reliable models of human tissue are essential for preclinical studies that might enhance fertility, provide contraception, reduce ectopic pregnancy, and impact serous cancer formation. The described system used normal human fallopian tube tissue from women undergoing hysterectomy on microporous TRANSWELL inserts with maintenance of viability and hormone receptor expression for up to 28 days in culture. Hormonal fluctuations of the human menstrual cycle were modeled using three different methods. First, estrogen and progesterone were used in four combinations for seven days to mimic the different stages of menstrual cycle. Second, hormone combinations were changed in a step-wise manner to mimic a 28 days menstrual cycle. Lastly, the fallopian tube epithelium tissue were exposed to in vitro cultured mouse follicles engineered to secrete hormones in a manner that phenocopies a shortened human menstrual cycle. Primary human fallopian epithelium maintained ciliated and secretory phenotypes and functionally responded to multiple hormone stimulation procedures through 28 days of culture.

Specifically, estrogen increased OVGP1 expression, IGF1 secretion, and ciliary beating rates, while the addition of progesterone decreased these functional markers. In addition, co-culture of human fallopian epithelia with ovarian mouse follicles proved to be an effective model of fallopian and follicle interactions.

Human fallopian tube was cultured with ovarian murine follicles to model a physiologic source of hormones. Since steroids estrogen and progesterone are conserved across species, the mouse follicle co-culture with the human fallopian epithelium in this study provides a novel approach to not only monitor the response of human fallopian tube cells to follicular fluid from bin vitro matured and ovulated follicles, but also during growth of the follicle. Additional factors in conditioned medium from in vitro matured follicles and follicular fluid, such as prostaglandins (Seibel et al., 1984; herein incorporated by reference in its entirety), can also be monitored in future analysis to determine their role on inflammation and cancer initiation (Levanon et al., 2010; King et al., 2011; herein incorporated by reference in their entireties). These studies provide in vitro confirmation that cultured fallopian tube epithelium responds to the menstrual cycle hormones in a similar manner to tissues collected from women at different stages of the menstrual cycle (Lyons et al., 2002; herein incorporated by reference in their entireties).

In vitro models of fallopian epithelium in the menstrual cycle environment provide an important tool for understanding women's health. The 3D model can be extended to study normal physiology, infertility, and cancer. Effects of environmental toxins, such as cigarette smoke, and pharmaceuticals, such as emergency contraception, on the fallopian epithelium can be studied both dependently and independently of cilia beating (Leng et al., 1998; Knoll et al., 1998; herein incorporated by reference in their entireties). The role of oviductal secretions on sperm capacitation and transport could be uncovered in this model and provide a system for studying new drugs that modulate sperm to enhance or prevent fertilization. Early development of the embryo occurs in the fallopian tube and may be negatively impacted by environmental pollutants or pharmaceutical drugs that can be studied safely in an in vitro human model system. The secretory cells of the fimbria of fallopian tubes are potential sites for serous cancer formation and the role of steroid hormones may influence cancer formation and/or prevention (Corner et al., 1998; Yamanouchi, 2010; herein incorporated by reference in their entireties). The human fallopian tube culture system provides a robust model for studying the biology of these reproductive health concerns. In certain embodiments, one could integrate the fallopian epithelium and follicle cultures with uterine tissues to establish an integrated microphysiologic female reproductive tract for study in combination with non-reproductive tissues providing a whole body model of hormone function.

Human Fallopian Tissue Culture

Human fallopian tissue was obtained from routine hysterectomies from women in their reproductive years (ages range from 26 to 50 years old) and who had not undergone exogenous hormonal treatment for at least three months prior to surgery. Informed consent was obtained from each patient and approval granted by the ethics committee of the Northwestern University. Human fallopian tissue was kept in the DMEM/F12 medium with 10% FBS on ice and processed within 24 hours. The tissue was washed with warm PBS solution two times before being transferred into warm dissection medium (Liebowitz 15 with 0.5% P/S and 10% FBS). After cleaning connective tissue from outside of the fallopian tissue, the fallopian tube was cut open and the inner epithelia layer was mechanically dissected using forceps. The epithelia layer was transferred to phenol red free DMEM/F12 with 0.3% BSA, 1% P/S and ITS (5 μm/ml insulin, 5 μg/ml transferrin, 5 ng/ml selenium) (Sigma-Aldrich, St. Louis, Mo.) medium and cut into 2×2 mm pieces for further culture. Tissue was cultured on 0.4 μm pore Millicell inserts (PICM03050, EMD Millipore Co, Billerica, Mass., USA) twelve-well plates with culture medium in a 37° C. and 5% $CO_2$ incubator. Estrogen (E2) and progesterone (P4) used in tissue culture experiments were purchased from Sigma (St. Louis, Mo.).

Histology

Cultured fallopian epithelia layers were fixed with Modified Davison's fixative (Electron Microscopy Science Inc., Hatfield, Pa.) for 24 h at 4° C. and then processed and embedded in paraffin. H&E staining was performed using standard methods. Immunofluorescence staining (IF) was performed and visualized as previously described (Kim et al., 2013; herein incorporated by reference in its entirety). The primary antibodies used for the IF staining were as follows: ER alpha (Abgen, Pittsburgh Pa.) for 1:70 dilution, PR (Dako, Carpinteria, Calif.) for 1:200 dilution, Ki67 (abcam, Cambridge, Mass.) 1:100 dilution and OVGP1 (LsBio, Seattle, Wash.) 1:100 dilution. Tissue stained without adding primary antibody was used as negative control.

Immunoblot Analysis

Cultured human fallopian epithelia layers were homogenized with a minipestle in ice-cold lysis buffer (20 mM Tris-HCl, pH 8.0, 137 mM NaCl, 10% glycerol, 1% NP-40, 2 mM EDTA). Lysate normalized for protein content was loaded into NuPAGE 4-12% gradient Bis-Tris precast SDS-PAGE gels and transferred to a nitrocellulose membrane (Life Technologies, Carlsbad, Calif., USA). Blots were probed by polyclonal anti-OVGP1 antibody (LsBio, Cambridge, Mass.) overnight in 4° C. followed by anti-rabbit secondary antibody conjugated to horseradish peroxidase (Zymed, San Francisco, Calif.). Proteins were detected by ECL primer (GE HealthCare Life Sciences, Pittsburgh, Pa.) and exposed to X-ray film (Kodak, Rochester, N.Y.). The same blot was stripped using stripping buffer (Thermo Scientific, Hanover Park, Ill.) and re-probed with monoclonal anti-α-tubulin (Sigma, St. Louis, Mo.) followed by an anti-mouse secondary antibody conjugated to horseradish peroxidase. NIH ImageJ Imaging Software was used to quantify the density of western blot bands. Conditioned medium from fallopian epithelia cultures was collected and probed via western blot analysis using a polyclonal anti-hIGF1 anti-body (abcam, Cambridge, Mass.). The blot was detected by the same method described above.

Glucose ELISA

Fallopian epithelia layers cultured on TRANSWELL inserts were pre-cultured in the alpha-MEM with 0.3% BSA, ITS and 1% P/S medium for two days. Cell culture medium was collected for the glucose ELISA assay (abcam, Cambridge, Mass.). Medium was diluted 1:500 and ELISA was performed according to the protocol provided by the kit. Glucose consumption results were used to normalize the hIGF protein secretion in cell culture media to account for slight size differences in cultured fallopian tube epithelial layers.

Fallopian Epithelia Cilia Beating Quantification

Fallopian epithelia layers were cultured in estradiol (E2) 1 nM, E2 1 nM+progesterone (P4) 10 nM, E2 0.1 nM+P4 50 nM or with solvent only negative control for 7 days. Cilia beating movies were acquired using an Andor Spinning Disk Confocal with 5 ms exposure time and 5 ms readout time. Each movie consists of 100 individual frames. Five movies in different areas of the sample were taken. The Multiple Kymograph plugin for the NIH ImageJ software was used to quantify cilia beating frequency. In each movie, 8 clusters of cilia were picked for the cilia beating quantification.

Follicle Co-Culture with Fallopian Epithelia Layer

CD-1 mice were purchased from Harlan Laboratories (Madison, Wis., USA). All procedures involving mice were approved by the Northwestern University Animal Care and Use Committee. Mice were housed and bred in a barrier facility within Northwestern University's Center of Comparative Medicine (Chicago, Ill., USA) and were provided with food and water ad libitum. Temperature, humidity, and photoperiod (14 L:10 D) were kept constant. Day 14 CD1 mice ovaries were removed and 150 um-180 um size follicles were isolated from the ovaries. 5 follicles were encapsulated into 0.5% (w/v) alginate beads for further culture. The alginate bead was placed in one well of a 12 well plate and the fallopian tube epithelial layer tissue was placed on the 0.4 um insert membrane. The insert containing the fallopian tube culture was placed into the same well as the follicle in the alginate bead. Medium in the 12-well co-culture was composed of follicle culture medium, made from alpha MEM with 0.5 mg/ml fetuin (Sigma-Aldrich, St. Louis, Mo.), 0.3% BSA, ITS, and 10 mIU/ml recombinant human FSH supplement for 7 days. On day 7, the medium was changed to in vitro maturation medium, containing 1.5 IU HCG in follicle growth medium for 16 hours. After 16 hours, the medium was changed back to follicle growth medium without rhFSH. The follicles, now luteinized due to exposure to HCG, were continually cultured for another 7 days. Every other day 50 µl of the medium was collected for the E2, P4 ELISA test and western blot for hIGF1. The pictures for the follicles were taken every other day.

Steroid Hormone ELISA

E2 and P4 in follicle culture medium were detected by the E2 and P4 ELISA kit (Calbiotech, CA, USA) using the manufacturer's protocol.

Statistical Analyses

The cilia beating quantification and western blot band densitometry quantification were analyzed using One-way ANOVA followed by Tukey's multiple comparisons test. A p-value less than 0.05 was considered statistically significant.

Example 4

Human Uterine Cultures in 3D Microphysiologic Setting

Experiments were conducted during development of embodiments of the present invention to establish static 3D cultures of uterine cells (e.g., myometrial cells, endometrial epithelial cells, and endometrial stromal cells) and to determine the biological response of the cells in such a system to stimuli such as estradiol and progesterone.

Static 3D cultures of uterine cells are established in Transwell cultures with endometrial epithelial and endometrial stromal cells in the upper chamber and myometrial cells in the lower chamber.

Figure 17:
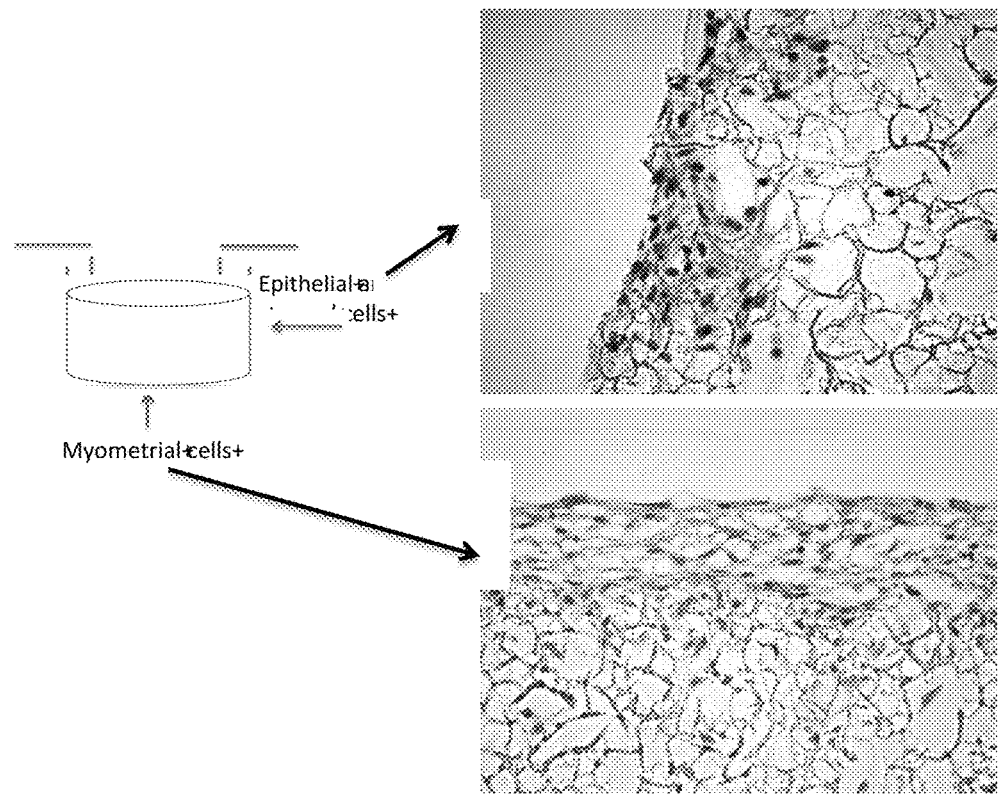
FIG. 17. Establishment of 3D uterine cultures for 28-days. (A) Primary endometrial and myometrial cells were cocultured on polystyrene scaffold and treated with estradiol (E2) and progesterone (P4) in a stepwise fashion; 0.1 nM E2 for 7 days, 1 nM E2 for the next 7 days, followed by 1 nM E2+P4 10 nM for 7 days, then 0.1 nM E2+P4 50 nM for 5 days and only media (no hormones) for 2 days for a total culture period of 28 days. Morphology of 3D units are shown by H&E staining. Immunofluorescent staining of 3D units for vimentin, PR and DAPI revealed presence of cells and expression of these uterine markers in culture.
Figure 17:
Figure 17:
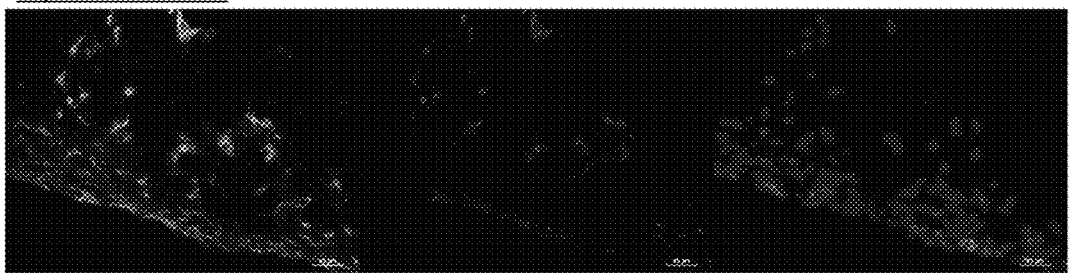
Figure 18:
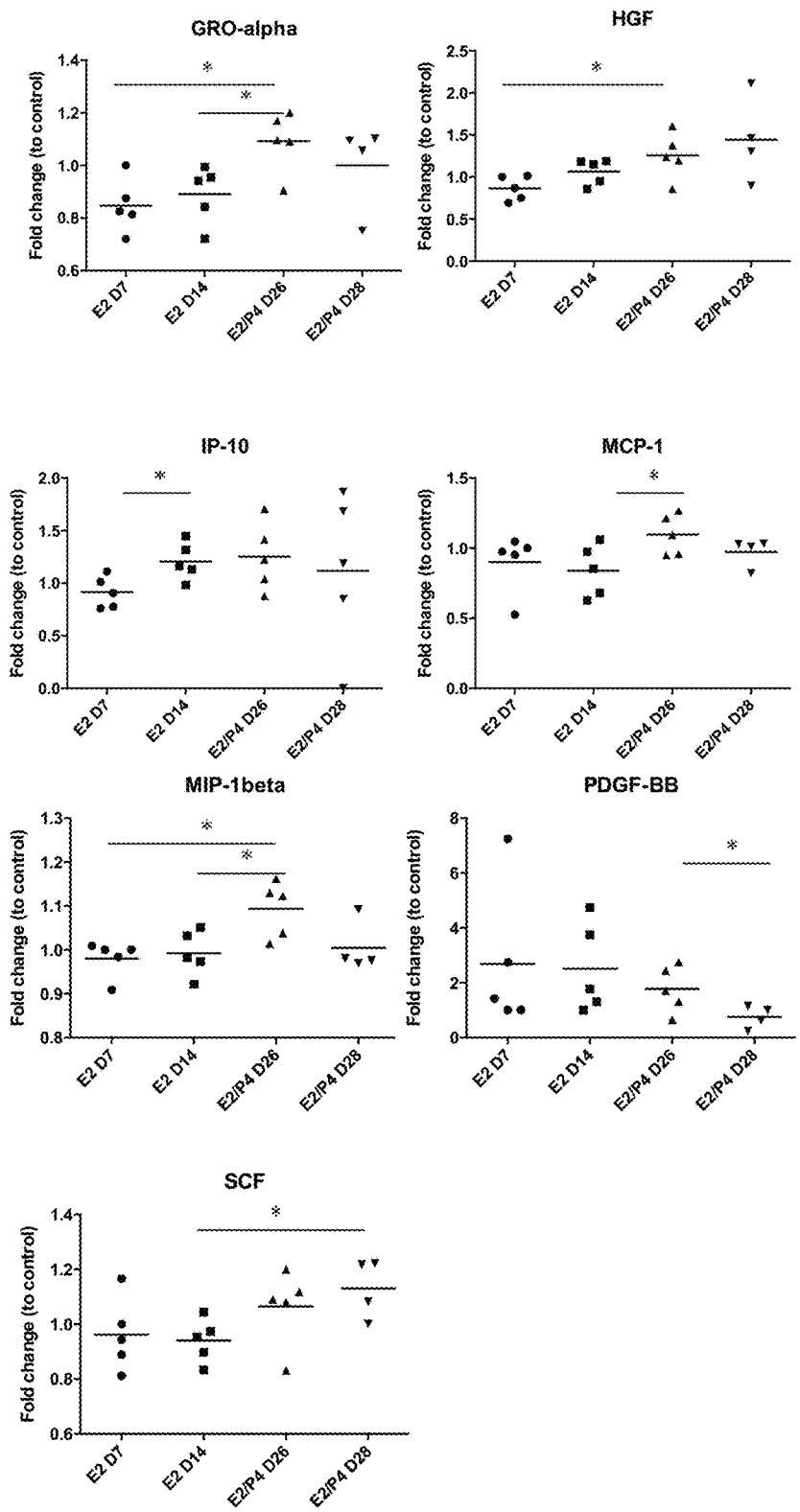
FIG. 18. Graphs measuring hormonal regulation of secreted factors within a static 3D uterine culture system.
Figure 19:
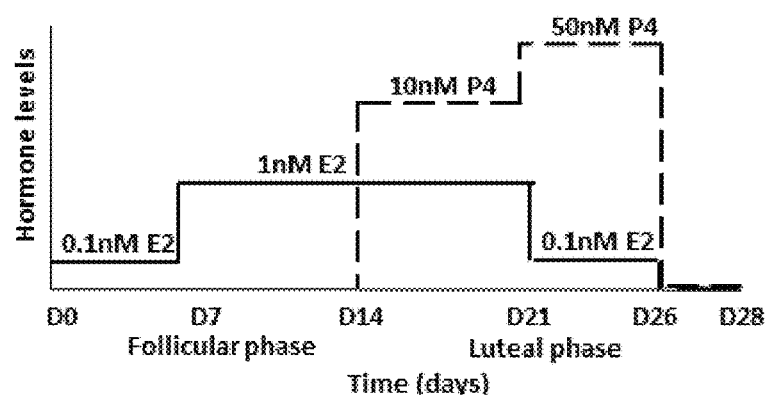
FIG. 19. Graph of hormone levels used during 28 day culture of uterine cells cultured in decellularized matrix. Myometrial cells were re-seeded onto decellurized matrix and cultured for 28 days with the menstrual cycle hormone treatments. H&E staining revealed tissue architecture of the recellularized myometrial matrix. DAPI staining revealed the presence of viable cells within the matrix after 28 days of culture.
Figure 19:
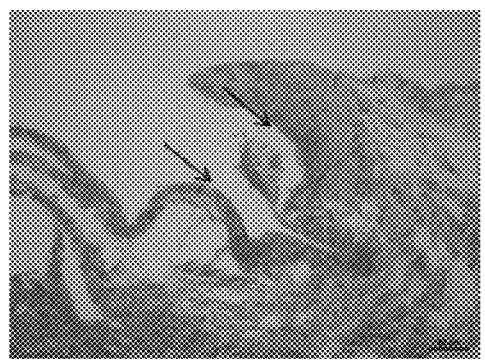
Figure 19:

During a 28-day female reproductive cycle, hormone levels (e.g., estrogen and progesterone) are in flux and the levels of various secreted factors varies (FIG. 17). Experiments were conducted using the static 3D cultures on polystyrene scaffolds described above. Morphologic and hormonal responses of cultured cells were assessed in response to fluctuating levels of estradiol (E2) or progesterone (P4). Morphologically, the 3D endometrial cultures were composed of a mixed population of epithelial and stromal cells. 3D myometrial cultures comprised of myometrial cells (FIG. 17). Cells expressed vimentine and progesterone receptor to in both endometrial and myometrial cells in 3D. A 45-plex Luminex assay identified numerous factors secreted and regulated by hormones (FIG. 18).

The procedure for establishment of 3D endometrial and myometrial cultures on decellularized matrix involved the isolation of epithelial and stromal cells from endometrial tissue and myometrial cells from myometrial tissue followed by expansion of the cells in 2D, and subsequently cultured on a Transwell insert on a decellularized matrix with media collection every 48 hours. The culture was performed for 28 days in the presence of varying concentrations of steroid hormones. H&E staining and DAPI staining of the 3D myometrial units revealed the tissue architecture of the matrix as well as the presence of myometrial cells within the matrix.

Figure 20:
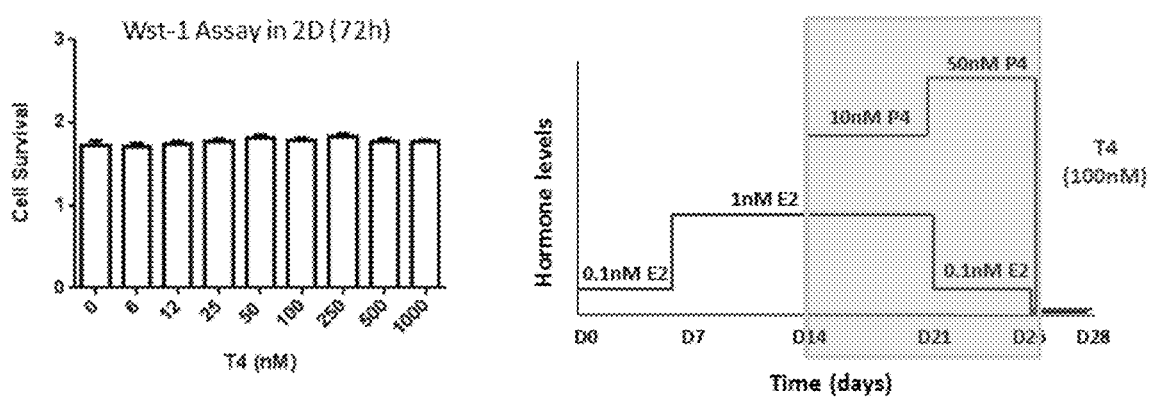
FIG. 20. Left, graph of cell survival assay. Right, graph of hormone levels used during 28 day test of endometrial cell culture response to testosterone levels.

Experiments were conducted during development of embodiments of the present invention to test the response of the endometrium on the decellularized matrix to drug stimulus. Testosterone levels were added during the last 14 days of the 28 day cycle and cell behavior was monitored (FIG. 20 (right)). Cell survival experiments using a Wst-1 assay in endometrial cells cultured in 2D over 72 hours revealed no toxicity of testosterone on the cells (FIG. 20 (left)). Experiments are also conducted to grow myometrium on decellularized matrix (FIG. 54), to test universal media of the culture of multiple uterine cell types, to test response of uterine cell culture system to drug exposure, to monitor the levels of secreted factors over the 28-day cycle, to identify cellular markers and their levels over the 28-days cycle, etc.

Example 5

Ovarian Cultures in 3D Microphysiologic Setting

Experiments were conducted during development of embodiments of the present invention to encapsulate primary follicles in a microfluidic culture system, such that the 3D structure of the follicles is maintained, and the follicles mimic in vivo ovarian responses, and the follicles produce ovarian steroid hormones for downstream cultures in the system.

Figure 22:
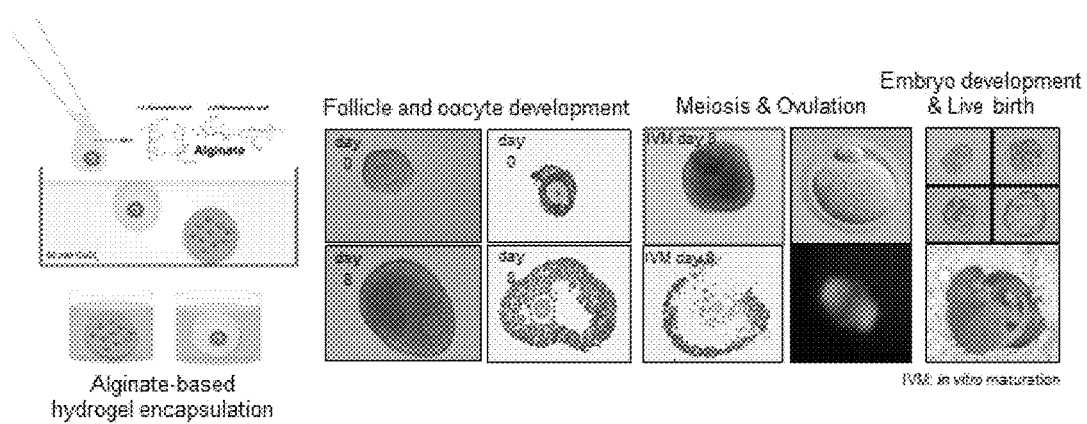
FIG. 22. In vitro support of folliculogenesis, oogenesis, meiosis, ovulation, and embryo development using the 3D culture systems described herein FIG. 23. Schematic of translation of static cultures into dynamic multi-culture system.

Alginate hydrogel was used to encapsulate multiple primary follicles in the microfluidic culture system, which maintains the 3D structure of follicle and recapitulates all key events of the folliculogenesis and oogenesis, including the follicle development from pre-antral to antral stage and oocyte meiotic and developmental competence acquisition (Hornick, et al., 2013). After the treatment with hCG, the mature follicle undergoes ovulation and the oocyte initiates the second meiosis and extrudes the first polar body. These MII eggs are developmental competent and can be fertilized through in vitro fertilization. The fertilized eggs may develop to blastocyst stage in vitro, and give live birth if they are transferred to a recipient host (FIG. 22).

Follicles are typically cultured in 96 or 24 wells cell culture plate, and exogenously added follicle stimulating hormone (FSH) is used to stimulate the follicle growth and human chorionic gonadotropin (hCG) is used to trigger ovulation. Systems described herein connect the different female reproductive tissues together, thereby follicles are cultured in a connected (e.g., microfluidic) system which the ovarian culture is in fluid communication with the other reproductive tissues. In this way, the whole female reproductive tract connected in vitro, and there is a real time delivery of follicle secreted hormones to downstream tissues. To achieve such a system, the traditional static culture is recapitulated in the dynamic multi-culture system (FIG. 23).

In some embodiments, a ovarian culture subsystem comprises one or more culture volumes (e.g., microphysiologic system (MPS) modules), overlaying a fluidic interface (e.g., allowing fluid communication between culture volumes (e.g., with other ovarian culture volumes and/or with other tissue subsystems), which in turn overlays an actuator interface. Such a design, or other suitable designed described herein allow, for example: materials (e.g., media, cells, reagents, etc.) to be sterilely introduced into the culture volumes (e.g., directly, via the fluidic interface, etc.), unidirectional and/or recirculated flow, flow oriented toward the follicular subsystem, sufficient mixing of media, adjustable flow rate (e.g., in and/or out), collection of passed media, support of culture in polymer matrix (e.g., alginate beads), handling/loading of materials, etc.

Figure 24:
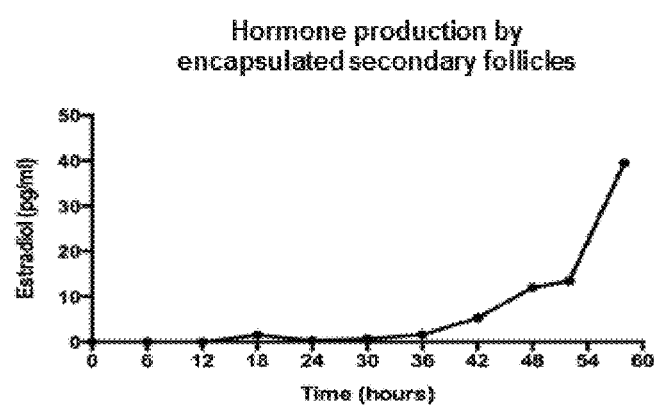
FIG. 24. Graph depicting hormone production by encapsulated secondary follicles.
Figure 25:
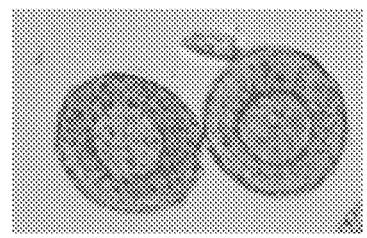
FIG. 25. Image demonstrating morphology of follicles recovered after culture in ovarian microfluidic subsystem.
Figure 26:
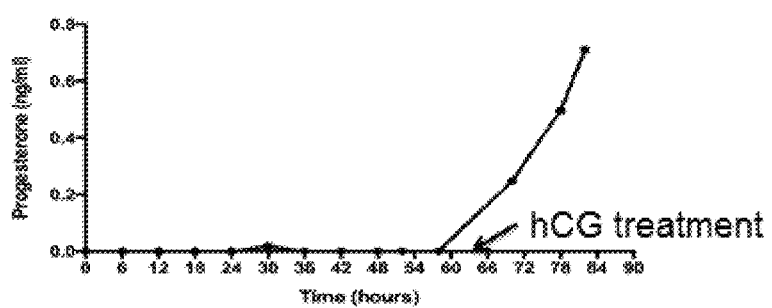
FIG. 26. Graph demonstrating increased progesterone production from follicles in ovarian microfluidic subsystem following hCG treatment.

Experiments were conducted during development of embodiments of the present invention demonstrating that the microfluidic ovarian subsystem supports the follicle growth in vitro. Secondary follicles were cultured for up to 60-90 hours, with significantly increased estradiol production (FIG. 24) and the follicles retrieved from microfluidic system showed good morphology (FIG. 25). After hCG treatment, significantly increased progesterone secretion was observed (FIG. 26), indicating the follicle undergoes the luteal phase. These results demonstrate that the microfluidic culture system supports the in vitro follicle growth in the same manner as static culture.

Figure 27:
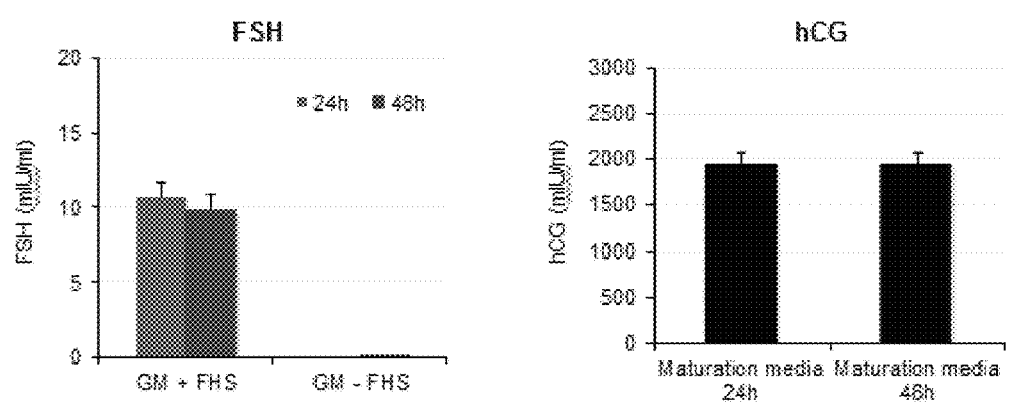
FIG. 27. Graphs demonstrating the stability of FSH (left) and hCG in the ovarian microfluidic subsystem.

Experiments were conducted during development of embodiments of the present invention to demonstrate the stability of FSH and hCG in the microfluidic system, which are very critical for the follicle development. A 14 days pretest was done with growth medium but without follicles in the microfluidic system. Results indicate that after 48 hours incubation, both FSH and hCG are stable in the microfluidic system and there is no degradation (FIG. 27). Therefore, the materials used for the microfluidic ovarian culture module are good for the follicle culture and added hormones are stable in the microfluidic system.

Figure 28:
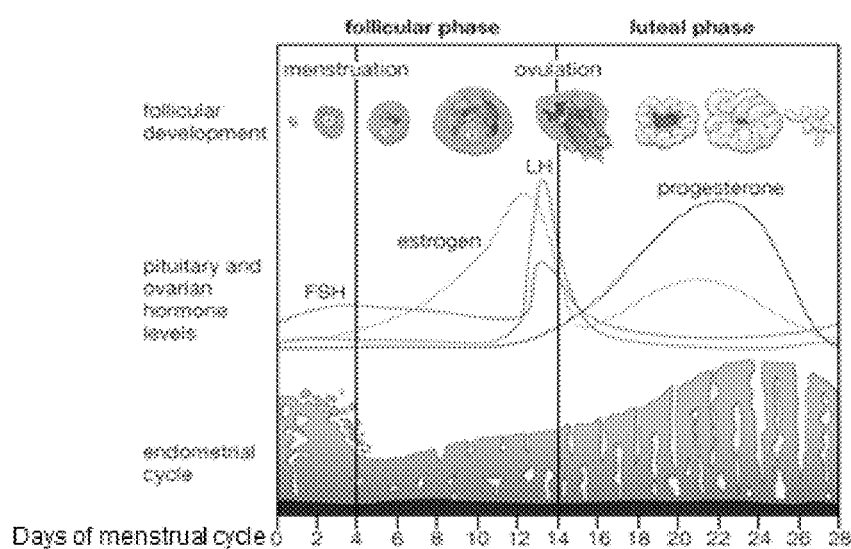
FIG. 28. Graphical depiction of the human female 28-day estrous cycle.

During the human 28-day estrous cycle, the pituitary hormones regulate the follicle development, and the ovarian hormones regulate the downstream tissue, such as uterine endometrium. The follicle development includes two phases, the follicular phase and the luteal phase (FIG. 28). During the follicular phase, follicles develop from pre-antral stage to antral stage. After the LH surge, the follicle ovulates MII egg and develop into the corpus luteam which is called luteal phase. The follicle secretes estrogen during follicular phase and secretes progesterone during luteal phase to maintain the physiological functions of ovary and other female reproductive tissues. The microfluidic system described herein utilizes a 28 day in vitro follicle culture to mimic the 28 days human estrous cycle in vitro in the microfluidic system.

Figure 29:
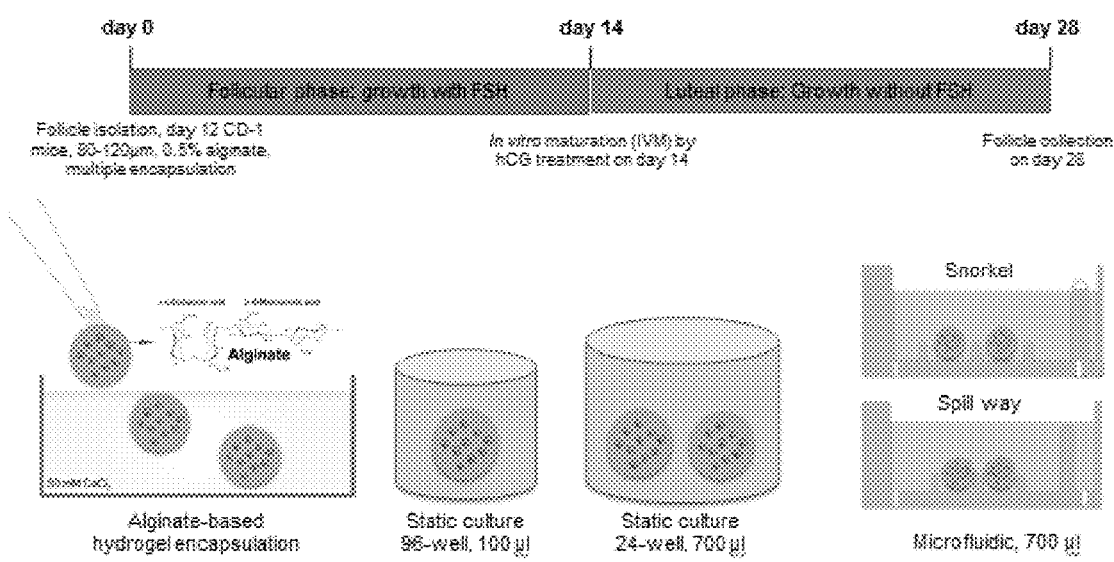
FIG. 29. Experimental design for testing the ovarian culture subsystem.
Figure 30:
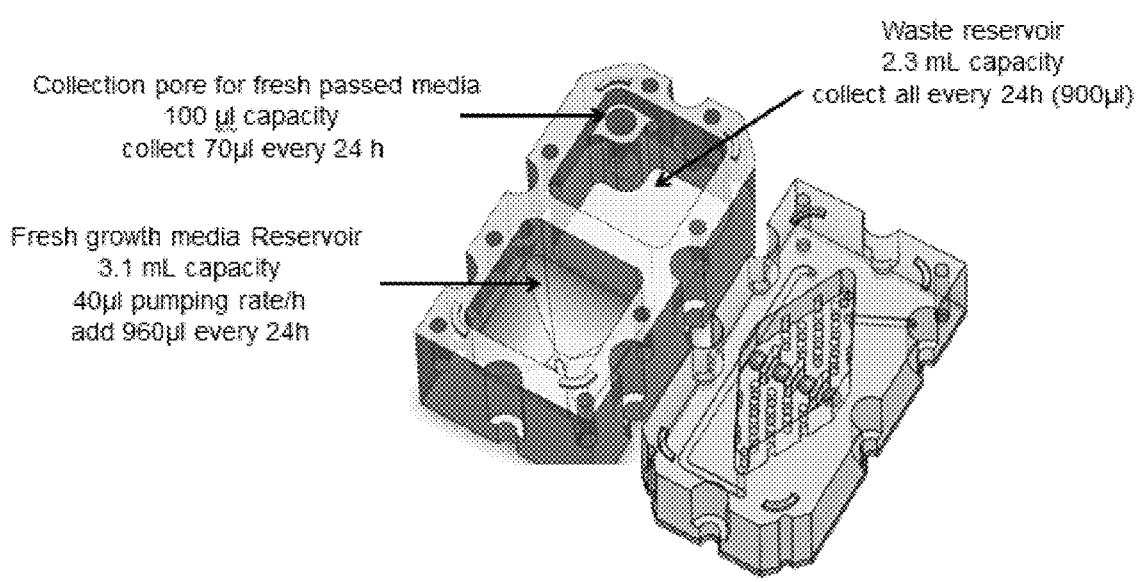
FIG. 30. Drawing of exemplary ovarian culture subsystem.
Figure 31:
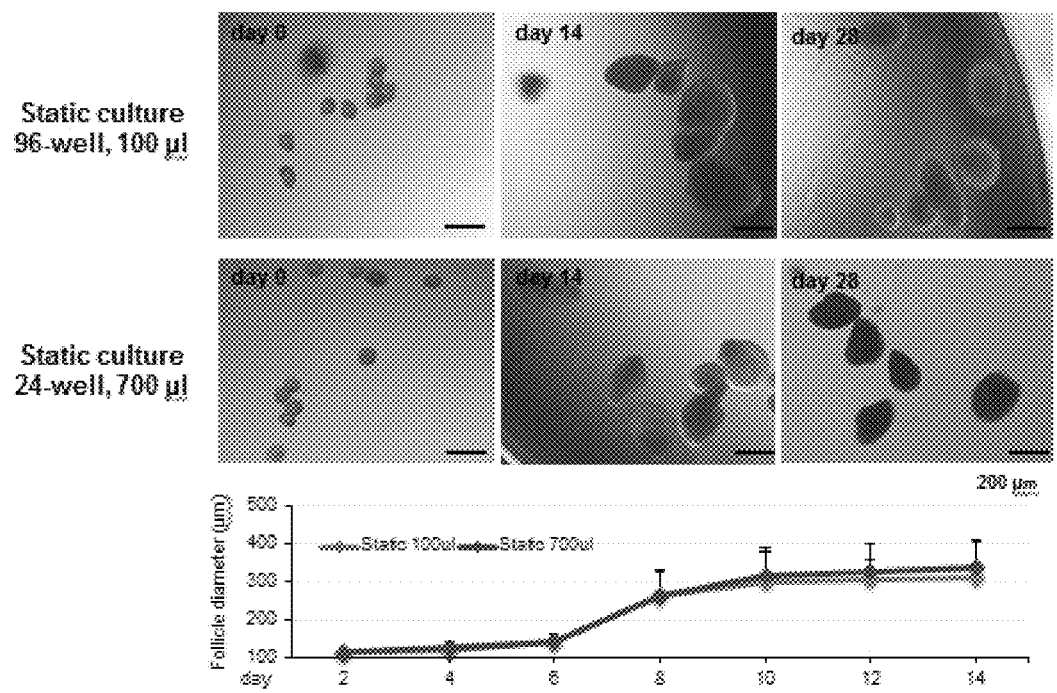
FIG. 31. Images (top) and graph (bottom) depicting follicular growth in static culture.
Figure 32:
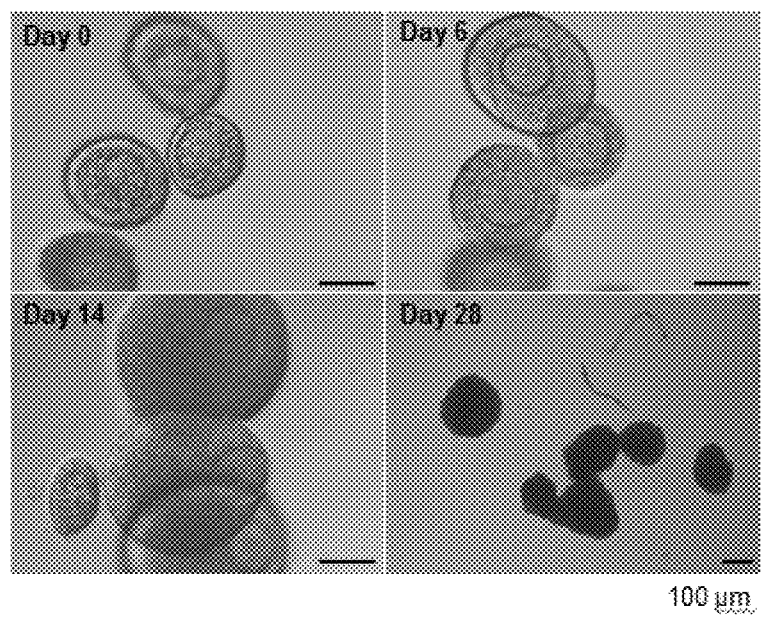
FIG. 32. Images depicting follicular growth in both the follicular phase and luteal phase supported by an exemplary ovarian culture subsystem.
Figure 33:
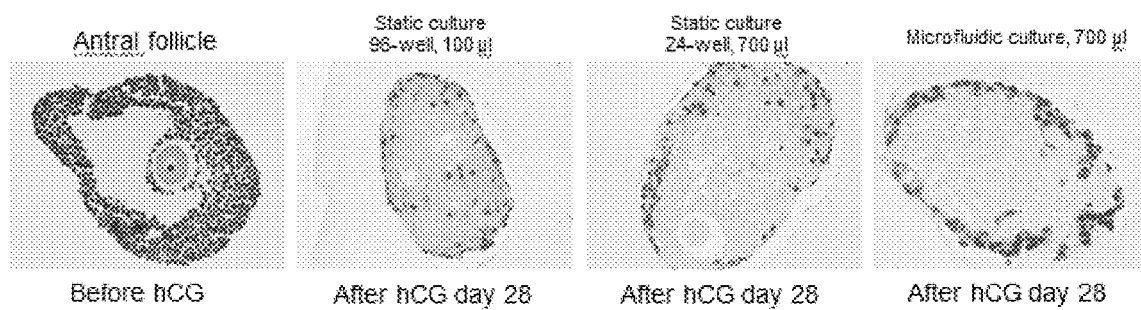
FIG. 33. Images demonstrating follicle histology following 28 days of static culture and 28 day culture in an exemplary ovarian culture subsystem.

Experiments were conducted during development of embodiments of the present invention in which primary follicles were isolated from 12 days old mice and encapsulated in 5% alginate, multiple follicle encapsulation is used because the primary follicles need each other to support the follicle growth. Follicles were cultured for 14 days to mimic the follicular phase with the growth medium with FSH. On day 14, follicles were treated with hCG to trigger the ovulation and initiate the luteal phase with the growth medium without FSH. On day 28, all follicle are collected for histology and gene expression study. Follicle growth was performed in three groups: (1) 10 follicles in one alginate bead, cultured in a well of a 96-well plate in 100 µl growth medium, (2) 20 follicles in two alginate beads cultured a well of a 24-wells plate with 700 µl growth medium to mimic the condition for microfluidic culture system, (3) microfluidic culture system, 20 primary follicles in 2 alginate beads in each culture module (FIG. 29). For the static culture, growth medium is collected and replaced every 48 hours. For the microfluidic culture, the system pumps 40 µl per hour to the follicle culture modele, thereby adding 960 µl of fresh media each day. In the collection pore for fresh passed media, the capacity is only 100 µl, it represents the recent media pumped from the follicle culture well (FIG. 31). 70 µl is collected each day. In the waste reservoir, the media represents the media passed during the past 24 hours (FIG. 30). Follicle growth in the static culture in both 100 and 700 µl culture groups indicates that the multiple follicle encapsulation supports the follicle growth (FIG. 31). The follicle diameter is around 310 in 100 µl static culture, and 330 in 700 µl static culture, and there is no significant difference for the follicle growth between these two static culture strategies. The survival rates are 83.33% and 81.25%, and there is no significant difference. Microfluidic system also supported follicle growth in both the follicular phase (day 1-14) and luteal phase (day 14-28) (FIG. 32). Since the daily follicle monitoring is not available in the microfluidic culture system used in these experiments, follicles cultured in different modules were collected and imagined on different days (day 0, day 6, day 14 and day 28) (FIG. 32). Results indicate that microfluidic system also supported the follicle growth in both the follicular phase (day 1-14) and luteal phase (day 14-28) in microfluidic culture system (FIG. 32). The granulosa cells luteinized into granulosa lutein cells after the LH surge in vivo. If there is no fertilization, the corpus *luteum* (CL) degenerates into the corpus *albicans*, which is a fibrous scar tissue. The histology data indicate that all follicles retrieved from both static and microfluidic systems on day 28 show fibrous scar like tissue, which consistent with the morphological changes as in (FIG. 33).

Figure 34:
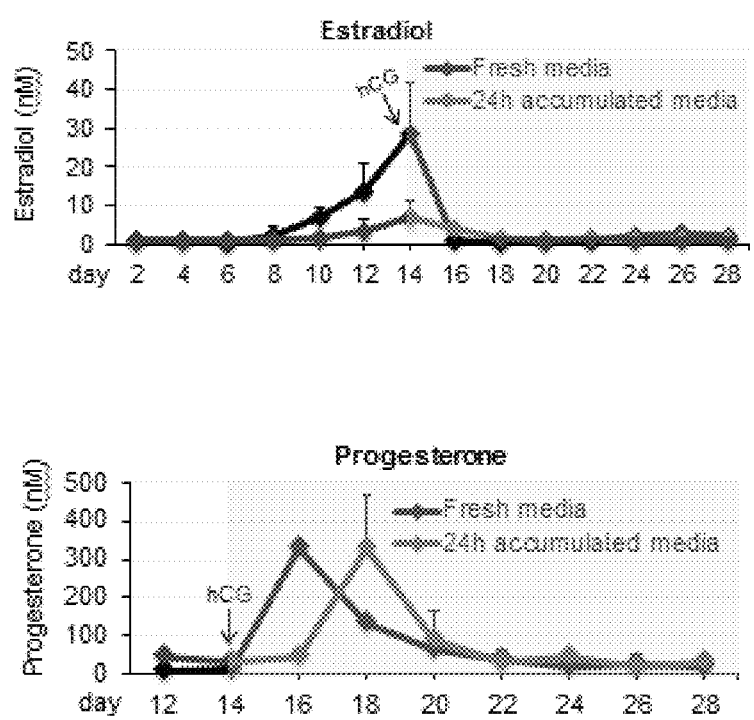
FIG. 34. Graphs depicting hormone secretion over a 28-day period from follicles in an exemplary ovarian culture subsystem.

Since the ovarian steroid hormones are critical for the downstream tissue function in female reproductive system, ovarian hormones secretion in the microfluidic system was tested to determine whether this system could mimic the 28 day female menstrual cycle in vitro. The hormone secretion data demonstrate the follicles cultured in microfluidic phenocopy the 28 day human menstrual cycle. During the first 14 days of follicular phase, follicles keep secreting estradiol which peaks on day 14 (FIG. 34 (top)). After the hCG treatment on day 14, follicles initiate the luteal phase and secret more progesterone which peaks 2 days after the hCG treatment (FIG. 34 (bottom)).

Figure 35:
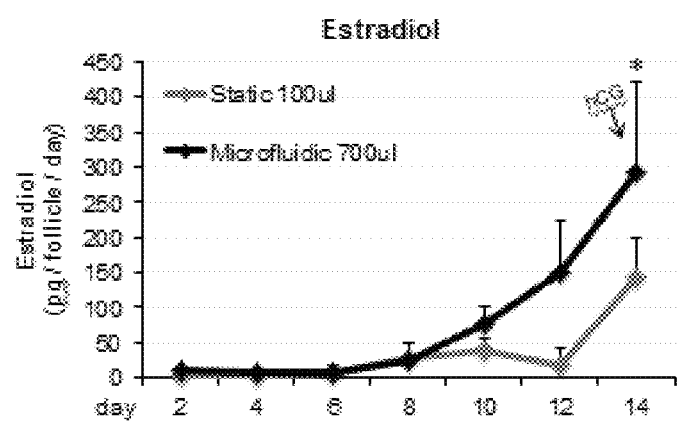
FIG. 35. Graph comparing estradiol production over a 14-day span from cells grown in 100 µl static culture and 700 µl microfluidic culture.
Figure 36:
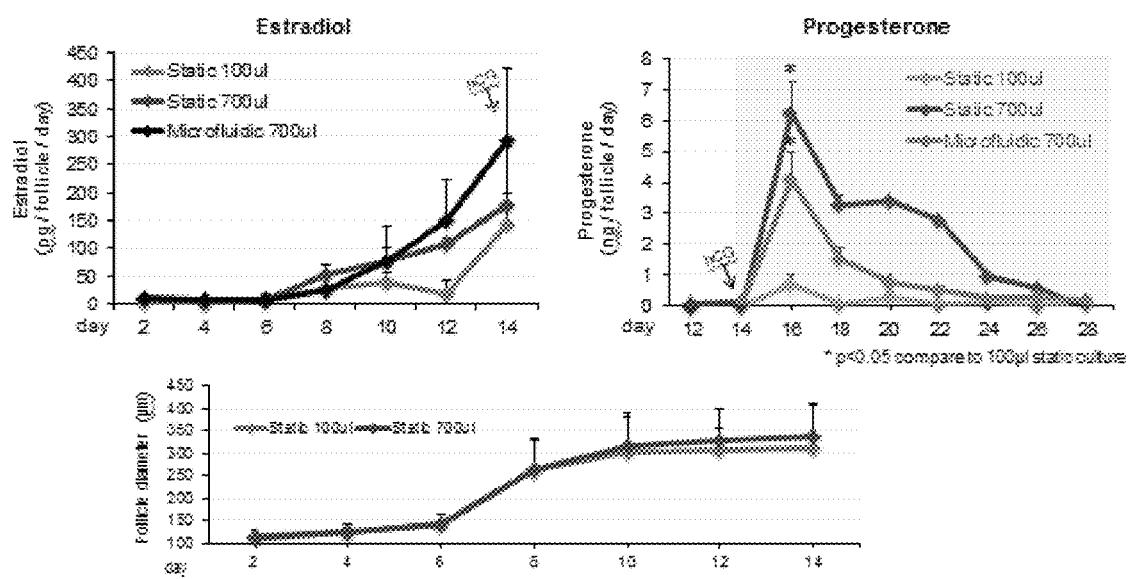
FIG. 36. Graphs comparing estradiol production (top left), progesterone production (top right), and follicle diameter over a 14-day span from cells grown in 100 µl static culture, 700 µl static culture, and 700 µl microfluidic culture.

Follicles cultured in microfluidic system secreted more estradiol and progesterone compared to 100 µl static culture (FIG. 35). In static culture, follicles in 700 µl culture system, which is used to mimic the microfluidic culture module, grow significantly faster than that in 100 µl culture system. Thus indicating that promoted follicle growth in the microfluidic culture system contributes to the increased estradiol and progesterone secretion (FIG. 36).

Figure 37:
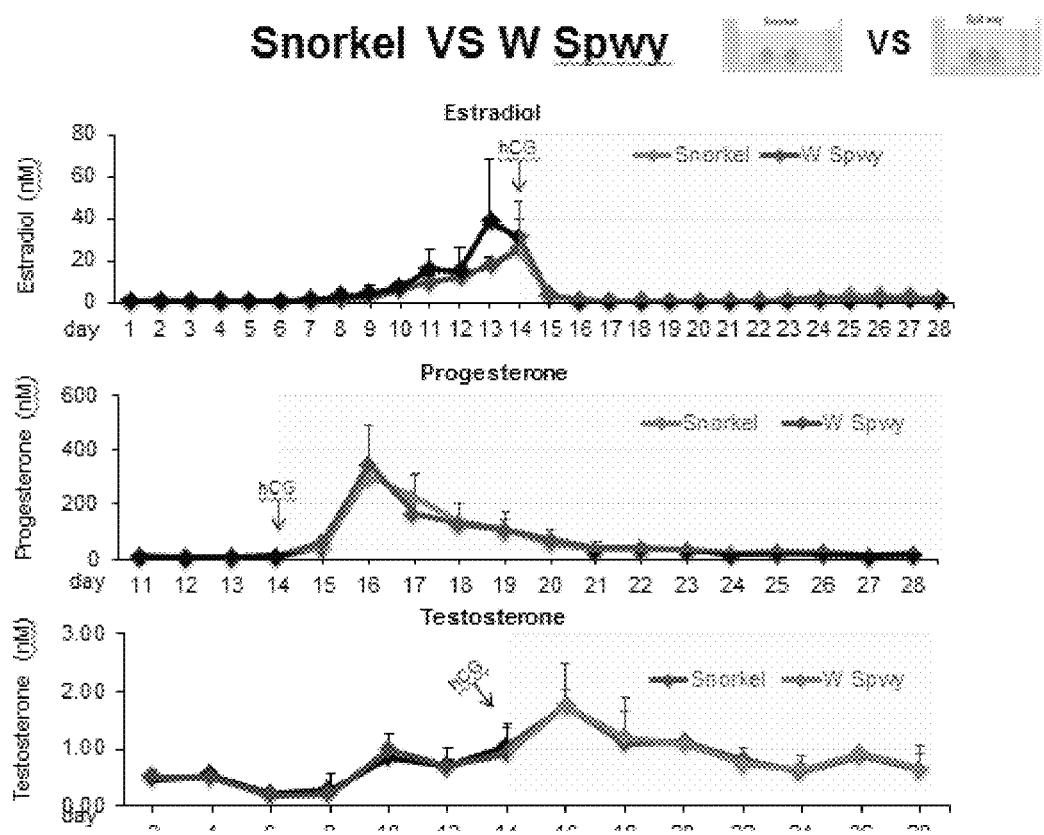
FIG. 37. Graphs comparing hormone expression levels for snorkel and W spill way media outlet designs.

Experiments were conducted during development of embodiments of the present invention to compare culture media outlet designs (e.g., snorkel vs. W Spwy). Follicle hormone secretion levels were compared between these two different designs (FIG. 37). Results indicate that there is no significant difference for the hormone secretion levels between Snorkel and W Spill Way outlet designs for all three hormones analyzed. These data indicate that there is no efficiency difference for these two designs.

Figure 38:
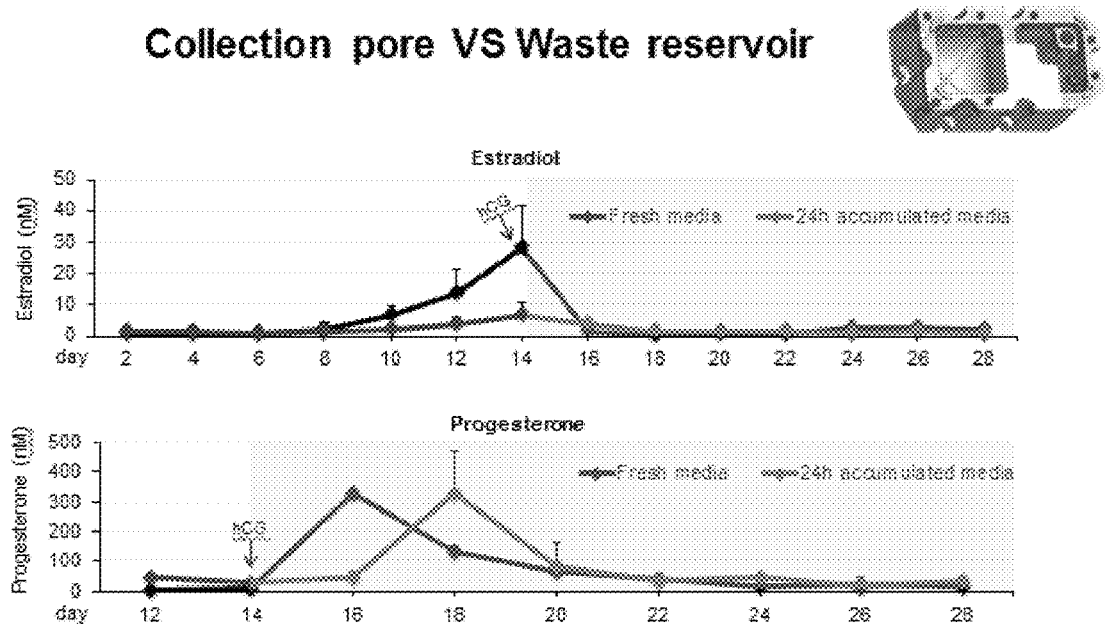
FIG. 38. Graphs comparing hormone expression levels for culture subsystems comprising a waste reservoir and collection pore.

Experiments were conducted during development of embodiments of the present invention to compare the use of a waste reservoir and collection pore (FIG. 38). Media from the collection pore has higher estradiol expression level from day 10, suggesting more estradiol secretion upon the follicle growth, especially upon the follicle antrum formation. Although the absolute progesterone expression levels are similar, the peak for the reservoir culture shifted 2 days later compared to the media from collection pore, suggesting the progesterone secretion peaks around 48-72 h after the hCG treatment and then gradually decreased.

Figure 39:
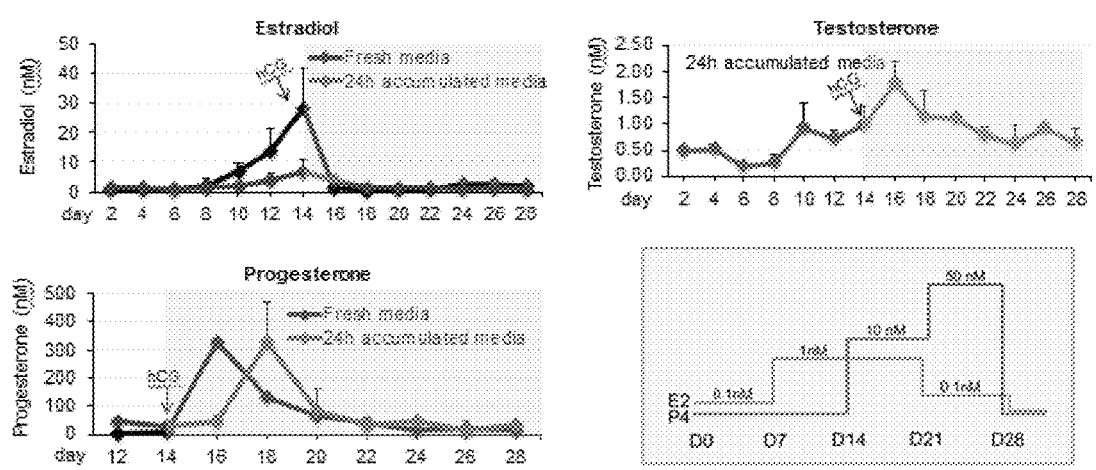
FIG. 39. Graphs depicting hormone levels in fresh and 24-hopur accumulated media over the course of a 28-day cycle in an exemplary ovarian culture subsystem.

Experiments were conducted during development of embodiments of the present invention to compare hormone levels in an exemplary ovarian microfluidic subsystem to physiologic levels (FIG. 39). Results indicate that estradiol and progesterone levels in microfluidic system were higher than human physiological levels (7 folds in 24 h accumulated media), and that testosterone secretion levels were similar to the human physiological level (0.5-2 nM).

Figure 40:
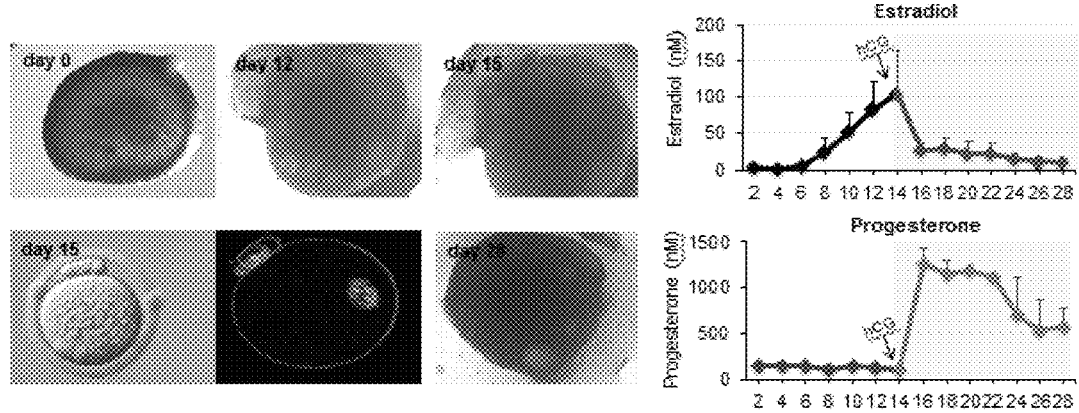
FIG. 40. Images (left) and graphs (right) show morphology and hormone secretion levels of cultured whole ovaries.

Experiments conducted during development of embodiments of the present invention demonstrated that 28-day whole ovary culture supports follicle growth in vitro and produce MII eggs after the hCG treatment on day 14. Moreover, the in vitro cultured ovary shows similar hormone expression patterns as the follicle culture in both static and microfluidic system (FIG. 40).

Example 6

Fallopian Cultures in 3D Microphysiologic Setting

Experiments were conducted during development of embodiments of the present invention to culture human fallopian tissues in a microfluidic culture system, such that the cultured tissue responds to the menstrual cycle (See e.g., Eddie S L, Quartuccio S M, Zhu J, Shepherd J A, Kothari R, Kim J J, Woodruff T K, Burdette J E. Three-dimensional modeling of the human fallopian tube fimbriae. Gynecol Oncol. 2014 Dec. 16; herein incorporated by reference in its entirety).

Alginate matrix was utilized to support human fallopian fimbriae ex vivo. Fimbriae were cultured with factors hypothesized to contribute to carcinogenesis, namely; $H_2O_2$ (1 mM) a mimetic of oxidative stress, insulin (5 µg/ml) to stimulate glycolysis, and estradiol ($E_2$, 10 nM) which peaks before ovulation. Cultures were evaluated for changes in proliferation and p53 expression, criteria utilized to identify potential precursor lesions. Further, secretory factors were assessed after treatment with $E_2$ to identify if steroid signaling induces a pro-tumorigenic microenvironment.

3D fimbriae cultures maintained normal tissue architecture up to 7 days, retaining both epithelial subtypes. Treatment of cultures with H2O2 or insulin significantly induced proliferation. However, p53 stabilization was unaffected by any particular treatment, although was induced by ex vivo culturing. Moreover, E2-alone treatment significantly induced its canonical target PR and expression of IL8, a factor linked to poor outcome.
Tissue Collection Fallopian fimbriae were collected with consent prior to surgery at the University of Illinois at Chicago (UIC IRB #2012-0539). Patients utilized in this study were undergoing salpingectomy for a variety of gynecological purposes. Resulting tissues were deemed morphologically normal and considered benign as determined by gross examination by the University of Illinois at Chicago Pathology Department. A total of 12 samples from patients ranging from 28-62 years of age (average age of 43).
3D Culture Optimization and Treatment Tissues were micro-dissected in alpha-MEM (Gibco, Carlsbad, Calif.) with 1% penicillin-streptomycin (Invitrogen, Carlsbad, Calif.). Individual fimbriae were separated into ~50 $mm^3$ pieces. A portion of the tissue was fixed in 2% paraformaldehyde for use as an uncultured control. For optimization studies, fimbriae were cultured without matrix, encapsulated in 0.5% alginate, or encapsulated in 0.5% alginate with 1 mg/ml collagen and 0.1% fibronectin, as previously described for murine cultures (King et al. J Vis Exp. 2011; herein incorporated by reference in its entirety). For subsequent treatments, 0.5% alginate encapsulated fimbriae were randomly assigned to treatment groups, with at least five fimbriae per condition, per patient, in a 24-well plate containing alpha-MEM and 1% penicillin-streptomycin. Tissues were treated with 1 µl/ml ethanol (vehicle), 10 nM $E_2$ (Sigma-Aldrich, St. Louis, USA), 1 mM $H_2O_2$ (Fisher Scientific, Pittsburgh, Pa.), or 5 µg/ml insulin (via ITS (insulin; transferrin 5 µg/ml; selenite 5 ng/ml) Roche, Indianapolis, Ind.), and cultured for 2 or 7 days. Prior to fixation, fimbriae were labeled with 10 µM bromodeoxyurine (BrdU, Sigma-Aldrich) for 24 hours to denote proliferating cells. Fimbriae cultures were fixed (2% paraformaldehyde) followed by dehydration in ethanol and xylene, and embedment in paraffin.
Tissue Preparation and Immunohistochemistry Sections (5 µm) were cut and stained via hematoxylin and eosin for morphological analysis or immunohistochemistry was performed to localize proteins of interest as previously described (King et al. Endocr Relat Cancer. 2011. 18:627-42; herein incorporated by reference in its entirety). Slides were rehydrated through an ethanol gradient, prior to 0.1M sodium citrate retrieval and peroxidase block. Tissues probed for BrdU were exposed to 4M HCl and 0.1M $NaB_4O_7$ (Fisher Scientific) to denature DNA. All immunohistochemical reagents were obtained from Vector Laboratories, Inc (Burlingame, Calif.) unless otherwise stated. Tissues were blocked in 3% bovine serum albumin (Gemini, West Sacramento, Calif.)-TBS/10% serum and incubated with a primary antibody 1:50 acetylated tubulin (Cell Signaling, Cambridge, Mass.); 1:200 BrdU (AbCam, Cambridge, Mass.); 1:100 cytokeratin 8 (CK8, Developmental Studies Hybridoma Bank, Iowa City, Iowa); 1:50 p53 (Santa Cruz, Santa Cruz, Calif.); 1:100 PAX8 (Proteintech, Chicago, Ill.); 1:100 pH2AX (Cell Signaling); or 1:75 PR (Santa Cruz)) overnight at 4°. Tissues were washed in TBS-0.1% Tween and incubated with a secondary antibody (1:200), before being probed with ABC peroxidase standard, followed by detection with 3,3'-diaminobenzidine (DAB) and counterstained with hematoxylin.
Image Capture and Analysis Immunohistochemistry images were taken via a Nikon E600 microscope, DXM1200 digital camera and NIS Elements software (Nikon Instruments, Melville, N.Y.). For proliferation analysis, concurrent sections were stained for CK8 and BrdU. BrdU sections were imaged and epithelial cells (CK8 positive) were quantified for proliferation via ImageJ software (NIH, Bethesda, Md.). At least three fimbriae with 200 or more FTE were quantified for each treatment. Analysis of p53 staining was similar, with at least three fimbriae per treatment, per patient analyzed. Samples with p53 expression were quantified utilizing adjacent sections stained for the secretory cell marker PAX8 in a qualitative manner as described.
ELISA IL8, VEGF-A, and FGF2 were detected in fallopian culture medium by enzyme-linked immunosorbent assay for human IL8 (EMD Millipore, Billerica, Mass., USA), VEGF-A (RayBiotech, GA, USA), or FGF2 (Abcam) respectively using the manufacturers' protocols. The sensitivity for IL8, VEGF-A, and FGF2 are 4.4 pg/ml, 10 pg/ml, and 2 pg/ml, respectively. Results were normalized to total protein content as determined by western blotting and Ponceau staining to account for difference in tissue size between treatment groups. Conditioned medium (20 μl) was run on a 10% SDS-PAGE gel and transferred to nitrocellulose membrane (Fisher Scientific). Ponceau (Sigma-Aldrich) staining and subsequent densitometry via ImageJ software was performed.

3D Fimbriae Cultures Retain Tissue Architecture and Epithelial Subtypes

Optimization was performed to identify culture conditions that best supported fallopian architecture ex vivo. Previous studies identified alginate as an ideal matrix for the maintenance of baboon and murine ovaries and oviducts (King et al. J Vis Exp. 2011; Xu et al. Biol Reprod. 2011. 84:689-97; herein incorporated by reference in their entireties), therefore 0.5% alginate was utilized to encapsulate human fallopian fimbriae alongside fimbriae with no culture matrix, and 0.5% alginate supplemented with extracellular matrix (1 mg/ml collagen and 0.1% fibronectin). Culture of human fimbriae revealed the alginate matrix maintained tissue architecture and cell morphology up to 7 days. Samples without matrix were also intact after 7 days, but had flattening of the FTE in some areas. No additional benefit was seen with supplementary ECM. Therefore, alginate hydrogel (0.5%) was utilized for subsequent experiments.

Figure 41:
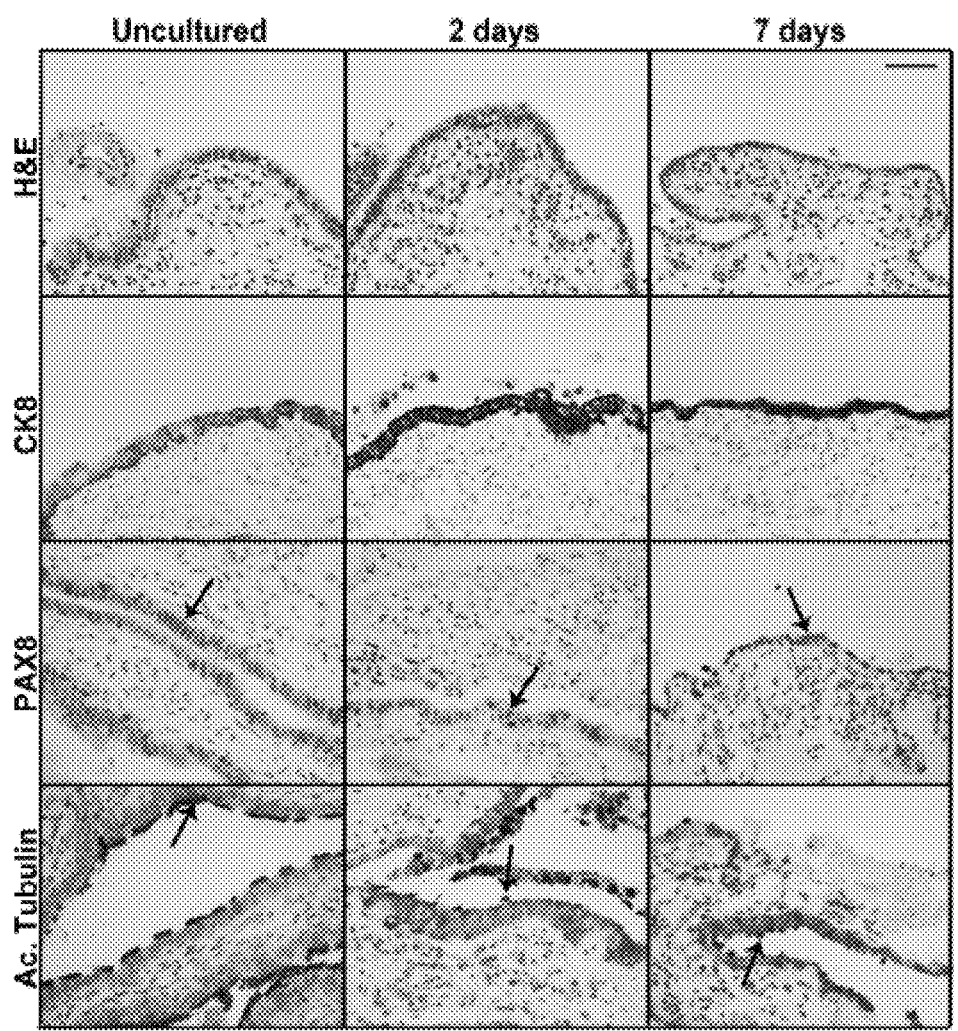
FIG. 41. 3D human fimbriae culture system supports secretory and ciliated epithelium. Human fimbriae cultures encapsulated in alginate hydrogels retained normal tissue architecture for up to 7 days in culture, as demonstrated by comparative H&E staining. FTE was maintained as identified by cytokeratin 8 (CK8) staining. Further, both epithelial subtypes; secretory (PAX8) and ciliated (Ac. Tubulin) Scalebar equals 50 µm.

Characterization after 2 and 7 days in culture indicated that alginate maintained FTE viability and contact with the fallopian stroma (FIG. 41). Both epithelial and stromal compartments appeared morphologically similar to uncultured tissues, as indicated by H&E staining and the epithelial marker CK8. Further, unlike extended culture of fallopian epithelium in 2D where ciliated epithelia are lost, 3D fimbriae cultures retain both FTE subtypes; ciliated (acetylated tubulin) and secretory (PAX8), allowing for investigation of the role of both epithelial subtypes in fallopian function and pathophysiology.

Insulin and $H_2O_2$ Induce Epithelial Proliferation in Fimbriae Cultures

Figure 42:
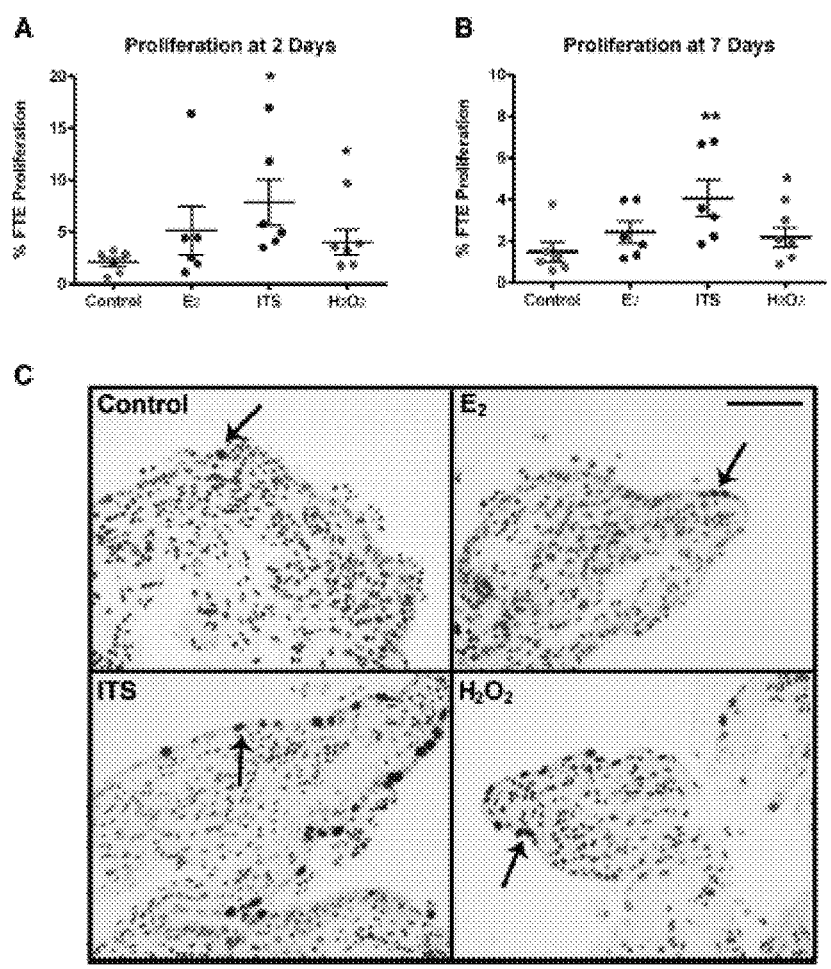
FIG. 42. 3D Fimbriae proliferation in response to estrogen, insulin, and hydrogen peroxide. Proliferation was quantified in the FTE of human fimbriae treated with 10 nM estradiol (E2), 1×ITS, 1 mM H2O2 or vehicle (Control) for A) 2 and B) 7 days. ITS and H2O2 demonstrated enhanced proliferation after 2 and 7 days in culture. E2 did not alter FTE growth. C) Proliferation was determined by 24 hour BrdU labeling (arrows) n=6. Error bars equal mean±SEM. Scalebar equals 50 µm.

Proliferation is an important aspect of normal physiology and uncontrolled proliferation is a hallmark of tumorigenesis. To clarify the regulation of human FTE proliferation, ovulatory factors hypothesized to be involved in serous carcinogenesis were investigated (n=6). Insulin treatment, contained within the common culture supplement ITS, induced FTE proliferation after both 2 and 7 days in culture (7.8±2.2% and 4.1±0.9% respectively) compared to vehicle control treated 3D cultures (2.1±0.4% and 1.5±0.5%, FIGS. 42A and 42B). Proliferation in control cultures was similar to basal proliferation levels in normal in vivo fimbriae (~1-3%) (George et al. Clin Cancer Res. 2012. 18:6199-207; herein incorporated by reference in its entirety). The oxidative stress mimetic, $H_2O_2$, induced proliferation at 2 and 7 days (4.0±1.1% and 2.2±0.5%, respectively). However, treatment with the steroid hormone $E_2$ did not significantly affect epithelial proliferation (5.2±2.3% and 2.4±0.5%, day 2 and day 7 respectively). FTE proliferation was determined as a percentage of total FTE cells 24 hrs post-BrdU labeling (FIG. 42C). BrdU labeling results were supported by Ki67 immunostaining.

$E_2$ Regulates Fallopian Tissue and Induces Secretion of the Pro-Tumorigenic Factor IL8

Figure 43:
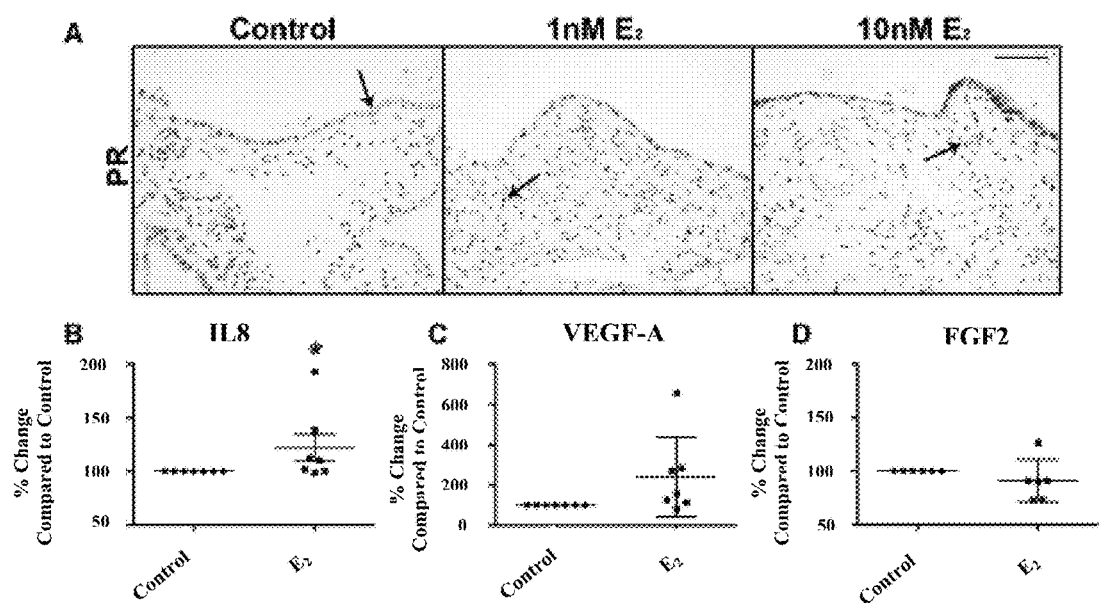
FIG. 43. E2 induces PR expression and IL8 secretion from 3D cultured human fimbriae. A) Progesterone receptor (PR) expression is limited to a portion of the FTE in control (vehicle treated) samples. Epithelial and stromal expression is induced by treatment with 1 or 10 nM E2 for 7 days (arrows). B) Treatment of fallopian cultures with 10 nM E2 demonstrated induction of the pro-tumorigenic cytokine IL8 compared to control (vehicle treated). No change was seen in other pro-inflammatory cytokines; C) VEGF-A and D) FGF2. Scalebar equals 50 µm.
Figure 44:
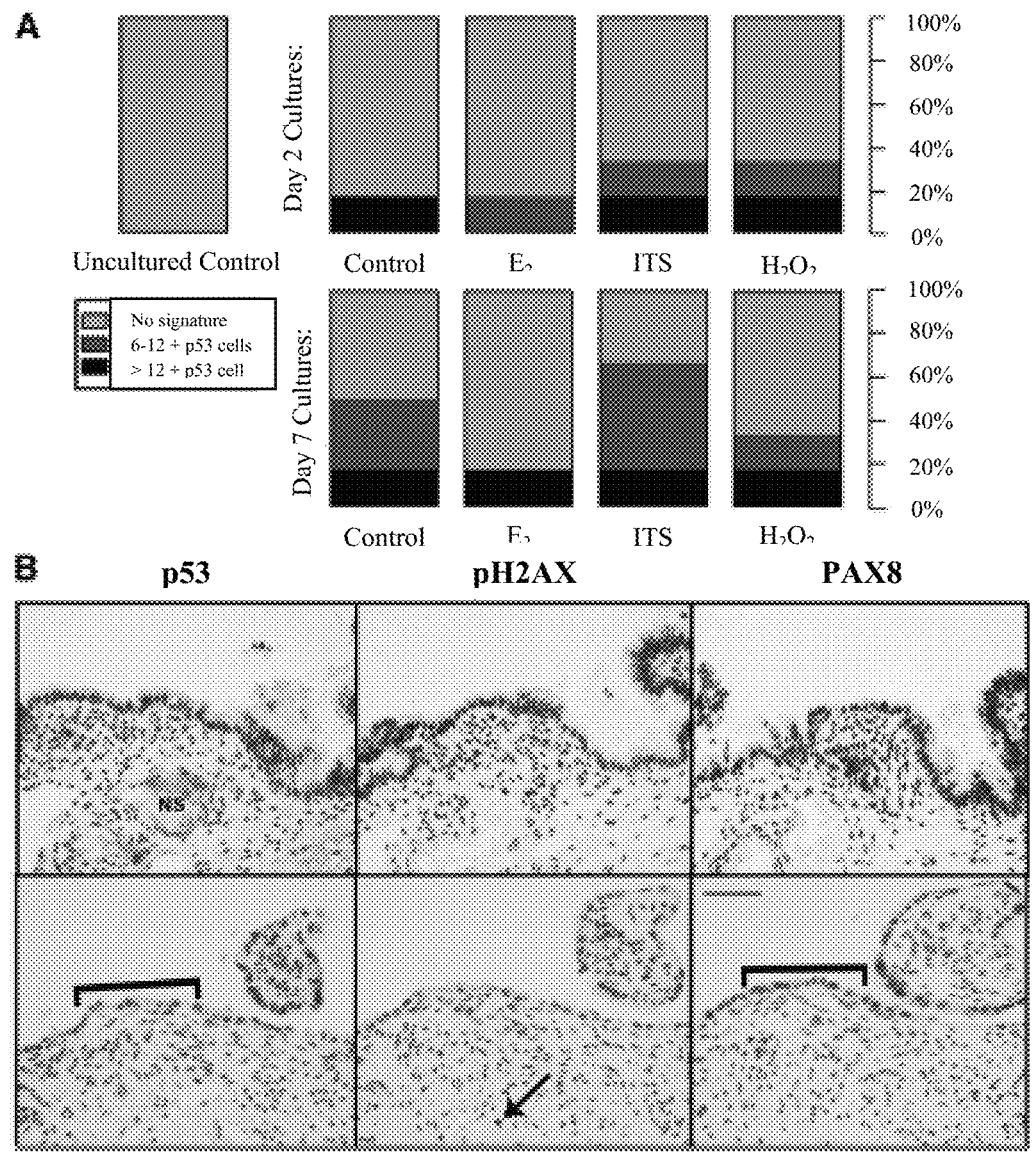
FIG. 44. p53 expression is induced in 3D human fimbriae cultures. A) p53 expression was evaluated in FTE of 3D human fimbriae samples cultured for 2 and 7 days with vehicle (control), 10 nM E2, 1×ITS, or 1 mM H2O2. p53 expression was not induced by an specific treatment. However, p53 expression did appear to be induced by culturing alone. B) p53 signatures were not identified in uncultured samples, but were noted in ex vivo cultured fimbriae (arrow) primarily in secretory epithelium (PAX8), but not always coincidental with DNA damage (pH2AX) although damage was seen in stromal cells (arrow). Scalebar equals 50 µm. NS=non-specific staining.

Although $E_2$ treatment did not induce proliferation, it was functional in fimbriae samples, with the induction of its conical target, progesterone receptor (PR) at both 1 nM and 10 nM concentrations compared to vehicle control treated tissues (FIG. 43A). PR expression was weak and limited to epithelial cells in control tissues and heightened in both the FTE and underlying fallopian stroma post-$E_2$ treatment, further demonstrating the necessity of studying these cell types in association, as steroidogenic responses are induced in both tissue compartments. To clarify the link between $E_2$ signaling and ovarian cancer risk, fallopian tissues were treated with 10 nM $E_2$ for 7 days and the conditioned medium compared to culture medium from samples treated with vehicle. These experiments identified a significant increase in the pro-inflammatory, angiogenic cytokine interleukin 8 (IL8, FIG. 43B), in $E_2$ treated samples (22%±13% increase) compared to vehicle control (n=7). The modest increase in IL8 induced by $E_2$ was specific, as other pro-tumorigenic factors, including vascular endothelial growth factor (VEGF-A, 140%±75% increase compared to vehicle control, n=7, FIG. 43C), or fibroblast growth factor 2 (FGF2, 9%±8% decrease compared to vehicle control, n=6, FIG. 43D), which were not significantly altered post-treatment. Immunostaining was performed to determine localization of IL8 in tissues. This demonstrated a weak diffuse staining pattern in 3D cultured FTE samples that was primarily localized to the stromal compartment of the cultures. These data confirm human fimbriae remain metabolically active ex vivo.

p53 Stabilization is not Enhanced by Ovulatory Factors Ex Vivo p53 induction in 3D cultures was evaluated, as its stabilization in secretory FTE is hypothesized to be a potential precursor to HGSC. As with proliferation studies, 3D fimbriae samples were treated for 2 and 7 days with insulin, $H_2O_2$, and $E_2$ and compared with uncultured and vehicle control treated tissues (n=8, FIG. 44A). Although no factor notably induced p53 stabilization at either time point, the ex vivo culture process alone appeared to induce p53 expression. Similar to in vivo 'p53 signatures', p53 stabilization was often limited to the secretory FTE, as noted by PAX8 expression (FIG. 44B). p53 expression was quantified by the number of consecutive positive cells (as with the SEE-FIM protocol), with 12 cells denoting a full p53 signature. These data demonstrate an ex vivo 'forgery' of the p53 signature can be produced that is similar to in vivo signatures originally defined in high-risk patients. Moreover, it was identified that these areas of p53 stabilization were not always concomitant with DNA damage (pH2AX staining), indicating p53 expression in the fallopian tube was not always in response to damage repair. p53 and pH2AX staining were not apparent in uncultured normal fallopian tissues.

Example 7

Endocervical Cultures in 3D Microphysiologic Setting

Experiments were conducted during development of embodiments of the present invention to culture human endocervical tissues in a microfluidic culture system, such that the cultured tissue is a physiologic mimic of in vivo biology and responds to estrogen and progesterone.

The endocervix has both anatomical and biological functions that participate in the delicate balance between tolerance necessary for conception and protection from pathogens. Experiments were conducted during development of embodiments of the present invention to develop a robust three-dimensional (3D) endocervix model that is a reliable representation of the in vivo tissues and to identify the physiological responses to changing levels of steroid hormones during a 28-day time period. Such a model provides a endocervical subsystem for incorporation into a microphysiologic system mimicking the entire female reproductive tract.

Human endocervical cells were grown on polystyrene scaffolds and the morphologic and hormonal responses of cultured cells were assessed in response to fluctuating levels of estradiol (E2) or progesterone (P4). Morphologically, the 3D cultures were composed of a mixed population of cells including epithelial and stromal cells. Treatment with E2 and P4 (day-28) increased cell growth and proliferation as compared to no treatment control. Cells expressed estrogen receptor (ER) and progesterone receptor (PR) and produced both neutral and acidic mucins, including MUC16. In addition, a 45-plex Luminex assay identified numerous factors secreted and regulated by hormones. Specifically, Interleukin-1 beta (IL-1β) and Leukemia Inhibitory Factor (LIF) significantly decreased in the presence of E2 and P4 as compared to the no hormone control at day-26. Co-treatment with RU486 attenuated the progesterone-driven inhibition of IL-1β and LIF secretion. A robust 3D endocervical culture was developed and physiologic responses to the menstrual cycle mimic of estradiol and progesterone levels for a period of 28 days were identified.

Tissue Collection

Endocervical tissue samples were collected from women undergoing routine hysterectomies at Northwestern University Prentice Women's Hospital (Chicago, Ill.), according to an IRB-approved protocol. Written consent was obtained from all women included in the study.

Isolation and Expansion of Primary Human Endocervical Cells

The mucosal epithelium and the underlying stroma of the endocervix were separated from the muscular tissue, minced under sterile conditions into 1- to 2-mm fragments and subjected to enzymatic digestion with 1.51 mg/ml collagenase I (Invitrogen, NY) and 5 mg/ml DNase I (Sigma, MO) in 20 ml Hanks' balanced salt solution (HBSS, Invitrogen, NY). After digestion for 1-2 h at 37° C. shaker (100 rpm), cells were washed, resuspended in keratinocyte-serum free medium (KGM-Gold, Keratinocyte Growth Medium Bullet Kit, Lonza, N.J.), plated on plastic culture dishes and cultured at 37° C. in a humidified atmosphere containing 5% $CO_2$. Media was changed every 2-3 days.

3D Cell Cultures and Hormonal Treatment

A commercially available, highly porous polystyrene scaffold, Alvatex® (Reinnervate Ltd, Sedgefield, UK) was used for 3D cultures. The membranes are 200 microns thick with pore sizes of 36-40 microns and the 12-well TRANSWELL format was used. Scaffolds were incubated with sterile filtered EtOH (70%) for 5 min as a pretreatment, washed twice with medium and left in medium. Primary endocervical cells were trypsinized from 2D cell cultures and each scaffold TRANSWELL was seeded with 2×10⁶ cells in a total volume of 100 μl medium (FIG. 1). The cells were allowed to attach for 1 h and media was gently added to the lower chamber for complete coverage with 3.5 ml media. Media was changed every 48 h.

Figure 45:
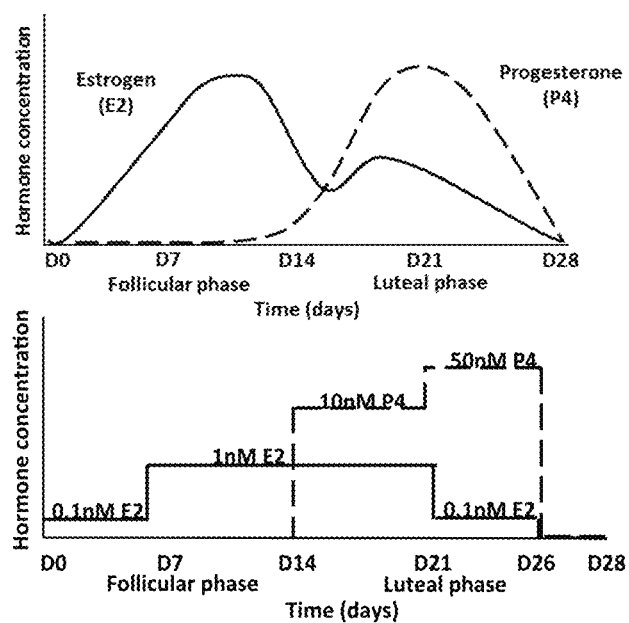
FIG. 45. Cell viability following a step hormone treatment for 28-days. (A) Primary endocervical cells were treated with estradiol (E2) and progesterone (P4) in a stepwise fashion; 0.1 nM E2 for 7 days, 1 nM E2 for the next 7 days, followed by 1 nM E2+P4 10 nM for 7 days, then 0.1 nM E2+P4 50 nM for 5 days and only media (no hormones) for 2 days for a total culture period of 28 days. (B) Endocervical cells were infected with 2 µl of pAD-eGFP-RLC (Ad-GFP) at day-0 of hormonal treatment. By the end of 28-day treatment regimen, viable endocervical cells were present, as visualized with fluorescence in GFP infected cells. The background was shown in red. The adherent uninfected cells can be observed by bright-field microscopy, in which reduced light reflection is a result of increased cell density observed specially in the presence E2+P4. Magnification 40×. (C) Cell viability was measured by Alamar blue staining. Data points on the graph represent the means±SD of four independent experiments. Statistical comparisons (student t-test) between E2 and E2+P4 were performed ($p<0.05$).
Figure 45:
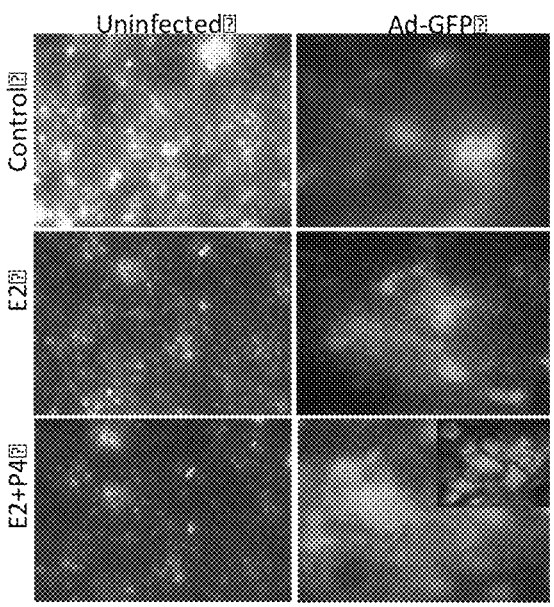
Figure 45:
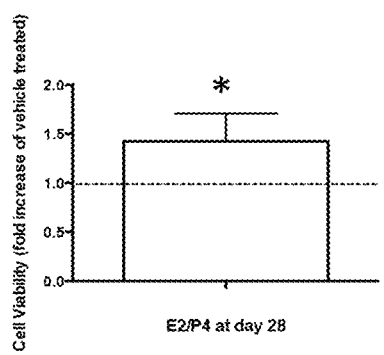

To represent a 28-day human menstrual cycle in vitro, a stepwise hormone regimen was added to the cells. For the first 7 days, cells were incubated with 0.1 nM E2, followed by 1 nM E2 for the next 7 days (FIG. 45). Then cells were treated for 1 nM E2 and 10 nM P4 for an additional 7 days, followed by 0.1 nM E2 and 50 nM P4 for 5 days. Then media without hormones were added for the final 2 days for a total culture period of 28 days. Media was collected every 48 h and stored at −20° C. For PR antagonist studies, cells were treated with 100 nM RU486 (Sigma, MO) which was added on day-21. To visualize the cells on scaffold, cells were infected with the adenovirus containing pAD-eGFP-RLC (Cell Imaging Core, Northwestern University) (Khuon et al. Journal of cell science 123:431-440; herein incorporated by reference in its entirety) by adding 2 μl of amplified virus to 3.5 ml of media per TRANSWELL for 24 h.

Cell Viability

The Alamar Blue Cell Viability Assay (Invitrogen, NY) that measures metabolic activity was used to measure cell viability. 350 μl of Alamar Blue reagent was added directly to the cells at the end of 28-day hormonal treatment. Cells were incubated at 37° C., 5% $CO_2$ for 4 h in the dark and the fluorescence was measured at 570/585 nm.

Immunohistochemistry

Scaffolds were washed twice in PBS, covered with histogel (Fisher Scientific, MA) and fixed in 4% paraformaldehyde for 5 h. Processing and hematoxylin and eosin (H&E) staining was performed at the Northwestern University Center for Reproductive Sciences Histology Core (Chicago, Ill.). Fixed cells were processed using an automated tissue processor (Leica) and embedded in paraffin. Serial sections were cut 10 μm thick, mounted on glass slides and stained with H&E using a Leica Autostainer XL (Leica Microsystems). Antigen retrieval was performed by treatment for 10 min in buffer containing 0.05% Trypsin and 1% CaCl2 at pH 7.6. After blocking, sections were incubated with primary antibodies to PR (1:200, Dako, Calif.), ER (1:100, Abgent, Calif.), vimentin (1:200, Abcam, MA), pan cytokeratin (1:500, Abcam, MA), Ki67 (1:100, Abcam, MA) and MUC16 (1:100, Abcam, MA) overnight at 4° C. Slides were rinsed and HRP-conjugated secondary antibodies were applied for 30 min. HRP activity was detected using 3,3'-Diaminobenzidine (DAB) in 1:50 dilution (Dako, Calif.) as substrate for 30-60 sec and then counterstained with hematoxylin. Sections incubated with dilution buffer without primary antibody were used as the negative control. For immunofluorescent staining, antigen retrieval was performed by treatment for 10 min in buffer containing 0.05% Trypsin and 1% CaCl at pH 7.6. Sections were washed 2× in TBST, blocked with protein block for 30 min (Dako, Calif.) and incubated with primary antibodies described above. Slides were rinsed in TBST and incubated with fluorescent secondary antibodies (1:250; Invitrogen, NY) for 1 h. Slides were visualized and images captured with Leica DM5000B Microscope.

Staining for Neutral and Acidic Mucins

Sections stained with Periodic Acid Schiff (PAS) (Abcam, MA) were previously deparaffinized and oxidized in 1% periodic acid for 10 min, followed by several rinses in distilled water. Staining was carried out in Schiff's reagent at 4° C. for 30 min followed by rinsing in distilled water. Sections were then counterstained with hematoxylin for 2 min, washed, dehydrated and mounted. In addition, deparaffinized and hydrated sections were treated with acetic acid solution for 3 min, stained with Alcian blue (Abcam, MA) for 30 min, followed by a wash in running tap water for 10 min. After counterstaining with Safranin O solution for 5 min, sections were washed, dehydrated, and mounted.

Cytokine/Chemokine Quantitation

ProcartaPlex Human Cytokine/Chemokine/Growth Factor Panel 1 (45-plex) (Affymetrix eBioscience, CA) was used to measure levels of secreted cytokines and chemokines. For quantification, duplicate standards produced a curve for each analyte from which concentrations of samples were extrapolated. Medium alone was used to establish background levels of cytokines and chemokines. The levels of LIF, IL-1β (Abcam) and MUC16 (R&D) were validated using single ELISA assays and performed according to manufacturer's protocol.

Establishment of an Ex Vivo 3D Endocervix

Figure 46:
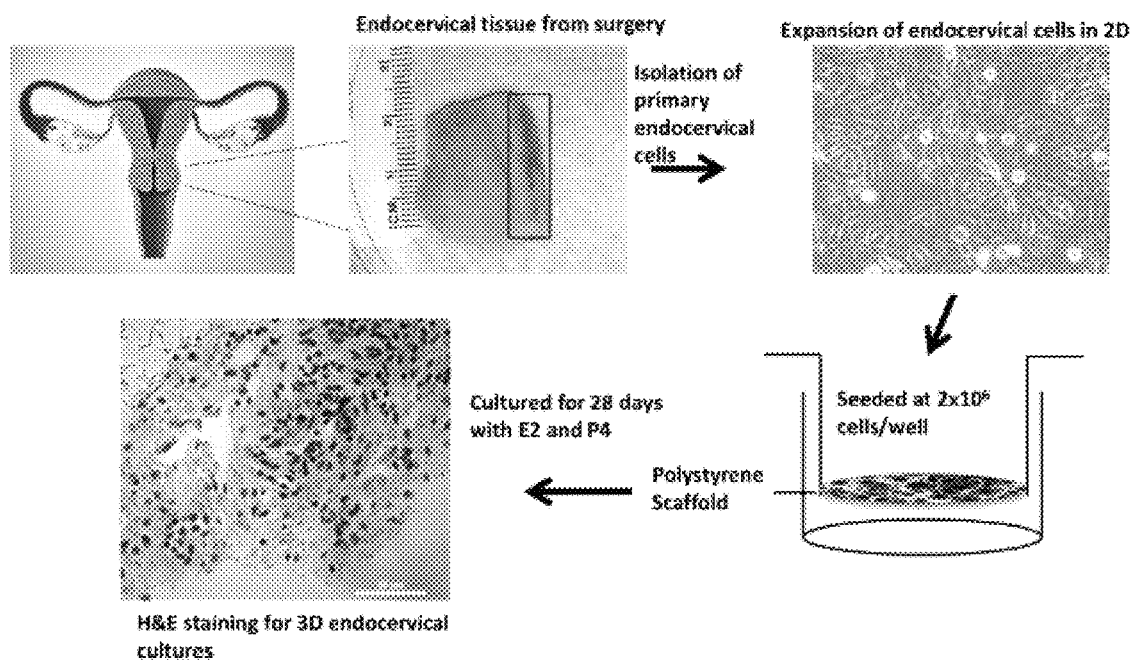
FIG. 46. Establishment of 3D cultures of the human endocervix. The endocervix tissue was obtained post-surgery and tissue was enzymatically digested. Cells were cultured on 2D culture plates and expanded. Cells were trypsinized and seeded at 2×10⁶ cells/well onto the polystyrene scaffold membrane. Cells were cultured for 28-days in the presence of steroid hormones. The 3D units were fixed and processed for hematoxylin and eosin (H&E) staining.

Human endocervix tissues obtained post-surgery were enzymatically digested and expanded in 2D cultures to obtain a sufficient number of cells (FIG. 46). Two million cells were seeded on the highly porous polystyrene scaffolds, Alvetex® membranes (FIG. 46) (Knight et al. Methods in molecular biology 695:323-340; Bokhari et al. Journal of anatomy 211:567-576; Stevanato & Sinden Stem cell research & therapy 5:49; herein incorporated by reference in their entireties) and immediately treated with E2 and P4 in a stepwise fashion to mimic a 28-day menstrual cycle in vitro (FIG. 45A). At 14-day (E2 only) and 28-day (E2+P4) time points, viable endocervical cells were present, as visualized with GFP florescence (FIG. 45B). The cell viability assay demonstrated viable cells at 28-days. This assay also showed a subtle but significant increase in cell viability with E2+P4 treatment at day 28 compared to vehicle treated control (p<0.05) (FIG. 45C). These data demonstrate that endocervical cells cultured on the 3D scaffolds survive and grow in response to a 28-day culture with hormones.

Histological Analysis of 3D Cultures

Figure 47:
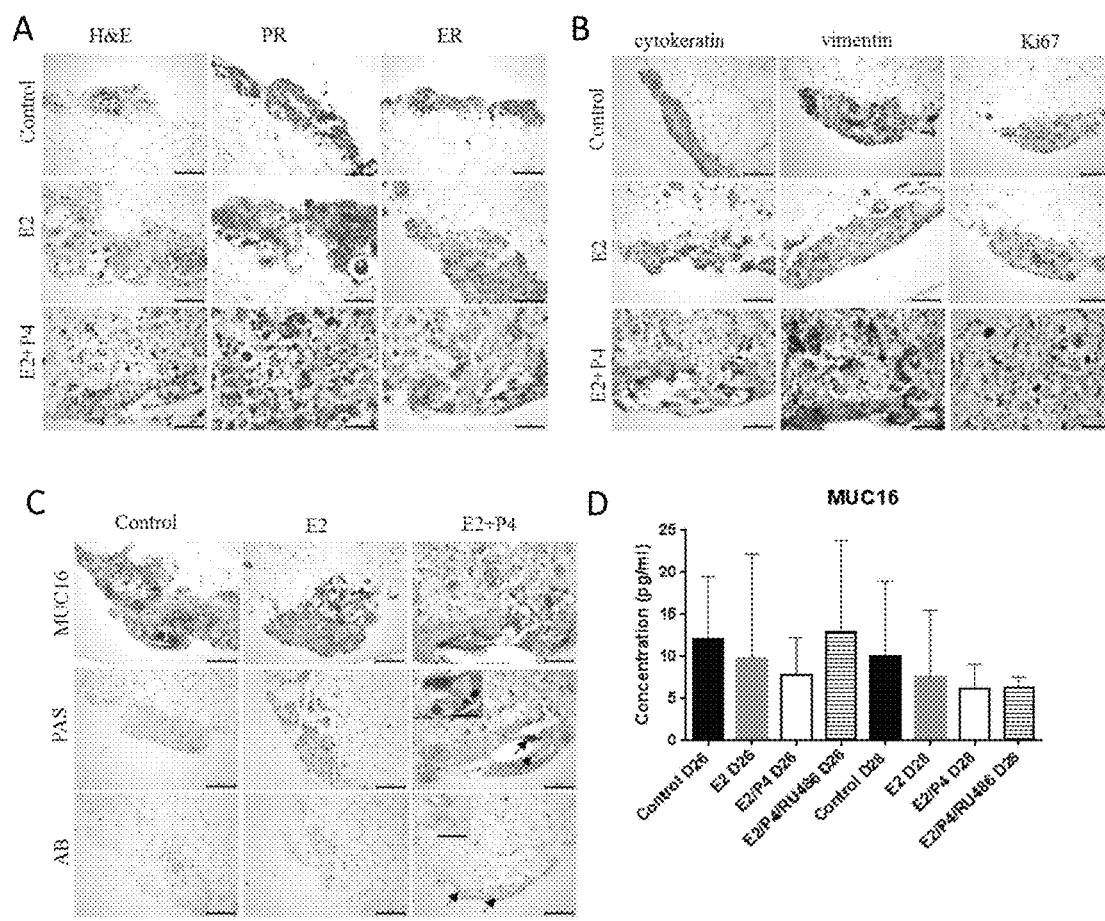
FIG. 47. Expression of endocervical cell markers. Cells in the polystyrene scaffold were fixed, processed and (A) stained with hematoxylin and eosin (H&E) at day-14 (E2-only) and day-28 (Control and E2+P4). (A) Immunohistochemical staining for estrogen receptor (ER), progesterone receptor (PR), (B) pan cytokeratin, vimentin and Ki-67 was done. (C) MUC16 levels were detected by IHC staining, neutral mucins by Periodic Acid Schiff (PAS) staining and acidic mucins by Alcian blue (AB) at day-14 (E2) and day-28 (Control and E2+P4) in 3D endocervical cells. The PAS stain revealed the presence of goblet cells (arrow). Alcian blue staining detected acidic mucins (arrow). Figures are representative of at least three independent experiments. Scale bars represent 25 μm (inset) and 50 μm. (D) Cells were treated with 100 nM RU486. Levels of MUC16 released into the culture media were measured by ELISA. Data are means±SD from three patient samples.

H&E staining of the 3D cultures revealed the presence of a mixed population of cells (FIG. 47). Pan cytokeratin and vimentin staining showed both epithelial and stromal cells, respectively, present in the endocervical cultures at day-14 (E2) and day-28 (E2+P4). In addition, cells expressed both PR and ER, which increased in the presence of E2 and P4 as compared to control. Furthermore, the Ki67 staining was evident in the cultures with increased staining in the presence of E2, or E2 and P4 as compared to control (FIG. 47) indicative of active proliferation of cells, even after 28 days of culture.

Expression and Secretion of Endocervical Mucus

One of the major functional properties of the endocervix is the production and secretion of mucus. Immunohistochemical staining showed production of the mucin, MUC16 (FIG. 47C). Estrogen and progesterone did not appear to affect levels of MUC16 compared to control cultures. In addition, levels of MUC16 secreted into the culture media did not significantly change at day-26 and day-28 of the hormone treatment regimen compared to untreated cultures (FIG. 47D). Moreover, the progesterone receptor antagonist, RU486 in the presence of E2 and P4 did not significantly alter levels of secreted MUC16 (FIG. 47D), indicating that hormones were not modulating the production and secretion of MUC16 in the 3D endocervix cultures. In contrast, the neutral mucins, as measured by Periodic Acid Schiff (PAS) staining, increased with E2 and P4 (day-28) treatment compared to control or E2 (day-14) treatments (FIG. 47C). This stain also detected the presence of goblet cells at the end of the 28-day hormonal treatment (FIG. 47C). The acidic mucins were detected using the Alcian blue stain. In contrast to the PAS stain, no difference in the levels of acidic mucins with the hormonal treatments was observed (FIG. 47C).

Cytokine/Chemokine Profile of 3D Cultures

Figure 48:
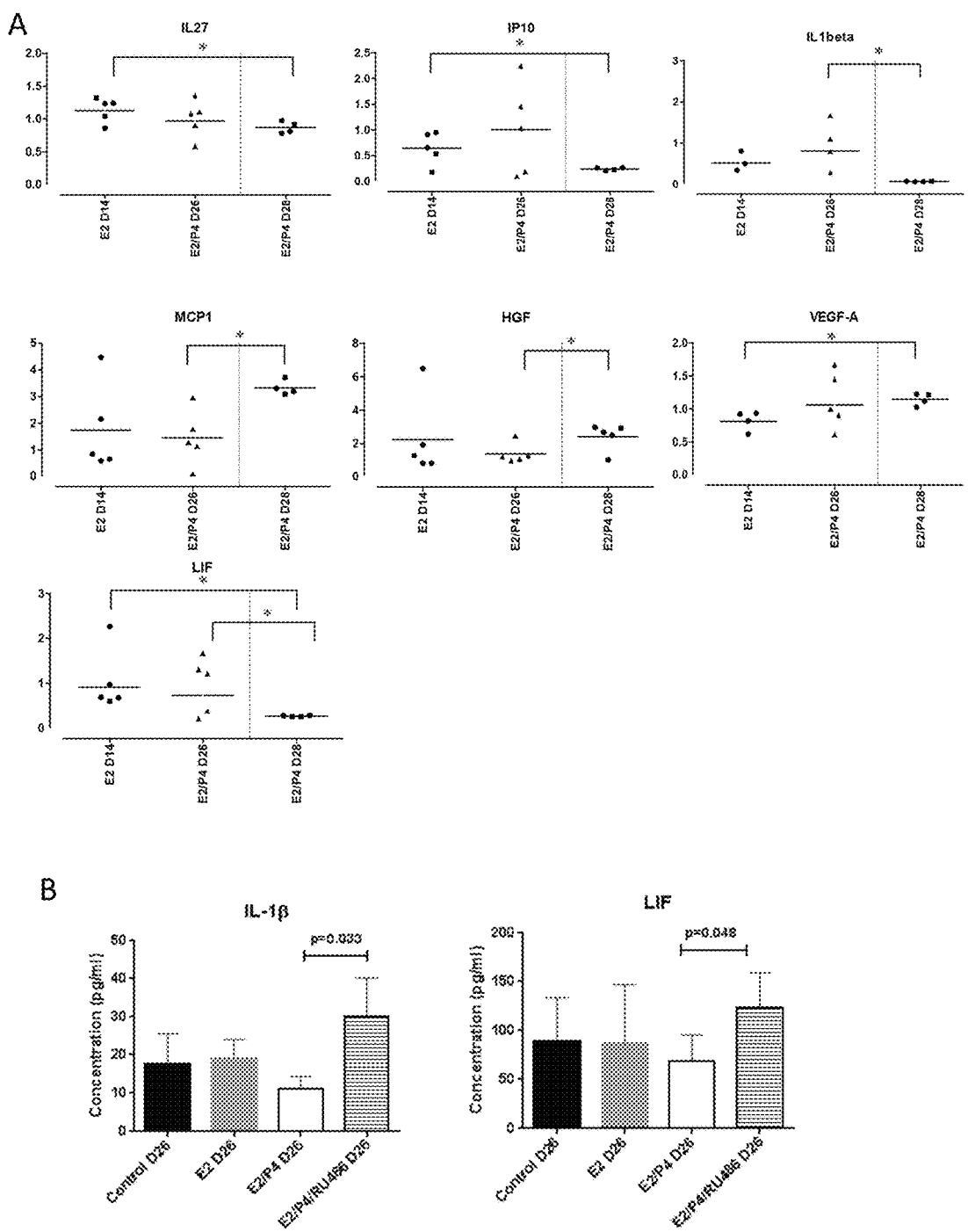
FIG. 48. Hormonal regulation of IL-1β and LIF. Endocervical cells in 3D were treated with the step hormone treatment. (A) A 45-plex Luminex assay was performed, using media collected at D14, D26 and D28. Data are presented as fold changes from vehicle controls (n≥4 patient samples). * denotes $p<0.05$. (B) IL-1β and LIF levels were validated by ELISA. RU486 was added to the cells at D21. Data are mean±SD from 3 patient samples. Statistical comparisons among all treatments were performed ($p<0.05$).

The cytokine/chemokines secreted by the 3D endocervical cultures were measured using a 45-Plex Luminex assay. Levels of factors secreted into the culture media at day 14, 26 and 28 were measured during the step hormone treatment. Out of 45 factors, 36 were detectable by this assay. There was a wide range in concentrations of factors secreted by the 3D cultures; 17 factors measured less than 25 pg/ml consistently within the replicates. Due to the variation among patient samples, data was expressed as fold changes of hormone treated with its respective control (vehicle treated) (FIG. 48A). Fold changes were then compared between the three time points, day 14, 26 and 28. Seven factors, IL27, IP10, IL-1β, MCP1 HGF, VEGFA, and LIF showed fold changes that were statistically different between day 14 and day 28 (IL27, IP10, VEGFA and LIF) or between day 26 and day 28 (IL-1β, MCP1, HGF, and LIF). Validation of two factors, IL-1β and LIF using single ELISA assays and different patient samples, demonstrated that E2 and P4 treatment decreased the secretion of these factors at day 26 (FIG. 48B). Treatment of cultures with RU486 starting from day 21 attenuated the inhibition of IL-1β and LIF that occurred with E2 and P4, demonstrating specific regulation by progesterone through its receptor (FIG. 48B).

Example 8

Ectocervical Cultures in 3D Microphysiologic Setting

Experiments were conducted during development of embodiments of the present invention to culture human ectocervical tissues in a microfluidic culture system, such that the cultured tissue responds to ovarian hormones.

Figure 49:
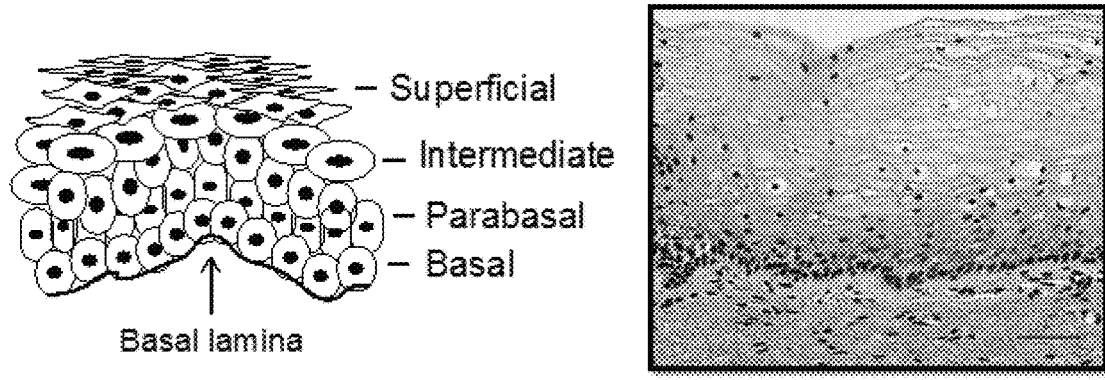
FIG. 49. The four layers of the ectocervix.
Figure 50:
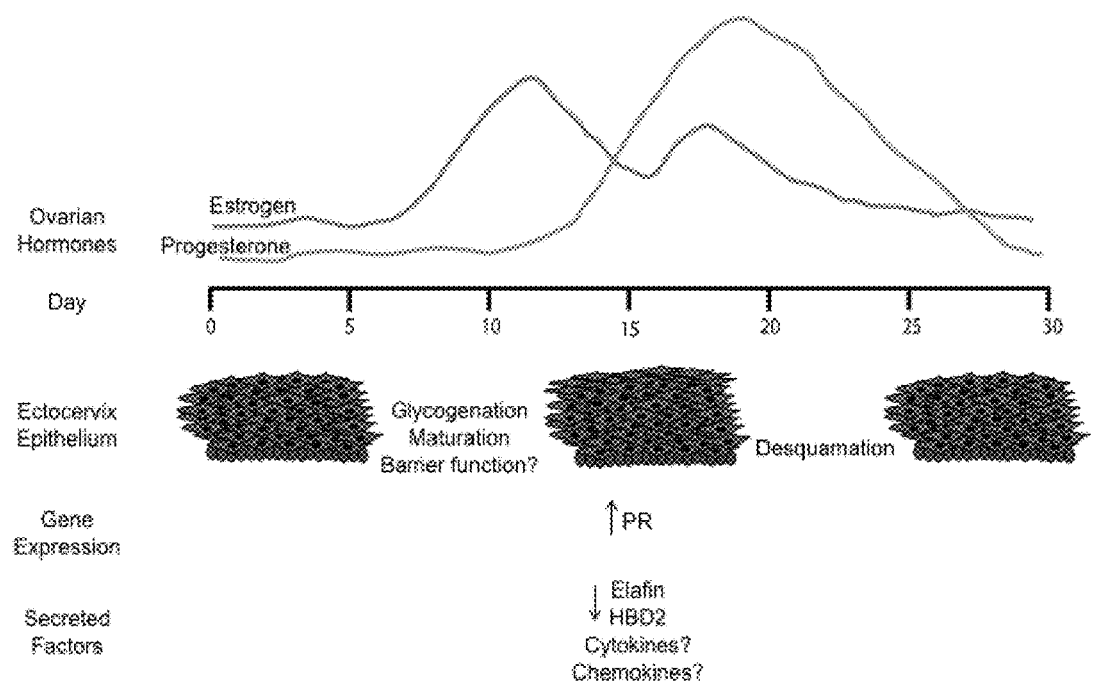
FIG. 50. The ectocervix changes throughout the menstrual cycle in response to ovarian hormones, our model should recapitulate these changes by becoming glycogenated and differentiating into a mature stratified squamous epithelium in response to estrogen. As estrogen levels drop off, the most superficial layer of cells is shed in a process known as desquamation. Additionally, progesterone receptor expression should increase in response to estrogen, whereas the secretion of antimicrobial peptides will decrease in response to estrogen. This model will be used to determine hormonally regulated mechanisms involved in barrier function, and to discover additional hormonally regulated secreted factors, such as cytokines and chemokines.

The ectocervix epithelium comprises four primary layers: superficial, intermediate, parabasal, and basal layers (FIG. 49). The cells of these layers undergo changes throughout the menstrual cycle (FIG. 50). A 3D culture subsystem was designed comprising cells of each of the four layers. The culture subsystem recapitulates these changes by proliferation and differentiating in response to estrogen. Additionally, progesterone receptor expression increases in response to estrogen, whereas the secretion of antimicrobial peptides will decrease in response to estrogen.

Figure 51:
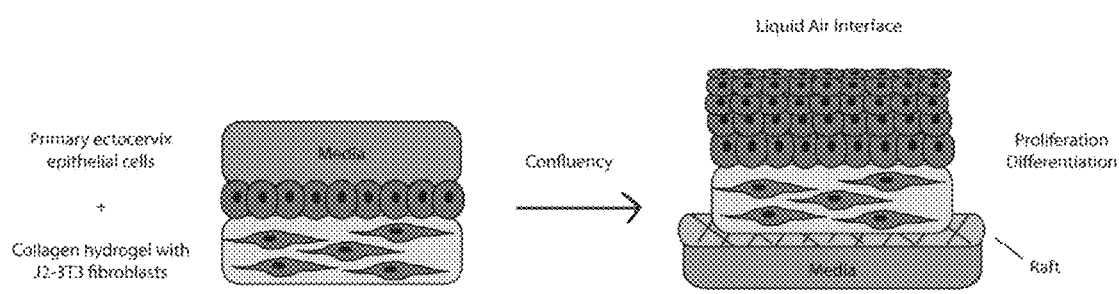
FIG. 51. Establishment of static 3d cultures of primary epithelial cells using collagen hydrogels and J2-3T3 stromal fibroblasts at a liquid-air interface.

Experiments were conducted to establish static 3D cultures of primary epithelial cells from the ectocervix (FIG. 51):

a. Collagen plug with J2-3T3 fibroblasts
  1. Detached J2-3T3 cells with 0.05% trypsin and count cells –400,000 cells per 1.5 ml plug.
  2. Spun down appropriate amount of cells and resuspend in ⅒ volume reconstitution buffer (1.95 ml).
  3. Added ⅒ volume 10×DMEM (1.95 ml) and rocked gently to mix.
  4. Added collagen to a final concentration of 4 mg/ml and rocked gently.
  5. Added 0.5 N NaOH until color resembled watermelon pink—neutral.
  6. Added ddH2O to reach final volume (19.5 ml).
  7. Added 1.5 ml collagen solution to each well of a 12-well plate.
  8. Incubated plates at 37° C. for 30 minutes to allow collagen to polymerize.
  9. Added 3 ml J2-3T3 media to each well.
  10. Incubated at 37 C for 2 days. Collagen plug was viable for up to 4 days. Media on plug changed every other day.

b. Seeding epithelial cells on collagen plug
  1. Removed existing J2-3T3 media from collagen plugs, taking care not to touch the collagen.
  2. Added 2 ml E media (below)+5 ng EGF to each well to submerge collagen plug.
  3. Removed feeder layer from 2D cell cultures, then trypsinized and counted cells
  4. Resuspended cells in 1 ml/well E media.
  5. Added 1 ml of cell suspension to each well (for a total of 3 ml per plug).

6. Incubate at 37 C until confluent, changing media every day.

3D ectocervix raft culture: liquid-air interface
1. Removed media from collagen plug, taking care not to touch the collagen.
2. Removed collagen plugs from wells by inserting sterile spatula between the well and plug in an up and down motion on all side of plug, and then carefully scooped underneath plug and placed it on metal grid in a 60 mm plate.
3. Added fresh E media+EGF to each of the 60 mm plates up to the bottom of the grid.
4. Changed media every 2 days until harvest.

E media (1 L): 458.5 ml DMEM HG, 458.5 ml DMEM:F-12, 10 ml E cocktail mix (below), 200 µl gentamicin (10 µg/ml), 1 ml Amphotericin B (0.25 µg/ml, 20 ml 4 mm L-Glut (200 mM), 1 ml hydrocortisone (0.4 µg/ml).

E cocktail mix: 180 µM adenine, 5 µg/ml human recombinant insulin, 5 µg/ml human apo-transferin, 5 µg/ml triiodothyronine, T3 and 1 ml cholera toxin (10 ng/ml).

Figure 52:
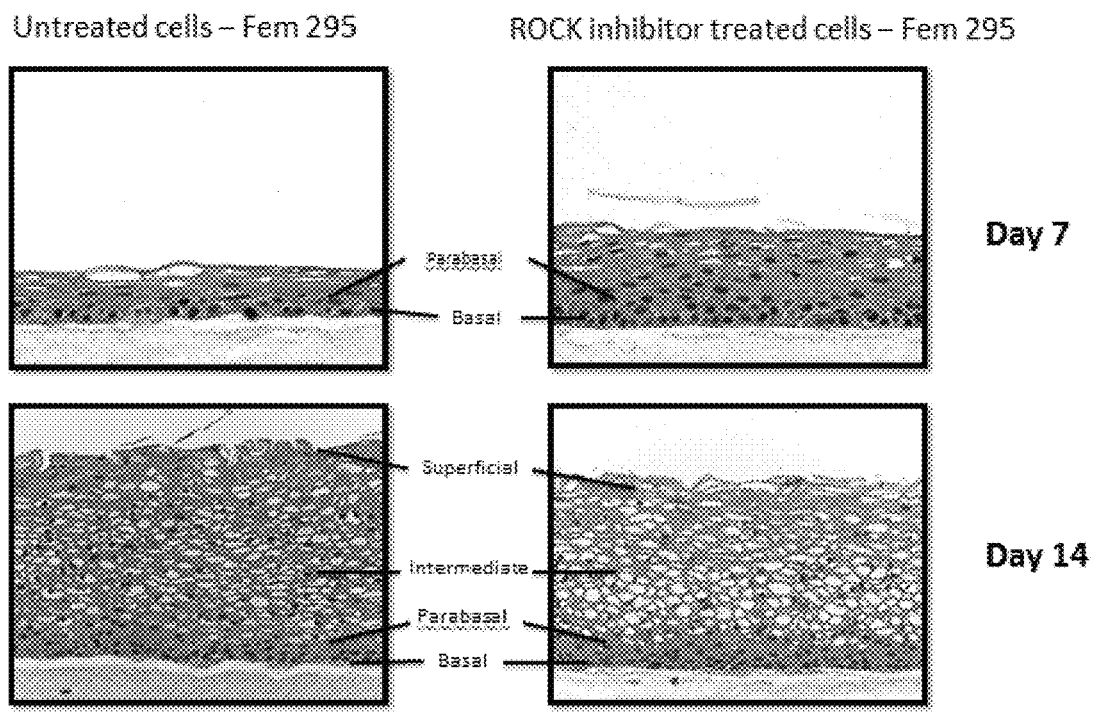
FIG. 52. The day 7 models showed the basal and parabasal layers had formed, with the more superficial layers beginning to form in the ROCK inhibitor treated cells. By day 14, all four layers were apparent in both the primary and ROCK inhibitor treated cells. Glycogenation was apparent in the intermediate and superficial layers, shown by large white spaces in the cytoplasm, a sign of normal maturation and development of the stratified squamous epithelium.
Figure 53:
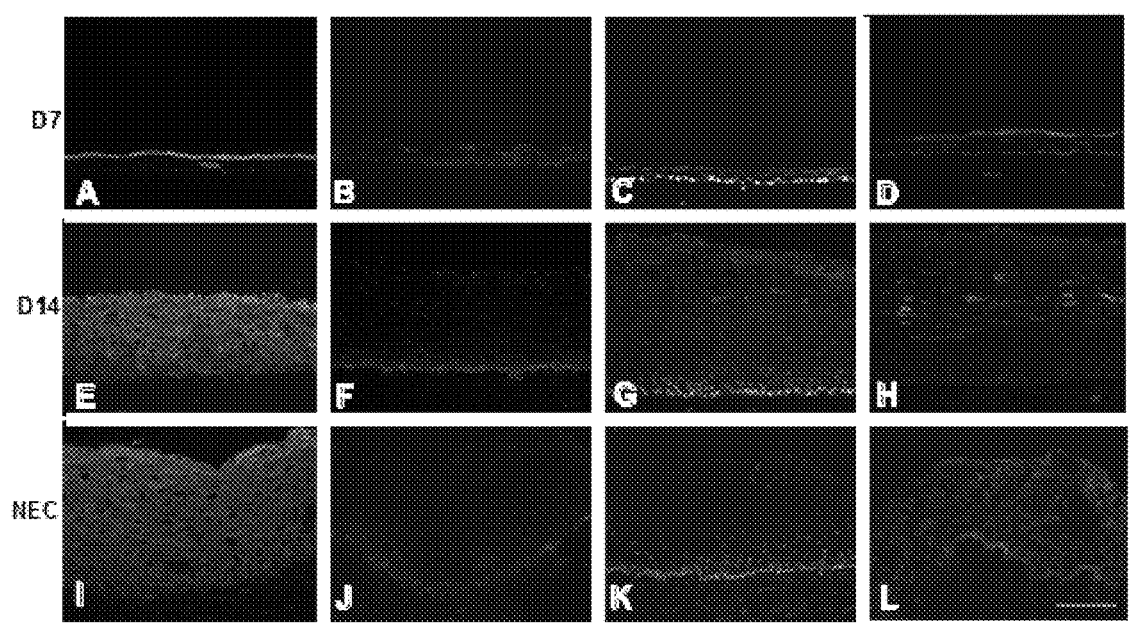
FIG. 53. Cultures were harvested after 7 and 14 days for immunohistochemical analysis of ectocervix and differentiation markers. All differentiation markers were detected as early as 7 days in culture (A-D), and mimicked expression patterns of normal ectocervix tissue (NEC) (I-L) by day 14 (E-H). CK13, expressed in non-keratinizing stratified squamous epithelium, was found in the parabasal, intermediate and superficial layers (A, E, I). CK14, a stratified squamous basal layer marker, was present in the models and NEC (B, F, J). P63 drives differentiation in the ectocervix and was expressed in the basal and parabasal layers (C, G, K). MUC4 plays a role in lubrication, hydration and barrier protection in the ectocervix and was expressed throughout the epithelium in both the models and NEC (D, H, L). Scale bar=50 um.

The basal and parabasal layers had formed by day 7, with the more superficial layers beginning to form in ROCK inhibitor treated cells. By 14 days, all 4 layers were apparent in both the primary and ROCK inhibitor treated cells (FIG. 52).

Example 9

Decellularizing Human Ectocervix Tissue

Experiments were conducted during development of embodiments of the present invention to decellularize human ectocervix tissue according to the following exemplary protocol:
1. Wash tissue with PBS+antibiotics to remove contaminants.
2. Cut a small piece and flash freeze in LN2 for later DNA comparisons.
3. Cut a small piece and fix in 4% PFA for histology.
4. Place remaining tissue in 50 ml 0.1% SDS on a rocker at RT.
5. Place tissue in fresh 50 ml 0.1% SDS and place on rocker at RT for an additional 1-2 days.
6. Place tissue in 50 ml PBS and place on rocker in cold room overnight.
7. Replace with 50 ml fresh PBS and continue washing overnight at 4 C.
8. Place tissue in PBS with 1 mg/ml BSA and 0.05% sodium azide and store at 4 C until needed.

Example 10

Differentiation of iPSCs into Intermediate Mesoderm Lineage

Experiments were conducted during development of embodiments of the present invention to differentiate induced pluripotent stem cells (iPSCs) according to the following exemplary protocol:

Embryoid Body Formation:
1. iPSCs are 85-90% confluent before embryoid body formation, and there is less than 10% differentiation per well. Embryoid bodies are formed in the same size well that the confluent iPSCs were originally plated (1:1).
2. Wash iPSCs were versene, then add 1 ml of versene to each well and incubate at room temperature for 6 minutes.
3. Lift cells in E8 media and pool in a 15 ml conical.
4. Centrifuge at 1000 rpm for 5 minutes to form pellet.
5. Add 2 ml/well of E8 with PVA to non-adherent 35 mm plates.
6. Resuspend cell pellet in 0.5 ml/well E8 with PVA.
7. Add 1 ul/well ROCK inhibitor.
8. Add 0.5 ml cell suspension drop wise to prepared 35 mm plates.
9. Incubate at 37° C. overnight—embryoid bodies will form within two days.

Embryoid Bodies to Intermediate Mesoderm
1. Carefully remove media from embryoid bodies by tilting the plate to a 45 degree angle and allowing embryoid bodies to settle at the bottom. Aspirate as much media as possible without disturbing embryoid bodies.
2. Replace with 2 ml maintenance media with BMP4 for 1 day.
3. Replace media with 2 ml intermediate mesoderm differentiation media, changing media every day for 3 days.
4. Plate cells on fibronectin coated plate in intermediate mesoderm media, changing media daily until morphologically desirable.
5. Analyze for IM and pluripotent markers.

Example 11

Harvesting 3D Ectocervix Rafts

The following exemplary protocol was used for harvesting 3D ectocervix rafts produced, for example, as described above:
1. Discard media (or save media if needed for future analysis).
2. Flood raft with PBS (with calcium) to completely submerge the entire raft.
3. Gently remove collagen plug from grid, without disturbing the epithelial layer. Use forceps to gently pick the plug around the edges, or use scissors to cut away the plug from the raft.
4. Once collagen plug is completely removed and floating, push to the side and remove grid; do not flip or disturb the collagen plug.
5. While holding plug to the side, remove PBS from dish.
6. Cut three parallel sections: one for RNA, OCT and protein. The very center section will be for OCT.
7. Set aside the middle piece for OCT and remove the epithelial layers from the two side pieces by using forceps to gently pull the cell sheet away from the collagen.
8. Place epithelial sheets in either Trizol for RNA processing or Urea buffer for protein analysis and let sit several minutes.
9. Trim the section for OCT, removing the ends and leaving a piece that will fit nicely in the OCT tissue chamber.
10. Fill chamber about ½ full with OCT, place on metal block in LN2 until slightly (but not completely) frozen—will be white but still transparent at the top.
11. Place tissue onto OCT in chamber, being careful not to stretch it. Make sure the tissue is not folded and is in the correct orientation.
12. Place on metal block in LN2 and fill the chamber with OCT, covering tissue, without air bubbles.
13. Leave on metal block until completely frozen, while completing RNA and protein 14. Use needles and syringes to break down the tissue for RNA and protein:
    RNA: 18 gauge, then 22 gauge
    Protein: 18 gauge, then 22 gauge, then 26 gauge
15. Store all at −80 C until needed.

Example 12

Primary Ectocervix Cell Culture

The following exemplary protocol was used for 3D culturing of 3D ectocervix cells:
Epithelial Cell Isolation
1. Wash tissue in PBS+antibiotics to remove any contaminants.
2. Cut tissue into small pieces (<5 mm) and place in 60 mm dish with 3 ml dispase in 4 C fridge overnight.
3. Remove epithelial layer by using two pairs of forceps, one to anchor the tissue, and one to gently peel off epithelial layer.
4. Place epithelial layers flat in 4 ml 0.25% trypsin in a 60 mm plate for 10 mins at 37° C.
5. Add 500 µl FBS to neutralize trypsin.
6. Add 5 ml PBS and pipette up and down to release cells.
7. Transfer to 15 ml conical and centrifuge at 1000 rpm for 5 minutes.
8. Resuspend in FAD or keratinocyte media and plate on J2-3T3 feeder layer. Change media the day after plating Change feeder layer and media every 2 days after plating. Follow differential trypsinization protocol for passaging and changing feeder layer.

Feeder Layer Preparation:
1. Treat J2-3T3 cells with Mitomycin C for 2-2.5 hours.
2. Wash cells 3× with PBS to remove mitomycin C.
3. Add 1 ml 0.05% trypsin and incubate at RT for 2 minutes.
4. Neutralize with FAD media and transfer to a 15 ml conical.
5. Centrifuge at 1000 rpm for 5 minutes.
6. Resuspend in FAD media and distribute to plates for epithelial cell co-culture.

Stromal Fibroblast Isolation:
1. After removing epithelial layer from tissue with dispase, cut remaining tissue into smaller pieces (<2 mm) and place in 100 mm plate for 10 minutes at RT to allow tissue to stick to plate.
2. Add 1 drop of 0.25% trypsin to each piece (about 1 ml total) and incubate at 37° C. for 2.5-3 hours (Alternative: use 0.05% trypsin and increase incubation time to 8 hours).
3. Flood plate with 7 ml J2-3T3 media.
4. Change media the following day and then every 2 days after that.
5. Remove tissue once fibroblasts are growing out from the tissue pieces onto the plate.
6. Passage with 0.25% trypsin once cells reach confluency.

Differential Trypsinization:
1. Remove media and replace with 4 ml Versene for 5-10 minutes at RT.
2. Pipette versene to remove fibroblasts and confirm detachment with microscope.
3. Remove versene and add 1 ml 0.05% trypsin for 5-7 minutes at 37 C. Confirm detachment under microscope.
4. Neutralize trypsin by adding 3-4 ml FAD media, and transfer to 15 ml conical.
5. Centrifuge at 1000 rpm for 5 minutes at RT.
6. Resuspend cells in FAD media and plate on freshly prepared feeder cells.

The foregoing embodiments and examples are intended only as examples. No particular embodiment, example, or element of a particular embodiment or example is to be construed as a critical, required, or essential element or feature of any of the claims. Various alterations, modifications, substitutions, and other variations can be made to the disclosed embodiments without departing from the scope of the present application, which is defined by the appended claims. The specification, including the figures and examples, is to be regarded in an illustrative manner, rather than a restrictive one, and all such modifications and substitutions are intended to be included within the scope of the application. Steps recited in any of the method or process claims may be executed in any feasible order and are not limited to an order presented in any of the embodiments, the examples, or the claims.

REFERENCES

The following references, as well as those included above, are herein incorporated by reference in their entireties.

Abel P D. 1974. Toxicity of synthetic detergents to fish and aquatic invertebrates. J. Fish Biol. 6: 279-298

Abel P D, Skidmore J F. 1975. Toxic effects of an anionic detergent on the gills of rainbow trout. Water Res. 9:759-765

Ahn R W, Barrett S L, Raja M R, Jozefik J K, Spaho L, Chen H, et al. 2013. Nano-encapsulation of arsenic trioxide enhances efficacy against murine lymphoma model while minimizing its impact on ovarian reserve in vitro and in vivo. PLoS one 8:e58491.

Albertini D F, Combelles C M, Benecchi E, Carabatsos M J. 2001. Cellular basis for paracrine regulation of ovarian follicle development. Reproduction 121:647-653.

Allan S E, Smith B W, Anderson K A. 2012. Impact of the deepwater horizon oil spill on bioavailable polycyclic aromatic hydrocarbons in gulf of mexico coastal waters. Environmental science & technology 46:2033-2039.

Andersen M E, Al-Zoughool M, Croteau M, Westphal M, Krewski D. 2010. The future of toxicity testing. Journal of toxicology and environmental health Part B, Critical reviews 13:163-196.

Anderson S E, Franko J, Lukomska E, Meade B J. 2011. Potential immunotoxicological health effects following exposure to corexit 9500a during cleanup of the deepwater horizon oil spill. Journal of toxicology and environmental health Part A 74:1419-1430.

Biggers J D, Whittingham D G, Donahue R P. 1967. The pattern of energy metabolism in the mouse oocyte and zygote. Proceedings of the National Academy of Sciences of the United States of America 58:560-567.

Borovskaya T G, Goldberg V E, Fomina T I, Pakhomova A V, Kseneva S I, Poluektova M E, et al. 2004. Morphological and functional state of rat ovaries in early and late periods after administration of platinum cytostatics. Bulletin of experimental biology and medicine 137:331-335.

Cole R D, Anderson G L, Williams P L. 2004. The nematode *caenorhabditis elegans* as a model of organophosphate-induced mammalian neurotoxicity. Toxicology and applied pharmacology 194:248-256.

Colonna R, Mangia F. 1983. Mechanisms of amino acid uptake in cumulus-enclosed mouse oocytes. Biology of reproduction 28:797-803.

Combelles C M, Carabatsos M J, Kumar T R, Matzuk M M, Albertini D F. 2004. Hormonal control of somatic cell oocyte interactions during ovarian follicle development. Molecular reproduction and development 69:347-355.

Cortvrindt R G, Smitz J E. 2002. Follicle culture in reproductive toxicology: A tool for in-vitro testing of ovarian function? Human reproduction update 8:243-254.

Craig Z R, Hannon P R, Wang W, Ziv-Gal A, Flaws J A. 2013. Di-n-butyl phthalate disrupts the expression of genes involved in cell cycle and apoptotic pathways in mouse ovarian antral follicles. Biology of reproduction 88:23.

Dash A, Blackman B R, Wamhoff B R. 2012. Organotypic systems in drug metabolism and toxicity: Challenges and opportunities. Expert opinion on drug metabolism & toxicology 8:999-1014.

Ducibella T, Buetow J. 1994. Competence to undergo normal, fertilization-induced cortical activation develops after metaphase i of meiosis in mouse oocytes. Developmental biology 165:95-104.

Eddie S L, Quartuccio S M, Zhu J, Shepherd J A, Kothari R, Kim J J, Woodruff T K, Burdette J E. Three-dimensional modeling of the human fallopian tube fimbriae. Gynecol Oncol. 2014 Dec. 16.

Eppig J J, Pendola F L, Wigglesworth K, Pendola J K. 2005. Mouse oocytes regulate metabolic cooperativity between granulosa cells and oocytes: Amino acid transport. Biology of reproduction 73:351-357.

Fortune J E, Rivera G M, Yang M Y. 2004. Follicular development: The role of the follicular microenvironment in selection of the dominant follicle. Animal reproduction science 82-83:109-126.

Gennari L, Merlotti D, Nuti R. 2011. Aromatase activity and bone loss. Advances in clinical chemistry 54:129-164.

George S E, Nelson G M, Kohan M J, Warren S H, Eischen B T, Brooks L R. 2001. Oral treatment of fischer 344 rats with weathered crude oil and a dispersant influences intestinal metabolism and microbiota. Journal of toxicology and environmental health Part A 63:297-316.

Goodbody-Gringley G, Wetzel D L, Gillon D, Pulster E, Miller A, Ritchie K B. 2013. Toxicity of deepwater horizon source oil and the chemical dispersant, corexit(r) 9500, to coral larvae. PloS one 8:e45574.

Hemmer M J, Barron M G, Greene R M. 2011. Comparative toxicity of eight oil dispersants, louisiana sweet crude oil (lsc), and chemically dispersed lsc to two aquatic test species. Environmental toxicology and chemistry/SETAC 30:2244-2252.

Holland J, Bandelow S, Hogervorst E. 2011. Testosterone levels and cognition in elderly men: A review. Maturitas 69:322-337.

Hook S E, Osborn H L. 2012. Comparison of toxicity and transcriptomic profiles in a diatom exposed to oil, dispersants, dispersed oil. Aquatic toxicology 124-125:139-151.

Keim M E. 2011. The public health impact of industrial disasters. American journal of disaster medicine 6:265-272.

Kenney L B, Laufer M R, Grant F D, Grier H, Diller L. 2001. High risk of infertility and long term gonadal damage in males treated with high dose cyclophosphamide for sarcoma during childhood. Cancer 91:613-621.

Kociba R J, Sleight S D. 1971. Acute toxicologic and pathologic effects of cis-diamminedichloroplatinum (nsc-119875) in the male rat. Cancer chemotherapy reports Part 1 55:1-8.

Krajnak K, Kan H, Waugh S, Miller G R, Johnson C, Roberts J R, et al. 2011. Acute effects of corexit ec9500a on cardiovascular functions in rats. Journal of toxicology and environmental health Part A 74:1397-1404.

Kujawinski E B, Kido Soule M C, Valentine D L, Boysen A K, Longnecker K, Redmond M C. 2011. Fate of dispersants associated with the deepwater horizon oil spill. Environmental science & technology.

Lenie S, Cortvrindt R, Eichenlaub-Ritter U, Smitz J. 2008. Continuous exposure to bisphenol a during in vitro follicular development induces meiotic abnormalities. Mutation research 651:71-81.

Meirow D, Lewis H, Nugent D, Epstein M. 1999. Subclinical depletion of primordial follicular reserve in mice treated with cyclophosphamide: Clinical importance and proposed accurate investigative tool. Human reproduction 14:1903-1907.

Meirow D, Nugent D. 2001. The effects of radiotherapy and chemotherapy on female reproduction. Human reproduction update 7:535-543.

Miller R R. 1980. Evaluation of nalbuphine hydrochloride. American journal of hospital pharmacy 37:942-949.

NIOSH (National Institute for occupational safety and health). 2011. Health hazard evaluation of deepwater horizon response workers. Available: http://www.cdc.gov/niosh/hhe/reports [Accessed 10 Mar. 2013]

Pappa T, Alevizaki M. 2012. Endogenous sex steroids and cardio- and cerebro-vascular disease in the postmenopausal period. European journal of endocrinology/European Federation of Endocrine Societies 167:145-156.

Pedersen T, Peters H. 1968. Proposal for a classification of oocytes and follicles in the mouse ovary. Journal of reproduction and fertility 17:555-557.

Picton H M, Harris S E, Muruvi W, Chambers E L. 2008. The in vitro growth and maturation of follicles. Reproduction 136:703-715.

Plancha C E, Sanfins A, Rodrigues P, Albertini D. 2005. Cell polarity during folliculogenesis and oogenesis. Reproductive biomedicine online 10:478-484.

Richards J S. 1994. Hormonal control of gene expression in the ovary. Endocrine reviews 15:725-751.

Roh J Y, Park Y K, Park K, Choi J. 2010. Ecotoxicological investigation of ceo(2) and tio(2) nanoparticles on the soil nematode *caenorhabditis elegans* using gene expression, growth, fertility, and survival as endpoints. Environmental toxicology and pharmacology 29:167-172.

Sato N, Kawamura K, Fukuda J, Honda Y, Sato T, Tanikawa H, et al. 2003. Expression of ldl receptor and uptake of ldl in mouse preimplantation embryos. Molecular and cellular endocrinology 202:191-194.

Shikanov A, Xu M, Woodruff T K, Shea L D. 2009. Interpenetrating fibrin-alginate matrices for in vitro ovarian follicle development. Biomaterials 30:5476-5485.

Sklar C. 2005 Maintenance of ovarian function and risk of premature menopause related to cancer treatment. Journal of the National Cancer Institute Monographs:25-27.

Sochova I, Hofman J, Holoubek I. 2007. Effects of seven organic pollutants on soil nematode *caenorhabditis elegans*. Environment international 33:798-804.

Spielmann H. 1998. Reproduction and development. Environmental health perspectives 106 Suppl 2:571-576.

Su Y Q, Sugiura K, Wigglesworth K, O'Brien M J, Affourtit J P, Pangas S A, et al. 2008. Oocyte regulation of metabolic cooperativity between mouse cumulus cells and oocytes: Bmp15 and gdf9 control cholesterol biosynthesis in cumulus cells. Development 135:111-121.

Su Y Q, Sugiura K, Li Q, Wigglesworth K, Matzuk M M, Eppig J J. 2010. Mouse oocytes enable 1 h-induced maturation of the cumulus-oocyte complex via promoting egf receptor-dependent signaling. Molecular endocrinology 24:1230-1239.

Sugiura K, Su Y Q, Diaz F J, Pangas S A, Sharma S, Wigglesworth K, et al. 2007. Oocyte-derived bmp15 and fgfs cooperate to promote glycolysis in cumulus cells. Development 134:2593-2603.

Sugiura K, Su Y Q, Li Q, Wigglesworth K, Matzuk M M, Eppig J J. 2009. Fibroblast growth factors and epidermal growth factor cooperate with oocyte-derived members of the tgfbeta superfamily to regulate spry2 mrna levels in mouse cumulus cells. Biology of reproduction 81:833-841.

Sugiura K, Su Y Q, Li Q, Wigglesworth K, Matzuk M M, Eppig J J. 2010. Estrogen promotes the development of mouse cumulus cells in coordination with oocyte-derived gdf9 and bmp15. Molecular endocrinology 24:2303-2314.

Sun F, Betzendahl I, Shen Y, Cortvrindt R, Smitz J, Eichenlaub-Ritter U. 2004. Preantral follicle culture as a novel in vitro assay in reproductive toxicology testing in mammalian oocytes. Mutagenesis 19:13-25.

Sun F, Betzendahl I, Van Wemmel K, Cortvrindt R, Smitz J, Pacchierotti F, et al. 2008. Trichlorfon-induced polyploidy and nondisjunction in mouse oocytes from preantral follicle culture. Mutation research 651:114-124.

Tingen C M, Kiesewetter S E, Jozefik J, Thomas C, Tagler D, Shea L, et al. 2011. A macrophage and theca cell-enriched stromal cell population influences growth and survival of immature murine follicles in vitro. Reproduction 141:809-820.

Trigatti B, Rayburn H, Vinals M, Braun A, Miettinen H, Penman M, et al. 1999 Influence of the high density lipoprotein receptor sr-bi on reproductive and cardiovascular pathophysiology. Proceedings of the National Academy of Sciences of the United States of America 96:9322-9327.

The National Academy of Sciences. 2007. Toxicity testing in the 21st century: A vision and a stragegy. Available: http://dels.nas.edu/best [accessed 12 Mar. 2013]

U.S. EPA (U.S. Environmental Protection Agency). 1996. Guidelines for reproductive toxicity risk assessment (FRL-5360-6). Available: http://www.epa.gov/raf/publications/guidelines-reproductive-tox-risk-assessment.htm [accessed 14 Mar. 2013].

Van Wemmel K, Gobbers E, Eichenlaub-Ritter U, Smitz J, Cortvrindt R. 2005. Ovarian follicle bioassay reveals adverse effects of diazepam exposure upon follicle development and oocyte quality. Reproductive toxicology 20:183-193.

Wallace W H, Shalet S M, Crowne E C, Morris-Jones P H, Gattamaneni H R, Price D A. 1989. Gonadal dysfunction due to cis-platinum. Medical and pediatric oncology 17:409-413.

Wang D, Xing X. 2008. Assessment of locomotion behavioral defects induced by acute toxicity from heavy metal exposure in nematode caenorhabditis elegans. Journal of environmental sciences 20:1132-1137.

Wang W, Craig Z R, Basavarajappa M S, Hafner K S, Flaws J A. 2012. Mono-(2-ethylhexyl) phthalate induces oxidative stress and inhibits growth of mouse ovarian antral follicles. Biology of reproduction 87:152.

West-Farrell E R, Xu M, Gomberg M A, Chow Y H, Woodruff T K, Shea L D. 2009. The mouse follicle microenvironment regulates antrum formation and steroid production: Alterations in gene expression profiles. Biology of reproduction 80:432-439.

WHO (World Health Organization). Reproductive health. Available from: http://www.who.int/topics/reproductive-_health/en/ [accessed 14 Mar. 2013].

Xu M, Banc A, Woodruff T K, Shea L D. 2009. Secondary follicle growth and oocyte maturation by culture in alginate hydrogel following cryopreservation of the ovary or individual follicles. Biotechnology and bioengineering 103:378-386.

Xu M, Fazleabas A T, Shikanov A, Jackson E, Barrett S L, Hirshfeld-Cytron J, et al. 2011. In vitro oocyte maturation and preantral follicle culture from the luteal-phase baboon ovary produce mature oocytes. Biology of reproduction 84:689-697.

Yanulevich J. 1983. Outpatient anesthesia with nalbuphine hydrochloride. AANA journal 51:395-397.

Yeh J, Kim B, Liang Y J, Peresie J. 2006. Mullerian inhibiting substance as a novel biomarker of cisplatin-induced ovarian damage. Biochemical and biophysical research communications 348:337-344.

Yucebilgin M S, Terek M C, Ozsaran A, Akercan F, Zekioglu O, Isik E, et al. 2004. Effect of chemotherapy on primordial follicular reserve of rat: An animal model of premature ovarian failure and infertility. The Australian & New Zealand journal of obstetrics & gynaecology 44:6-9.

Zeleznik A J. 2004. The physiology of follicle selection. Reproductive biology and endocrinology: R B&E 2:31.

Zhang Y, Chen D, Ennis A C, Polli J R, Xiao P, Zhang B, et al. 2013. Chemical dispersant potentiates crude oil impacts on growth, reproduction, and gene expression in caenorhabditis elegans. Archives of toxicology 87:371-382.

R. H. Hunter, The Fallopian tubes in domestic mammals: how vital is their physiological activity? Reproduction, nutrition, development 45, 281 (May-June, 2005).

H. B. Croxatto, Physiology of gamete and embryo transport through the fallopian tube. Reproductive biomedicine online 4, 160 (March-April, 2002).

P. Talbot B. D. Shur, D. G. Myles, Cell adhesion and fertilization: steps in oocyte transport, sperm-zona pellucida interactions, and sperm-egg fusion. Biology of reproduction 68, 1 (January, 2003).

L. A. Velasquez et al., PAF receptor and PAF acetylhydrolase expression in the endosalpinx of the human Fallopian tube: possible role of embryo-derived PAF in the control of embryo transport to the uterus. Human reproduction 16, 1583 (August, 2001).

H. Abe, M. Onodera, S. Sugawara, T. Satoh, H. Hoshi, Ultrastructural features of goat oviductal secretory cells at follicular and luteal phases of the oestrous cycle. journal of anatomy 195 (Pt 4), 515 (November, 1999).

S. Bauersachs et al., Monitoring gene expression changes in bovine oviduct epithelial cells during the oestrous cycle. Journal of molecular endocrinology 32, ~49 (April, 2004).

A. Bylander et al., Rapid effects of progesterone on ciliary beat frequency in the mouse fallopian tube. Reproductive biology and endocrinology: RB&E 8, 48 (2010).

T. Mahmood, E. Saridogan, S. Smutna, A. M. Habib, O. Djahanbakhch, The effect of ovarian steroids on epithelial ciliary beat frequency in the human Fallopian tube. Human reproduction 13, 2991 (November, 1998).

T. Nakahari et al., The regulation of ciliary beat frequency by ovarian steroids in the guinea pig Fallopian tube: interactions between oestradiol and progesterone. Biomedical research 32, 321 (October, 2011).

M. F. Erickson-Lawrence, T. T. Turner, T. S. Thomas, G. Oliphant Effect of steroid hormones on sulfated oviductal glycoprotein secretion by oviductal explants in vitro. *Biology of reproduction* 40, 1311 (Iun, 1989).

H. G. Verhage et al., Characteristics of an oviductal glycoprotein and its potential role in fertility control. *journal of reproduction and fertility. Supplement* 51,217 (1997).

We claim:

1. A microphysiologic system comprising:
   (a) an ovarian follicle 3D cell culture subsystem comprising at least a first cell type in 3D culture and a culture media for said first cell type; and
   (b) a fallopian tube 3D cell culture subsystem comprising at least a second cell type in 3D culture and a culture media for said second cell type;
   wherein the ovarian follicle 3D cell culture subsystem and the fallopian tube 3D cell culture subsystem are in unidirectional fluid communication such that fluid from the ovarian follicle 3D cell culture subsystem flows downstream to the fallopian tube 3D cell culture subsystem.

2. The microphysiologic system of claim 1, further comprising:
   (c) a uterine 3D cell culture subsystem comprising at least a third cell type in 3D culture and a culture media for said third cell type;
   wherein the fallopian tube 3D cell culture subsystem and the uterine 3D cell culture subsystem are in unidirectional fluid communication such that fluid from the fallopian tube 3D cell culture subsystem flows downstream to the uterine 3D cell culture subsystem.

3. The microphysiologic system of claim 2, further comprising:
   (d) an endocervical 3D cell culture subsystem comprising at least a fourth cell type in 3D culture and a culture media for said fourth cell type;
   wherein the uterine 3D cell culture subsystem and the endocervical 3D cell culture subsystem are in unidirectional fluid communication such that fluid from the uterine 3D cell culture subsystem flows downstream to the endocervical 3D cell culture subsystem.

4. The microphysiologic system of claim 3, further comprising:
   (e) an ectocervical 3D cell culture subsystem comprising at least a fifth cell type in 3D culture and a culture media for said fifth cell type;
   wherein the endocervical 3D cell culture subsystem and the ectocervical 3D cell culture subsystem are in unidirectional fluid communication such that fluid from the endocervical 3D cell culture subsystem flows downstream to the ectocervical 3D cell culture subsystem.

5. The microphysiologic system of claim 4, wherein factors secreted from cells in the ovarian follicle 3D cell culture subsystem flow downstream to the fallopian tube, uterine, endocervical, and/or ectocervical 3D cell culture subsystems, factors secreted from cells in the fallopian tube 3D cell culture subsystem flow downstream to the uterine, endocervical, and/or ectocervical 3D cell culture subsystems, factors secreted from cells in the uterine 3D cell culture subsystem flow downstream to the endocervical and/or ectocervical 3D cell culture subsystems 3D cell culture subsystem, and factors secreted from cells in the endocervical 3D cell culture subsystem flow downstream to the ectocervical 3D cell culture subsystem.

6. The microphysiologic system of claim 1, wherein the ovarian follicle 3D cell culture subsystem comprises one or more of granulosa cells, theca cells, and oocytes.

7. The microphysiologic system of claim 6, wherein the ovarian follicle 3D cell culture subsystem comprises one or more ovarian follicles in 3D culture.

8. The microphysiologic system of claim 7, wherein the ovarian follicles are polymer-encapsulated.

9. The microphysiologic system of claim 8, wherein the polymer comprises alginate.

10. The microphysiologic system of claim 7, wherein the ovarian follicles remain viable for at least one simulated menstrual cycle.

11. The microphysiologic system of claim 7, wherein the ovarian follicles respond to FSH and hCG stimulation by producing estrogen and progesterone in a pattern that mimics the human menstrual cycle.

12. The microphysiologic system of claim 11, wherein said estrogen and progesterone pass by unidirectional fluid communication to the fallopian tube 3D cell culture subsystem.

13. The microphysiologic system of claim 12, wherein cells of the fallopian tube 3D cell culture subsystem respond to said estrogen and/or progesterone with one or more of cilliary beating, increased oviductal glycoprotein 1 (OVGP1) expression, and cilliary beat frequency (CBF) and/or insulin-like growth factor 1 (IGF1) secretion.

14. The microphysiologic system of claim 1, wherein the fallopian tube 3D cell culture subsystem comprises one or both of secretory epithelial cells and ciliated epithelial cells.

15. The microphysiologic system of claim 14, wherein the fallopian tube 3D cell culture subsystem comprises fallopian epithelium tissue pieces grown on media-permeable cell supports.

16. The system of claim 14, wherein the fallopian tube system remains viable and maintains both secretory and ciliated epithelium cell phenotypes for at least one simulated menstrual cycle.

17. The microphysiologic system of claim 1, wherein the uterine 3D cell culture subsystem comprises one or more of endometrial epithelial cells, endometrial stromal cells, myometrial smooth muscle cells, and myometrial fibroblast cells.

18. The microphysiologic system of claim 1, wherein the endocervical 3D cell culture subsystem comprises one or both of endocervical epithelial cells and endocervical stromal cells.

19. The microphysiologic system of claim 1, wherein the ectocervical 3D cell culture subsystem comprises one or both of ectocervical epithelial cells, J2-3T3 fibroblasts, and ectocervical stromal cells.

20. The microphysiologic system of claim 1, comprising a microfluidic component that provides said unidirectional fluid communication.

21. A microphysiologic system comprising:
   (a) an ovarian follicle 3D cell culture subsystem comprising granulosa cells, theca cells, and/or oocytes in 3D culture;
   (b) a fallopian tube 3D cell culture subsystem comprising secretory epithelial cells and/or ciliated epithelial cells in 3D culture;
   (c) a uterine 3D cell culture subsystem comprising endometrial epithelial cells, endometrial stromal cells, myometrial smooth muscle cells, and/or myometrial fibroblast cells in 3D culture;
   (d) an endocervical 3D cell culture subsystem comprising endocervical epithelial cells and/or endocervical stromal cells in 3D culture; and
   (e) an ectocervical 3D cell culture subsystem comprising ectocervical epithelial cells, J2-3T3 fibroblasts, and/or ectocervical stromal cells in 3D culture;

wherein the ovarian follicle 3D cell culture subsystem and the fallopian tube 3D cell culture subsystem are in unidirectional fluid communication such that fluid and factors from the ovarian follicle 3D cell culture subsystem flow downstream to the fallopian tube 3D cell culture subsystem;

wherein the fallopian tube 3D cell culture subsystem and the uterine 3D cell culture subsystem are in unidirectional fluid communication such that fluid and factors from the fallopian tube 3D cell culture subsystem flow downstream to the uterine 3D cell culture subsystem;

wherein the uterine 3D cell culture subsystem and the endocervical 3D cell culture subsystem are in unidirectional fluid communication such that fluid and factors from the uterine 3D cell culture subsystem flow downstream to the endocervical 3D cell culture subsystem;

wherein the endocervical 3D cell culture subsystem and the ectocervical 3D cell culture subsystem are in unidirectional fluid communication such that fluid and factors from the endocervical 3D cell culture subsystem flow downstream to the fourth ectocervical 3D cell culture subsystem.

* * * * *

UNITED STATES PATENT AND TRADEMARK OFFICE
CERTIFICATE OF CORRECTION

PATENT NO. : 9,695,399 B2  
APPLICATION NO. : 14/607862  
DATED : July 4, 2017  
INVENTOR(S) : Woodruff et al.

It is certified that error appears in the above-identified patent and that said Letters Patent is hereby corrected as shown below:

In the Claims

Column 57, Claim 21, Line 22-23 should read:  
flow downstream to the ectocervical 3D cell culture subsystem.

Signed and Sealed this  
Nineteenth Day of September, 2017

Joseph Matal  
*Performing the Functions and Duties of the*  
*Under Secretary of Commerce for Intellectual Property and*  
*Director of the United States Patent and Trademark Office*